US006858207B2

(12) United States Patent
Ford et al.

(10) Patent No.: US 6,858,207 B2
(45) Date of Patent: Feb. 22, 2005

(54) METHODS AND MATERIALS RELATING TO NOVEL CD39-LIKE POLYPEPTIDES

(75) Inventors: John Ford, San Mateo, CA (US); Julio J. Mulero, Palo Alto, CA (US)

(73) Assignee: Nuvelo, Inc., Sunnyvale, CA (US)

( * ) Notice: Subject to any disclaimer, the term of this patent is extended or adjusted under 35 U.S.C. 154(b) by 221 days.

(21) Appl. No.: 10/091,085

(22) Filed: Mar. 5, 2002

(65) Prior Publication Data

US 2002/0146772 A1 Oct. 10, 2002

Related U.S. Application Data

(63) Continuation of application No. 09/350,836, filed on Jul. 9, 1999, now Pat. No. 6,387,645, and a continuation-in-part of application No. 09/244,444, filed on Feb. 4, 1999, now abandoned, which is a continuation-in-part of application No. 09/273,447, filed on Mar. 19, 1999, now abandoned, which is a continuation-in-part of application No. 09/122,449, filed on Jul. 24, 1998, now abandoned, which is a continuation-in-part of application No. 09/118,205, filed on Jul. 16, 1998, now abandoned.

(51) Int. Cl.$^7$ .............................................. A61K 38/46

(52) U.S. Cl. .................... 424/94.6; 424/185.1; 530/350

(58) Field of Search ............................. 424/185.1, 94.6; 530/350

(56) References Cited

U.S. PATENT DOCUMENTS

| | | | |
|---|---|---|---|
| 4,235,871 A | 11/1980 | Papahadjopoulos et al. | |
| 4,501,728 A | 2/1985 | Geho et al. | |
| 4,683,195 A | 7/1987 | Mullis et al. | |
| 4,737,323 A | 4/1988 | Martin et al. | |
| 4,837,028 A | 6/1989 | Allen | |
| 4,946,778 A | 8/1990 | Ladner et al. | |
| 4,959,314 A | 9/1990 | Mark et al. | |
| 4,965,188 A | 10/1990 | Mullis et al. | |
| 5,202,231 A | 4/1993 | Drmanac et al. | |
| 5,525,464 A | 6/1996 | Drmanac et al. | |
| 6,387,645 B1 | 5/2002 | Ford et al. | |

FOREIGN PATENT DOCUMENTS

| | | |
|---|---|---|
| CA | 2148851 | 10/1996 |
| WO | WO 90/03382 | 4/1990 |
| WO | WO 90/14148 | 11/1990 |
| WO | WO 91/09955 | 7/1991 |
| WO | WO 92/20808 | 11/1992 |
| WO | WO 94/12650 | 6/1994 |
| WO | WO 95/09248 | 4/1995 |
| WO | WO 96/30532 | 10/1996 |
| WO | WO 96/32471 | 10/1996 |

OTHER PUBLICATIONS

Grinthal et al, Biochemistry 39: 9–16, 2000.*
Ngo et al., in The Protein Folding Problem and Tertiary Structure Prediction, 1994, Merz, et al., (ed.), Birkhauser, Boston, MA, pp. 433 and 492:495.*
Mikayama et al, Molecular cloning and functional expression of a cDNA encoding gycosylation–inhibting factor, Nov. 1993, Pro Natl. Acad. Sci, USA vol. 90: 10056–10060.*
Skolnick et al., From genes to protein structure and function: novel applications of computational approaches in the genomic era, Jan. 2000, Trends in Biotech. 18(1): 34–39.*
Attwood et al., The babel of bioinformatics, Oct. 2000, Science 290 (5491): 471–473.*
Gennaro et al, in Remington's Pharmaceutical Sciences, eighteenth edition, 1990, pp. 1300–1329.*
Harlow et al in Antibodies a Laboratory Manual, 1998, Cold Spring harbor laboratory publication, Cold Spring Harobr, NY, pp. 287.*
Adelman, J. P. et al., "In Vitro Deletional Mutagenesis for Bacterial Production of the 20,000–Dalton Form of Human Pituitary Growth Hormone," *DNA*, 2(3):183–193 (1983).
Altschul, S.F.et al., "Basic Local Alignment Search Tool," *J. Mol. Biol.*, 215:403–410 (1990).
Altschul, S.F., "A Protein Alignment Scoring System Sensitive at All Evolutionary Distances," *J. Mol. Evol.*, 36:290–300 (1993).
Anderson, W.F., "Human Gene Therapy," *Nature (Supp.)*, 392:25–30 (1998).
Asseline, U. et al., "Nucleic Acid–Binding Molecules with High Affinity and Base Sequence Specificity: Intercalating Agents Covalently Linked to Oligodeoxynucleotides," *Proc. Natl. Acad. Sci., USA*, 81:3297–3301 (1984).
Bayer, E.A. et al., "The Avidin–Biotin Complex in Affinity Cytochemistry," *Meth. Enzym.*, 62:308–315 (1979).
Beal, P.A. et al., "Second Structural Motif for Recognition of DNA by Oligonucleotide–Directed Triple–Helix Formation," *Science*, 251:1360–1363 (1991).
Bonaldo, M. et al., "Normalization and Subtraction: Two Approaches to Facilitate Gene Discovery," *Genome Res.*, 6:791–806 (1996).
Boorstein et al., "Primer Extension Analysis of RNA," *Methods Enzymol.*, 180:347–369 (1989).
Breslauer, K.J., "Predicting DNA Duplex Stability from the Base Sequence," *Proc. Natl. Acad. Sci., USA*, 83: 3746–3750 (1986).
Broude, N.E. et al., "Enhanced DNA Sequencing by Hybridization," *Proc. Natl. Acad. Sci., USA*, 91:3072–3076 (1994).

(List continued on next page.)

*Primary Examiner*—Christina Chan
*Assistant Examiner*—Phuong N. Huynh
(74) *Attorney, Agent, or Firm*—Renee S. Polizotto

(57) ABSTRACT

The invention provides novel polynucleotides isolated from cDNA libraries of human fetal liver-spleen and macrophage as well as polypeptides encoded by these polynucleotides and mutants or variants thereof. The polypeptides correspond to a novel human CD39-like protein. Other aspects of the invention include vectors containing polynucleotides of the invention and related host cells as well a processes for producing novel CD39-like polypeptides, and antibodies specific for such polypeptides.

3 Claims, 7 Drawing Sheets

OTHER PUBLICATIONS

Brumbaugh, J.A. et al., "Continuous, On–line DNA Sequencing Using Oligonucleotide Primers with Multiple Fluorophores," *Proc. Natl. Acad. Sci., USA*, 85:5610–5614 (1988).

Burnstock. G., "The Past, Present and Future of Purine Nucleotides as Signalling Molecules," *Neuropharmacology*, 36:1127–1139 (1997).

Cate, R.L. et al. "Genomic Southern Analysis with Alkaline–Phosphatase–Conjugated Oligonucleotide Probes and the Chemiluminescent Substrate AMPPD," *Genet. Anal. Tech. Appl.*, 8(3):102–106 (1991).

Chadwick, B. P. et al., "Cloning and Mapping of a Human and Mouse Gene with Homology to Ecto–ATPase Genes," *Mammalian Genome*, 9:668–672 (1997).

Chadwick, B.P. et al. "cDNA Cloning and Chromosomal Mapping of a Mouse Gene with Homology to NTPases," *Mammalian Genome*, 9:162–164 (1998).

Chadwick B.P. et al., "The CD39–like Gene Family: Identification of Three New Human Members (CD36L2, CD39L3, and CD39L4), Their Murine Homologues, and a Member of the Gene Family from *Drosophila melanogaster,*" *Genomics*, 50:357–367 (1998).

Cole, S.P.C. et al., "The EBV–Hybridoma Technique and It's Application to Human Lung Cancer," *Monoclonal Antibodies and Cancer Therapy*, Alan R. Liss, Inc., pp. 77–96 (1985).

Communi, D. et al., "Cloning, Functional Expression and Tissue Distribution of the Human $P2Y_6$ Receptor," *Biochem. Biophys. Res. Com.*, 222:.303–308 (1996).

Cooney, M. et al., "Site–Specific Oligonucleotide Binding Represses Transcription of the Human c–myc Gene in Vitro," *Science, 15241*:456–459 (1988).

Craig, M.E. et al., "Relaxation Kinetics of Dimer Formation by Self Complementary Oligonucleotides," *J. Mol. Biol.*, 62:383–401 (1971).

Dahlén et al., "Sensitive Detection of Genes by Sandwich Hybridization and Time–Resolved Fluorometry," *Mol. Cell. Probes (England)*, 1:159–168 (1987).

Daly, J. et al., "Direct Method for Determining Inorganic Phosphate in Serum with the CentrifiChem," *Clin. Chem.*, 18:263–265 (1972).

Dolinnaya, N.G. et al., "Site–directed Modification of DNA Duplexes by Chemical Ligation," *Nucleic Acids Research, (England)*, 16(9):3721–3738 (1988).

Dolinnaya, N.G. et al., "The use of BrCN for assembling modified DNA duplexes and DNA–RNA hybrids; comparison with water–soluble carbodiimide," *Nucleic Acids Res. (ENGLAND)*, 19(11):3067–72 (1991).

Drmanac, R. et al., "A calculation of fragment lengths from human DNA with 78 restriction enzymes: an aid for cloning and mapping," *Nucleic Acids Research*, 14(11): 4691–4692 (1986).

Drmanac, R. et al., "Sequencing of Megabase Plus DNA by Hybridization: Theory of the Method," *Genomics*, 4:114–128 (1989).

Drmanac, R. et al., "Reliable Hybridization of Oligonucleotides as Short as Six Nucleotides," *DNA Cell Biol.*, 9:527–534 (1990).

Drmanac, R. et al., "An Algorithm for the DNA Sequence Generation from k–Tuple Word Contents of the Minimal Number of Random Fragments," *J. Biomol. Struct. Syn.*, 8(5): 1085–1102 (1991).

Drmanac, R. et al., "Sequencing By Oligonucleotide Hybridization: A Promising Framework in Decoding of the Genome Program?" *Proceedings of the First International Conference Electrophoresis Supercomputing Human Genome*, Cantor et al., (Eds.), World Scientific Publishing Co., Singapore, pp. 47–59 (1991).

Drmanac, R. et al., "W (A or T) Sequences as Probes and Primers Suitable for Genomic Mapping and Fingerprinting," *Nucleic Acids Research*, 19(21):5839–5842 (1991).

Drmanac, R. et al., "DNA Sequence Determination by Hybridization: A Strategy for Efficient Large–Scale Sequencing," *Science*, 260(5114):1649–1652 (1993).

Drmanac, S. et al., "Processing of cDNA and Genomic Kilobase–Size Clones for Massive Screening, Mapping and Sequencing by Hybridization," *Biotechniques*, 17:328–329, 332–336 (1994).

Dubyak, G. R. et al., "Signal Transduction via $P_2$–Purinergic Receptors for Extrecellular ATP and Other Nucleotides," *Am. J. Physiol.*, 34:C577–C606 (1993).

Duncan, C.H. et al., "Affinity Chromatography of a Sequence–Specific DNA Binding Protein using Teflon–linked Oligonucleotides," *Anal. Biochem.*, 169:104–108 (1988).

Engval, E. et al., "Enzyme–Linked Immunosorbent Assay, ELISA III. Quantitation of Specific Antibodies by Enzyme–Labeled Anti–Immunoglobulin in Antigen–Coated Tubes," *Immunol.*, 109:129–135 (1972).

Fischer Y. et al., "Purinergic Inhibition of Glucose Transport in Cardiomyocytes," *J. Biol. Chem.*, 274:755–761 (1999).

Friedmann, T., "Progress Toward Human Gene Therapy," *Science*, 244:1275–1281 (1989).

Gayle III, R.B. et al., "Inhibition of Platelet Function by Recombinant Soluble Ecto– ADPase/CD39," *J. Clinical Investigation*, 101(9):1851–1859 (1998).

Gluzman, Y., "SV40–Transformed Simian Cells Support the Replication of Early SV40 Mutants," *Cell*, 23:175–182 (1981).

Goding J.W., "Conjugation of Antibodies with Fluorochromes: Modifications to the Standard Methods," *J. Immunol. Meth.*, 13:215–226 (1976).

Gouttefangeas, C. et al., "The CD39 Molecule Defines Distinct Cytotoxic Subsets within Alloactivated Human CD8–Positive Cells," *Eur. J. Immunol.*, 22:2681–2685 (1992).

Hillenkamp, F. et al., "Matrix Assisted UV–Laser Desorption/Ionization: A New Approach to Mass Spectrometry of Large Biomolecules," In: *Biological Mass Spectrometry*, Burlingame et al., (eds.), Elsvier Science Pub., Amsterdam, p. 49–60 (1990).

Hoheisel at al., "Quantitative Measurements on the Duplex Stability of 2,6–Diaminopurine and 5–Chloro–Uracil Nucleotides using Enzymatically Synthesized Oligomers" *FEBS Lett*, 274:103–106 (1990).

Hurby et al., "Application of Synthetic Peptides: Antisense Peptides," In *Synthetic Peptides, A User's Guide*, W.H. Freeman, NY, pp. 289–307 (1992).

Huth–Fehre, T. et al., "Matrix Assisted Laser Desorption Mass Spectrometry of Oligodeoxythymidylic Acids," *Rapid Comm. Mass Spect.*, 6:209–213 (1992).

Ikuta, S. et al., "Dissociation Kinetics of 19 Base Paired Oligonucleotide–DNA Duplexes Containing Different Single Mismatched Base Pairs," *Nucleic Acids Research*, 15:797–811 (1987).

Inouye, S. et al., "Microplate Hybridization of Amplified Viral DNA Segment," *J. Clin. Microbiol.*, 28:1469–1472 (1990).

Kaczmarek, E. et al., "Identification and Characterization of CD39/Vascular ATP Diphosphohydrolase," *J. Biol. Chem.*, 271:33116–33122 (1996).

Kansas, G. S. et al., "Expression, Distribution, and Biochemistry of Human CD39 Role in Activation–Associated Homotypic Adhesion of Lymphocytes," *J. Immuno.*, 146:2235–2244 (1991).

Kasprzak, A. et al., "Location of a Contact Site between Actin and Myosin in the Three–Dimensional Structure of the Acto–S1 Complex," *Biochemistry*, 28:9230–9238 (1989).

Kirley, T.L., "Complementary DNA Cloning and Sequencing of the Chicken Muscle Ecto–ATPase," *J. Biol. Chem.*, 272:1076–1081 (1997).

Kohler, G. et al., "Continuous Cultures of Fused Cells Secreting Antibody of Predefined Specificity," *Nature*, 256:495–497 (1975).

Kozbor, D. et al., "The Production of Monoclonal Antibodies from Human Lymphocytes," *Immunology Today*, 4:72–79(1983).

Lamture, J., "Direct Detection of Nucleic Acid Hybridization on the Surface of a Charge Coupled Device," *Nucleic Acids Research*, 22:2121–2125 (1994).

Landegren, U. et al., "A Ligase–Mediated Gene Detection Technique," *Science*, 241:1077–1080 (1988).

Lee, J.S. et al., "Complexes formed by $(pyrimidine)_n (purine)_n$ DNAs on lowering the pH are three–stranded," *Nucl. Acids Res.*, 6:3073–3091 (1979).

Lehrach, H. et al., "Hybridization Fingerprinting in Genome Mapping and Sequencing," in: *Genome Analysis vol. I: Genetic and Physical Mapping*, Cold Spring Harbor Laboratory Press, pp. 39–81 (1990).

Lutz, Y. et al., "The Distribution of Two hnRNP–Associated Proteins Defined by a Monoclonal Antibody Is Altered in Heat–Shocked HeLa Cells," *Exp. Cell Research.*, 175:109–124 (1988).

Makita, K. et al., "Placental ecto–ATP diphosphohydrolase: its structural feature distinct from CD39, localization and inhibition on shear–induced platelet aggregation," *International J. Hematology*, 68:297–310 (1998).

Maliszewski, C. R. et al., "The CD39 Lymphoid Cell Activation Antigen," *J. Immunology*, 153:3574–3583 (1994).

Marcus, A.J. et al., "The Endothelial Cell Ecto–ADPase Responsible for Inhibition of Platelet Function is CD39," *J. Clinical Investigation*, 99(6):1351–1360 (1997).

Miller, A.D., "Human Gene Therapy Comes of Age," *Nature*, 357:455–460 (1992).

Morrisey, D. et al., "Nucleic Acid Hybridization Assays Employing dA–Tailed Capture Probes. I. Single Capture Methods," *Mol. Cell. Probes*, 2:189–207 (1989).

Mulero, J.J. et al., "CD39–L4 Is a Secreted Human Apyrase, Specific for the Hydrolysis of Nucleoside Diphosphates," *J. Biol. Chem.*, 274(29):20064–20067 (1999).

Murakami, A. et al., "Fluorescent–Labeled Oligonucleotide Probes : Detection of Hybrid Formation in Solution by Fluorescence Polarization Spectroscopy," *Nucleic Acids Res.*, (*ENGLAND*), 19:4097–102 (1991).

Nagata, Y. et al., "Quantification of Picogram Levels of Specific DNA Immobilized in Microtiter Wells," *FEBS Lett* (*NETHERLANDS*), 183: 379–382 (1985).

Neumann, P.E. et al., "Mapping of Tow Genes that Influence Susceptibility to Audiogenic Seizures in Crosses of C57BL/6J and DBA/2J Mice," *Behavior Genetics*, 20:307–323 (1990).

Nichols, R. et al. "A Universal Nucleoside for Use at Ambiguous Sites in DNA Primers," *Nature*, 369:492–493 (1994).

Nizetic, D. et al., "An Improved Bacterial Colony Lysis Procedure Enables Direct DNA Hybridisation Using Short (10, 11 bases) Oligonucleotides to Cosmids," *Nucleic Acids Research*, 19:182 (1991).

Okano, H. et al., "Myelin Basic Protein Gene and the Function of Antisense RNA in Its Repression in Myelin–Deficient Mutant Mouse," *Neurochem.*, 56:560–567 (1991).

Ottman, R. et al., "Localization of a Gene for Partial Epilepsy to Chromosome 10q," *Nature Genet.*, 10:56–60 (1995).

Paterson, B.M. et al., "Structural Gene Identification and Mapping by DNA–mRNA Hybrid–Arrested Cell–Free Translation," *Proc. Natl. Acad. Sci.*, 74:4370–4374 (1977).

Paunesku, T. et al., "Origin of Rat β–Globin Haplotypes Containing Three and Five Genes," *Mol. Biol. Evol.*, 7:407–422 (1990).

Pease, A.C. et al., "Light–generated Oligonucleotide Arrays for Rapid DNA Sequence Analysis," *Proc. Natl. Acad. Sci., USA*, 91:5022–5026 (1994).

Pevzner, P.A., "1 –Tuple DNA Sequencing: Computer Analysis," *J. Biomol. Struct. & Dyn.*, 7(l):63–73 (1989).

Pontius, B.W. et al., "Rapid Renaturation of Complementary DNA Strands Mediated by Cationic Detergents: A Role for High–Probability Binding Domains in Enhancing the Kinetics of Molecular Assembly Processes," *Proc. Natl. Acad. Sci., USA*, 88:8237–8241 (1991).

Pörshke, D. et al., "Co–operative Non–enzymic Base Recognition," *J. Mol. Biol.*, 62:361–381 (1971).

Rasmussen, S.R. et al., "Covalent Immobilization of DNA onto Polystyrene Microwells: The Molecules Are Only Bound at the 5' End," *Anal. Biochem.*, 198:138–142 (1991).

Rowe, M. et al., "Monoclonal Antibodies to Epstein–Barr Virus–Induced, Transformation–Associated Cell Surface Antigens: Binding Patterns and Effect Upon Virus–Specific T–Cell Cytotoxicity," *Int. J. Cancer*, 29:373–381 (1982).

Sambrook, J. et al., In: *Molecular Cloning A Laboratory Manual*, 2nd Ed., Cold Springs Harbor Press, pp. 9.14–9.28 (1989).

Schoenborn, M.A. et al., "Gene Structure and Chromosome Location of Mouse Cd39 Coding for an Ecto–Apyrase," *Cytogenetics & Cell Genetics*, 81:287–289 (1998).

Schriefer, L.A. et al., "Low Pressure DNA Shearing: A Method for Random DNA Sequence Analysis," *Nucleic Acids Res.* (ENGLAND), 18(24):7455–6 (1990).

Schubert, F. et al., "One–step Labelling of Oligonucleotides with Fluoresceine During Automated Synthesis," *Nucleic Acids Res.* (*ENGLAND*), 18:3427 (1990).

Schulman E. S. et al., "ATP Modulates Anti–IgE–Induced Release of Histamine from Human Lung Mast Cells," *Am. J. Respir. Cell Mol. Biol.*, 20:530–537 (1999).

Seyfried, T.N. et al., "Genetic Linkage Between the AH Locus and a Major Gene that Inhibits Susceptibility to Audiogenic Seizures in Mice," *Genetics*, 99:117–126 (1981).

Skobel, E. et al., "Relation Between Enzyme Release and Irreversible Cell Injury of the Heart under the Influence of Cytoskeleton Modulating Agents," *Biochim. Biophys. Acta*, 1362:128–134 (1997).

Smith, R.D. et al., "New Developments in Biochemical Mass Spectrometry: Electrospray Ionization," *Anal. Chem.*, 62:882–899 (1990).

Smith, T.M. et al., "Cloning, Sequencing, and Expression of a Human Brain Ecto–Apyrase Related to Both the Ecto–ATPases and CD39 Ecto–Apyrases," *Biochim. Biophys Acta*, 1386:65–78 (1998).

Somers, G.R. et al., "Expression of the P2Y6 Purinergic Receptor in Human T Cells Infiltrating Inflammatory Bowel Disease," *Lab. Invest.*, 78:1375–1383 (1998).

Sternberger, L.A. et al., "The Unlabeled Antibody Enzyme Method of immunohistochemistry—Preparation and Properties of Soluble Antigen–Antibody Complex (Horseradish Peroxidase–Antihoreseradish Peroxidase) and Its Use in Identification of Spriochetes," *J. Histochem. Cytochem.*, 18:315–333 (1970).

Stevanovi, M. et al., Variant chromosomal arrangement of adult β–globin genes in rat *Gene*, 79:139–150 (1989).

Strezoska, Z. et al., "DNA Sequencing by Hybridization: 100 Bases Read by a Non–Gel–Based Method," *Proc. Natl. Acad. Sci.*, USA, 88:10089–10093 (1991).

Van Ness, J. et al., "A Versatile Solid Support System for Oligodeoxynucleotide Probe–Based Hybridization Assays," *Nucleic Acids Res.*, (ENGLAND) 19:3345–3350 (1991).

Verma, I.M., "Gene Therapy—Treatment of Disease by Introducing Healthy Genes into the Body is Becoming Feasible. But the Therapy will not Reach its Full Potential until the Genes Can Be Coaxed to Work throughout Life," *Scientific American*, pp. 68–72, 81–84 (1990).

Vollrath, D. et al., "The Human Y Chromosome: A 43–Interval Map Based on Naturally Occurring Deletions," *Science*, 258:52–59 (1992).

Wallace, R.B. et al., "Hybridization of Synthetic Oligodeoxyribonucleotides to $\Phi_X$ 174 DNA: The Effect of Single Base Pair Mismatch," *Nucleic Acids Research*, 6:3543–3557 (1979).

Walsh P.S. et al., "Preferential PCR Amplification of Alleles: Mechanisms and Solutions," *PCR Methods Appl*, 1:241–250 (1992).

Wang, T–F. et al., "CD39 Is an Ecto–($Ca^{2+}$, $Mg^{2+}$)–apyrase," *J. Biol. Chem.*, 271(17):9898–9901 (1996).

Wang T–F. et al., "Characterization of Brain Ecto–Apyrase: Evidence for Only One Ecto–Apyrase (CD39) Gene," *Molecular Brain Research*, 47:295–302 (1997).

Wang, T–F. "Widespread Expression of Ecto–Apyrase (CD39) in the Central Nervous System," *Brain Research*, 790:318–322 (1998).

Wang T–F et al., "The Transmembrane Domains of Ectoapyrase (CD39) Affect Its Enzymatic Activity and Quarternary Structure," *J. Biol. Chem.*, 273:24814–24821 (1998).

Wells, J.A. et al., "Cassette Mutagenesis: An Efficient Method for Generation of Multiple Mutations at Defined Sites," *Gene*, 34:315–323 (1985).

Wolter, A. et al., "Negative Ion FAB Mass Spectrometric Analysis of Non–Charged Key Intermediates in Oligonucleotide Synthesis: Rapid Identification of Partially Protected Dinucleoside Monophates," *Biomedical Environ. Mass Spec.*, 14:111–116 (1987).

Xu, L. et al., "Ketone Electrophores and an Olefin–Release Group Electrophore– Labeled DNA Oligomer Detection via Electron Capture," *Chromatography*, 764:95–102 (1997).

Yamashita, M. et al., "Electrospray Ion Source. Another Variation on the Free–Jet Theme," *J. Phys. Chem.*, 88:4451–4459 (1984).

Zoller, M.J. et al., Oligonucleotide–Directed Mutagenesis Using M13–Derived Vectors: An Efficient and General Procedure for the Production of Point Mutations in any Fragment of DNA, *Nucleic Acids Res*, 10:6487–6500 (1982).

Fingl et al., "General Principles," In: *The Pharmacological Basis of Therapeutics*, Chapter 1, pp. 1–46 (1975).

Geiger et al., "Ligand specificity and ticlopidine effects distinguish three human platelet ADP receptors," *European Journal Pharmacology*, 351:235–246 (1998).

Hechler et al., "ATP Derivatives Are Antagonists of the P2Y1 Receptor: Similarities to the Platelet ADP Receptor," *American Pharmacology*, 53:727–733 (1998).

Ingall et al., "Antagonists of the Platelet $P_{2T}$ Receptor: A Novel Approach to Antithrombotic Therapy," *J. Med. Chem.*, 42:213–220 (1999).

Jantzen et al., "Evidence for Two Distinct G–protein–coupled ADP Receptors Mediating Platelet Activation," *Thromb. Haemost.*, 81:111–117 (1999).

Myers et al., "Automated Double–Label: In Situ Hybridization and Immunohistochemistry," *J. Surg Path.*, 1:191–203 (1995).

Vigne et al., "Benzoyl ATP Is an Antagonist of Rat and Human P2Y1 Receptors and of Platelet Aggregation," *Biochem. Biophys. Res. Commun.*, 256:94–97 (1999).

Boukerche, H. et al., "Human melanoma cell lines differ in their capactiy to release ADP and aggregate platelets," *Br. J. Haematol.*, 87(4):763–72 (1994).

Dzhaudzhugazyan, K.N. et al., "Ecto–ATP diphosphohydrolase/CD39 is overexpressed in differentiated human melanomas," *FEBS Lett.*, 430(3):227–30 (1998).

Clifford, E.E. et al., "Stage–specific expression of P2Y receptors ecto–apyrase, and ecto–5'–nucteotidase in myeloid leukocytes," *Am. J. Physiol.*, 273(3 Pt. 1):C973–87 (1997).

Katzur, A.C., et al., "Expression and responsiveness of P2Y2 receptors in human endometrial cancer cell lines, " *J. Clin. Endocrinol. Metab.*, 84(11):4085–91 (1999).

Correale, P., et al., Extracellular adenosine 5' triphosphate involvement in the death of LAK–engaged human tumor cells via P2X–receptor activation, *Immunol. Lett.*, 15(2):69–78 (1997)

Barnard. E.A., et al., "Nucleotide receptors in the nervous system. An abundant component using diverse transduction mechanisms," *Mol. Neurobiol.* 15(2):103–29 (1997).

Abbracchio, M.P. and Burnstock G., "Purinoreceptors: Are there families of P2X and P2Y Purinoreceptors?," *Pharmac. Ther.*, 64:445–75 (1994).

Illes, P. et al., "Electrophysiological effects of ATP on brain neurones," *J. Auton. Pharmacol.*, 16(6)407–11 (1996).

Barnard, E.A., et al., "The diverse series of recombinant P2Y purinoreceptors," *Ciba Found. Symp.*, 198:166–88 (1996).

Williams, M. and Jarvis, M.F., "Purinergenic and pyrimidinergenic receptors as potential drug targets," *Biochem. Pharmacol.*, 59(10):1173–85 (2000).

King, B.F. et al., "Metabotropic receptors for ATP and UTP: exploring the correspondence between native and recombinant nucleotide receptors," *Trends Pharmacol. Sci.*, 19(12):506–14 (1998).

Nicholas, R.A., et al., "Pharmacological and second messenger signaling selectivities of cloned P2Y receptors," *J. Auton. Pharmacol.*, 16(6):319–23 (1996).

Moore, D., et al. "Regional and cellular distribution of the P2Y(l) purinergic receptor in the human brain: striking neuronal localisation," *J. Comp. Neurol.*, 421(3):374–84 (2000).

Sneddon. D., et al., "Modulation of purinergic neurotransmission." *Prog. Brain. Res.*, 120:11–20 (1999).

Hicks–Berger, C.A., et al., "Expression and Characterization of soluble and Membrane–bound Human Nucleoside Triphosphate Diphosphohydrolase 6 (CD39L2)," *J. Biol. Chem.*, 275(44):34041–34045 (2000).

Enjyoji, et al., "Targeted disruption of cd39/ATP diphosphohydrolase results in disordered homeostasis and thromboregulation," *Nature Medicine* 5(9):1010–1017 (1999).

* cited by examiner

SEQ ID NO:1:
GGCATATTAGCTTGGGTTACTGTGAATTTTCTGACAGGTCAGCTGCATGGCCACAGA
CAGGAGACTGTGGGGACCTTGGACCTAGGGGGAGCCTCCACCCAAATCACGTTCCT
GCCCCAGTTTGAGAAAACTCTGGAACAAACTCCTAGGGGCTACCTCACTTCCTTTGA
GATGTTTAACAGCACTTATAAGCTCTATACACATAGTTACCTGGGATTTGGATTGAA
AGCTGCAAGACTAGCAACCCTGGGAGCCCTGGAGACAGAAGGGACTGATGGGCACA
CTTTCCGGAGTGCCTGT

SEQ ID NO:2:
GCGGGCTGCCGCGCAAGGGTGGCGCGCGCGCGTTTTCCTTGTTCCTGGTCAACAAAG
AAATGTGGAGTGTCTTGGCTGAATCCTCATACAGACAAGATCATTATGGTGCTGTTA
GGTTGAAAAAGTGATATAATAAAGGAACCAAGGAGAAAATTCAGAAGGAAAGAAA
AAATTGCCTCTGCAGGTGTGCGAGCAGGATTGCTTCTGCAACAAAAGCCTCCACCCA
GCCACATCTTGGGAAAAGAATGGCCACTTCTTGGGGCACAGTCTTTTTCATGCTGGT
GGTATCCTGTGTTTGCAGCGCTGTCTCCCACAGGAACCAGCAGACTTGGTTTGAGGG
TATCTTCCTGTCTTCCATGTGCCCCATCAATGTCAGCGCCAGCACCTTGTATGGAATT
ATGTTTGATGCAGGGAGCACTGGAACTCGAATTCATGTTTACACCTTTGTGCAGAAA
ATGCCAGGACAGCTTCCAATTCTAGAAGGGGAAGTTTTTGATTCTGTGAAGCCAGGA
CTTTCTGCTTTTGTAGATCAACCTAAGCAGGGTGCTGAGACCGTTCAAGGGCTCTTA
GAGGTGGCCAAAGACTCAATCCCCCGAAGTCACTGGAAAAAGACCCCAGTGGTCCT
AAAGGCAACAGCAGGACTACGCTTACTGCCAGAACACAAAGCCAAGGCTCTGCTCT
TTGAGGTAAAGGAGATCTTCAGGAAGTCACCTTTCCTGGTACCAAAGGGCAGTGTTA
GCATCATGGATGGATCCGACGAAGGCATATTAGCTTGGGTTACTGTGAATTTTCTGA
CAGGTCAGCTGCATGGCCACAGACAGGAGACTGTGGGGACCTTGGACCTAGGGGGA
GCCTCCACCCAAATCACGTTCCTGCCCCAGTTTGAGAAAACTCTGGAACAAACTCCT
AGGGGCTACCTCACTTCCTTTGAGATGTTTAACAGCACTTATAAGCTCTATACACAT
AGTTACCTGGGATTTGGATTGAAAGCTGCAAGACTAGCAACCCTGGGAGCCCTGGA
GACAGAAGGGACTGATGGGCACACTTTCCGGAGTGCCTGTTTACCGAGATGGTTGG
AAGCAGAGTGGATCTTTGGGGGTGTGAAATACCAGTATGGTGGCAACCAAGAAGGG
GAGGTGGGCTTTGAGCCCTGCTATGCCGAAGTGCTGAGGGTGGTACGAGGAAAACT
TCACCAGCCAGAGGAGGTCCAGAGAGGTTCCTTCTATGCTTTCTCTTACTATTATGA
CCGAGCTGTTGACACAGACATGATTGATTATGAAAAGGGGGGTATTTTAAAAGTTGA
AGATTTTGAAAGAAAAGCCAGGGAAGTGTGTGATAACTTGGAAAACTTCACCTCAG
GCAGTCCTTTCCTGTGCATGGATCTCAGCTACATCACAGCCCTGTTAAAGGATGGCT
TTGGCTTTGCAGACAGCACAGTCTTACAGCTCACAAAGAAAGTGAACAACATAGAG
ACGGGCTGGGCCTTGGGGGCCACCTTTCACCTGTTGCAGTCTCTGGGCATCTCCCAT
TGAGGCCACGTACTTCCTTGGAGACCTGCATTTGCCAACACCTTTTAAGGGGAGGA
GAGAGCACTTAGTTTCTGAACTAGTCTGGGGACATCCTGGACTTGAGCCTAGAGATT
WRGTTAATTAASCGGCCGAGCTTATCCTTWATRAGGTAATTTACTTGCMTGGCCGCG
TTTACACGTCGTGATGGNAAACCTGCGTCCCAACTAACGCTTGASAMATCCCCTTCG
CAGCTGCGATACCAAAAGCCGACGACGCCTTCCACAGTGCCA

Figure 1

SEQ ID NO:3:
MATSWGTVFFMLVVSCVCSAVSHRNQQTWFEGIFLSSMCPINVSASTLYGIMFDAGSTG
TRIHVYTFVQKMPGQLPILEGEVFDSVKPGLSAFVDQPKQGAETVQGLLEVAKDSIPRSH
WKKTPVVLKATAGLRLLPEHKAKALLFEVKEIFRKSPFLVPKGSVSIMDGSDEGILAWV
TVNFLTGQLHGHRQETVGTLDLGGASTQITFLPQFEKTLEQTPRGYLTSFEMFNSTYKLY
THSYLGFGLKAARLATLGALETEGTDGHTFRSACLPRWLEAEWIFGGVKYQYGGNQEG
EVGFEPCYAEVLRVVRGKLHQPEEVQRGSFYAFSYYYDRAVDTDMIDYEKGGILKVED
FERKAREVCDNLENFTSGSPFLCMDLSYITALLKDGFGFADSTVLQLTKKVNNIETGWA
LGATFHLLQSLGISH

Nucleotide sequence of the CD39-L4 mutant ACRIII (SEQ ID NO:6).
The nucleotide changes have been highlighted. The G to A and A to
C changes at positions 502 and 503 produce a Thr, the T to C, C
to A and C to A changes at positions 508-510 result in a Gln and
the A to C changed at position 525 result in a Phe.

ATGGCCACTTCTTGGGGCACAGTCTTTTTCATGCTGGTGGTATCCTGTGTTTGCAGCGCTGTCT
CCCACAGGAACCAGCAGACTTGGTTTGAGGGTATCTTCCTGTCTTCCATGTGCCCCATCAATGT
CAGCGCCAGCACCTTGTATGGAATTATGTTTGATGCAGGGAGCACTGGAACTCGAATTCATGTT
TACACCTTTGTGCAGAAAATGCCAGGACAGCTTCCAATTCTAGAAGGGGAAGTTTTTGATTCTG
TGAAGCCAGGACTTTCTGCTTTTGTAGATCAACCTAAGCAGGGTGCTGAGACCGTTCAAGGGCT
CTTAGAGGTGGCCAAAGACTCAATCCCCCGAAGTCACTGGAAAAAGACCCCAGTGGTCCTAAAG
GCAACAGCAGGACTACGCTTACTGCCAGAACACAAAGCCAAGGCTCTGCTCTTTGAGGTAAAGG
AGATCTTCAGGAAGTCACCTTTCCTGGTACCAAAGGGCAGTGTTAGCATCATGACTGGACAAGA
CGAAGGCATATTCGCTTGGGTTACTGTGAATTTTCTGACAGGTCAGCTGCATGGCCACAGACAG
GAGACTGTGGGGACCTTGGACCTAGGGGGAGCCTCCACCCAAATCACGTTCCTGCCCCAGTTTG
AGAAAACTCTGGAACAAACTCCTAGGGGCTACCTCACTTCCTTTGAGATGTTTAACAGCACTTA
TAAGCTCTATACACATAGTTACCTGGGATTTGGATTGAAAGCTGCAAGACTAGCAACCCTGGGA
GCCCTGGAGACAGAAGGGACTGATGGGCACACTTTCCGGAGTGCCTGTTTACCGAGATGGTTGG
AAGCAGAGTGGATCTTTGGGGGTGTGAAATACCAGTATGGTGGCAACCAAGAAGGGGAGGTGGG
CTTTGAGCCCTGCTATGCCGAAGTGCTGAGGGTGGTACGAGGAAAACTTCACCAGCCAGAGGAG
GTCCAGAGAGGTTCCTTCTATGCTTTCTCTTACTATTATGACCGAGCTGTTGACACAGACATGA
TTGATTATGAAAAGGGGGGTATTTTAAAAGTTGAAGATTTTGAAAGAAAAGCCAGGGAAGTGTG
TGATAACTTGGAAAACTTCACC TCAGGCAGTCCTTTCCTGTGCATGGATCTCAGCTACATCAC
AGCCCTGTTA AAGGATGGCTTTGGCTTTGCAGACAGCACAGTCTTACAGCTCACAAAGAAAGT
GAAC AACATAG AGACGGGCTGGGCCTTGGGGGCCACCTTTCACCTGTTGCAGTCTCTGGGCA
TCTCCCATTGA

Amino acid sequence of CD39-L4 mutant ACR III (SEQ ID NO:7). The
amino acid changes are D to T (a.a. 168), S to Q (a.a. 170), and L
to F (a.a. 175). The changes are shown in bold.

MATSYGTVFFMLVVSCVCSAVSHRNQQTWFEGIFLSSMCPINVSASTLYGIMFDAGSTGT
RIHVYTFVQKMPGQLPILEGEVFDSVKPGLSAFVDQPKQGAETVQGLLEVAKDSIPRSHW
KKTPVVLKATAGLRLLPEHKAKALLFEVKEIFRKSPFLVPKGSVSIMTGQDEGIFAWVTV
NFLTGQLHGHRQETVGTLDLGGASTQITFLPQFEKTLEQTPRGYLTSFEMFNSTYKLYTH
SYLGFGLKAARLATLGALETEGTDGHTFRSACLPRWLEAEWIFGGVKYQYGGNQEGEVGF
EPCYAEVLRVVRGKLHQPEEVQRGSFYAFSYYYDRAVDTDMIDYEKGGILKVEDFERKAR
EVCDNLENFTSGSPFLCMDLSYITALLKDGFGFADSTVLQLTKKVNNIETGWALGATFHL
LQSLGISH

FIG. 6

SEQUENCE LISTING

```
<160> NUMBER OF SEQ ID NOS: 23

<210> SEQ ID NO 1
<211> LENGTH: 300
<212> TYPE: DNA
<213> ORGANISM: Homo sapiens

<400> SEQUENCE: 1
ggcatattag cttgggttac tgtgaatttt ctgacaggtc agctgcatgg ccacagacag      60
gagactgtgg ggaccttgga cctaggggga gcctccaccc aaatcacgtt cctgccccag    120
tttgagaaaa ctctggaaca aactcctagg ggctacctca cttcctttga gatgtttaac    180
agcacttata agctctatac acatagttac ctgggatttg gattgaaagc tgcaagacta    240
gcaaccctgg gagccctgga gacagaaggg actgatgggc acactttccg gagtgcctgt    300

<210> SEQ ID NO 2
<211> LENGTH: 1799
<212> TYPE: DNA
<213> ORGANISM: Homo sapiens
<220> FEATURE:
<221> NAME/KEY: CDS
<222> LOCATION: (246)..(1529)
<221> NAME/KEY: misc_feature
<222> LOCATION: (1718)
<223> OTHER INFORMATION: n = adenine or guanine or cytosine or thymine

<400> SEQUENCE: 2
gcgggctgcc gcgcaagggt ggcgcgcgcg cgttttcctt gttcctggtc aacaaagaaa      60
tgtggagtgt cttggctgaa tcctcataca gacaagatca ttatggtgct gttaggttga    120
```

-continued

```
aaaagtgata taataaagga accaaggaga aaattcagaa ggaaagaaaa aattgcctct      180
gcaggtgtgc gagcaggatt gcttctgcaa caaaagcctc cacccagcca catcttggga      240 aaaga atg gcc act tct tgg ggc aca gtc ttt ttc atg ctg gtg gta tcc     290
      Met Ala Thr Ser Trp Gly Thr Val Phe Phe Met Leu Val Val Ser
       1               5                  10                  15 tgt gtt tgc agc gct gtc tcc cac agg aac cag cag act tgg ttt gag       338
Cys Val Cys Ser Ala Val Ser His Arg Asn Gln Gln Thr Trp Phe Glu
             20                  25                  30 ggt atc ttc ctg tct tcc atg tgc ccc atc aat gtc agc gcc agc acc       386
Gly Ile Phe Leu Ser Ser Met Cys Pro Ile Asn Val Ser Ala Ser Thr
                 35                  40                  45 ttg tat gga att atg ttt gat gca ggg agc act gga act cga att cat       434
Leu Tyr Gly Ile Met Phe Asp Ala Gly Ser Thr Gly Thr Arg Ile His
         50                  55                  60 gtt tac acc ttt gtg cag aaa atg cca gga cag ctt cca att cta gaa       482
Val Tyr Thr Phe Val Gln Lys Met Pro Gly Gln Leu Pro Ile Leu Glu
 65                  70                  75 ggg gaa gtt ttt gat tct gtg aag cca gga ctt tct gct ttt gta gat       530
Gly Glu Val Phe Asp Ser Val Lys Pro Gly Leu Ser Ala Phe Val Asp
 80                  85                  90                  95 caa cct aag cag ggt gct gag acc gtt caa ggg ctc tta gag gtg gcc       578
Gln Pro Lys Gln Gly Ala Glu Thr Val Gln Gly Leu Leu Glu Val Ala
                100                 105                 110 aaa gac tca atc ccc cga agt cac tgg aaa aag acc cca gtg gtc cta       626
Lys Asp Ser Ile Pro Arg Ser His Trp Lys Lys Thr Pro Val Val Leu
                115                 120                 125 aag gca aca gca gga cta cgc tta ctg cca gaa cac aaa gcc aag gct       674
Lys Ala Thr Ala Gly Leu Arg Leu Leu Pro Glu His Lys Ala Lys Ala
            130                 135                 140 ctg ctc ttt gag gta aag gag atc ttc agg aag tca cct ttc ctg gta       722
Leu Leu Phe Glu Val Lys Glu Ile Phe Arg Lys Ser Pro Phe Leu Val
        145                 150                 155 cca aag ggc agt gtt agc atc atg gat gga tcc gac gaa ggc ata tta       770
Pro Lys Gly Ser Val Ser Ile Met Asp Gly Ser Asp Glu Gly Ile Leu
160                 165                 170                 175 gct tgg gtt act gtg aat ttt ctg aca ggt cag ctg cat ggc cac aga       818
Ala Trp Val Thr Val Asn Phe Leu Thr Gly Gln Leu His Gly His Arg
                180                 185                 190 cag gag act gtg ggg acc ttg gac cta ggg gga gcc tcc acc caa atc       866
Gln Glu Thr Val Gly Thr Leu Asp Leu Gly Gly Ala Ser Thr Gln Ile
                195                 200                 205 acg ttc ctg ccc cag ttt gag aaa act ctg gaa caa act cct agg ggc       914
Thr Phe Leu Pro Gln Phe Glu Lys Thr Leu Glu Gln Thr Pro Arg Gly
            210                 215                 220 tac ctc act tcc ttt gag atg ttt aac agc act tat aag ctc tat aca       962
Tyr Leu Thr Ser Phe Glu Met Phe Asn Ser Thr Tyr Lys Leu Tyr Thr
225                 230                 235 cat agt tac ctg gga ttt gga ttg aaa gct gca aga cta gca acc ctg       1010
His Ser Tyr Leu Gly Phe Gly Leu Lys Ala Ala Arg Leu Ala Thr Leu
240                 245                 250                 255 gga gcc ctg gag aca gaa ggg act gat ggg cac act ttc cgg agt gcc       1058
Gly Ala Leu Glu Thr Glu Gly Thr Asp Gly His Thr Phe Arg Ser Ala
                260                 265                 270 tgt tta ccg aga tgg ttg gaa gca gag tgg atc ttt ggg ggt gtg aaa       1106
Cys Leu Pro Arg Trp Leu Glu Ala Glu Trp Ile Phe Gly Gly Val Lys
            275                 280                 285 tac cag tat ggt ggc aac caa gaa ggg gag gtg ggc ttt gag ccc tgc       1154
Tyr Gln Tyr Gly Gly Asn Gln Glu Gly Glu Val Gly Phe Glu Pro Cys
        290                 295                 300
```

| | | | | | | | | | | | | |
|---|---|---|---|---|---|---|---|---|---|---|---|---|
| tat | gcc | gaa | gtg | ctg | agg | gtg | gta | cga | gga | aaa | ctt | cac | cag | cca | gag | 1202 |
| Tyr | Ala | Glu | Val | Leu | Arg | Val | Val | Arg | Gly | Lys | Leu | His | Gln | Pro | Glu | |
| | | 305 | | | | 310 | | | | 315 | | | | | | |

```
tat gcc gaa gtg ctg agg gtg gta cga gga aaa ctt cac cag cca gag    1202
Tyr Ala Glu Val Leu Arg Val Val Arg Gly Lys Leu His Gln Pro Glu
    305                 310                 315 gag gtc cag aga ggt tcc ttc tat gct ttc tct tac tat tat gac cga    1250
Glu Val Gln Arg Gly Ser Phe Tyr Ala Phe Ser Tyr Tyr Tyr Asp Arg
320                 325                 330                 335 gct gtt gac aca gac atg att gat tat gaa aag ggg ggt att tta aaa    1298
Ala Val Asp Thr Asp Met Ile Asp Tyr Glu Lys Gly Gly Ile Leu Lys
                340                 345                 350 gtt gaa gat ttt gaa aga aaa gcc agg gaa gtg tgt gat aac ttg gaa    1346
Val Glu Asp Phe Glu Arg Lys Ala Arg Glu Val Cys Asp Asn Leu Glu
            355                 360                 365 aac ttc acc tca ggc agt cct ttc ctg tgc atg gat ctc agc tac atc    1394
Asn Phe Thr Ser Gly Ser Pro Phe Leu Cys Met Asp Leu Ser Tyr Ile
        370                 375                 380 aca gcc ctg tta aag gat ggc ttt ggc ttt gca gac agc aca gtc tta    1442
Thr Ala Leu Leu Lys Asp Gly Phe Gly Phe Ala Asp Ser Thr Val Leu
    385                 390                 395 cag ctc aca aag aaa gtg aac aac ata gag acg ggc tgg gcc ttg ggg    1490
Gln Leu Thr Lys Lys Val Asn Asn Ile Glu Thr Gly Trp Ala Leu Gly
400                 405                 410                 415 gcc acc ttt cac ctg ttg cag tct ctg ggc atc tcc cat tgaggccacg    1539
Ala Thr Phe His Leu Leu Gln Ser Leu Gly Ile Ser His
                420                 425 tacttccttg gagacctgca tttgccaaca ccttttttaag gggaggagag agcacttagt    1599
ttctgaacta gtctggggac atcctggact tgagcctaga gattwrgtta attaascggc    1659
cgagcttatc cttwatragg taatttactt gcmtggccgc gtttacacgt cgtgatggna    1719
aacctgcgtc ccaactaacg cttgasamat ccccttcgca gctgcgatac caaaagccga    1779
cgacgccttc cacagtgcca                                                1799

<210> SEQ ID NO 3
<211> LENGTH: 428
<212> TYPE: PRT
<213> ORGANISM: Homo sapiens

<400> SEQUENCE: 3

Met Ala Thr Ser Trp Gly Thr Val Phe Phe Met Leu Val Val Ser Cys
1               5                   10                  15

Val Cys Ser Ala Val Ser His Arg Asn Gln Gln Thr Trp Phe Glu Gly
            20                  25                  30

Ile Phe Leu Ser Ser Met Cys Pro Ile Asn Val Ser Ala Ser Thr Leu
        35                  40                  45

Tyr Gly Ile Met Phe Asp Ala Gly Ser Thr Gly Thr Arg Ile His Val
    50                  55                  60

Tyr Thr Phe Val Gln Lys Met Pro Gly Gln Leu Pro Ile Leu Glu Gly
65                  70                  75                  80

Glu Val Phe Asp Ser Val Lys Pro Gly Leu Ser Ala Phe Val Asp Gln
                85                  90                  95

Pro Lys Gln Gly Ala Glu Thr Val Gln Gly Leu Leu Glu Val Ala Lys
            100                 105                 110

Asp Ser Ile Pro Arg Ser His Trp Lys Lys Thr Pro Val Val Leu Lys
        115                 120                 125

Ala Thr Ala Gly Leu Arg Leu Leu Pro Glu His Lys Ala Lys Ala Leu
    130                 135                 140

Leu Phe Glu Val Lys Glu Ile Phe Arg Lys Ser Pro Phe Leu Val Pro
```

-continued

```
            145                 150                 155                 160
        Lys Gly Ser Val Ser Ile Met Asp Gly Ser Asp Glu Gly Ile Leu Ala
                        165                 170                 175

Trp Val Thr Val Asn Phe Leu Thr Gly Gln Leu His Gly His Arg Gln
                        180                 185                 190

Glu Thr Val Gly Thr Leu Asp Leu Gly Gly Ala Ser Thr Gln Ile Thr
                        195                 200                 205

Phe Leu Pro Gln Phe Glu Lys Thr Leu Glu Gln Thr Pro Arg Gly Tyr
                        210                 215                 220

Leu Thr Ser Phe Glu Met Phe Asn Ser Thr Tyr Lys Leu Tyr Thr His
        225                 230                 235                 240

Ser Tyr Leu Gly Phe Gly Leu Lys Ala Ala Arg Leu Ala Thr Leu Gly
                        245                 250                 255

Ala Leu Glu Thr Glu Gly Thr Asp Gly His Thr Phe Arg Ser Ala Cys
                        260                 265                 270

Leu Pro Arg Trp Leu Glu Ala Glu Trp Ile Phe Gly Gly Val Lys Tyr
                        275                 280                 285

Gln Tyr Gly Gly Asn Gln Glu Gly Glu Val Gly Phe Glu Pro Cys Tyr
                        290                 295                 300

Ala Glu Val Leu Arg Val Val Arg Gly Lys Leu His Gln Pro Glu Glu
        305                 310                 315                 320

Val Gln Arg Gly Ser Phe Tyr Ala Phe Ser Tyr Tyr Asp Arg Ala
                        325                 330                 335

Val Asp Thr Asp Met Ile Asp Tyr Glu Lys Gly Gly Ile Leu Lys Val
                        340                 345                 350

Glu Asp Phe Glu Arg Lys Ala Arg Glu Val Cys Asp Asn Leu Glu Asn
                        355                 360                 365

Phe Thr Ser Gly Ser Pro Phe Leu Cys Met Asp Leu Ser Tyr Ile Thr
                        370                 375                 380

Ala Leu Leu Lys Asp Gly Phe Gly Phe Ala Asp Ser Thr Val Leu Gln
        385                 390                 395                 400

Leu Thr Lys Lys Val Asn Asn Ile Glu Thr Gly Trp Ala Leu Gly Ala
                        405                 410                 415

Thr Phe His Leu Leu Gln Ser Leu Gly Ile Ser His
                        420                 425

<210> SEQ ID NO 4
<211> LENGTH: 1287
<212> TYPE: DNA
<213> ORGANISM: Homo sapiens
<220> FEATURE:
<221> NAME/KEY: CDS
<222> LOCATION: (1)..(1284)

<400> SEQUENCE: 4 atg gcc act tct tgg ggc aca gtc ttt ttc atg ctg gtg gta tcc tgt         48
Met Ala Thr Ser Trp Gly Thr Val Phe Phe Met Leu Val Val Ser Cys
  1               5                  10                  15 gtt tgc agc gct gtc tcc cac agg aac cag cag act tgg ttt gag ggt         96
Val Cys Ser Ala Val Ser His Arg Asn Gln Gln Thr Trp Phe Glu Gly
                 20                  25                  30 atc ttc ctg tct tcc atg tgc ccc atc aat gtc agc gcc agc acc ttg        144
Ile Phe Leu Ser Ser Met Cys Pro Ile Asn Val Ser Ala Ser Thr Leu
             35                  40                  45 tat gga att atg ttt gat gca ggg agc act gga act cga att cat gtt        192
Tyr Gly Ile Met Phe Asp Ala Gly Ser Thr Gly Thr Arg Ile His Val
         50                  55                  60
```

-continued

| | | |
|---|---|---|
| tac acc ttt gtg cag aaa atg cca gga cag ctt cca att cta gaa ggg<br>Tyr Thr Phe Val Gln Lys Met Pro Gly Gln Leu Pro Ile Leu Glu Gly<br>65                             70                         75                       80 | 240 |

| | |
|---|---|
| tac acc ttt gtg cag aaa atg cca gga cag ctt cca att cta gaa ggg | 240 |
| Tyr Thr Phe Val Gln Lys Met Pro Gly Gln Leu Pro Ile Leu Glu Gly | |
| 65                  70                  75                  80 | |
| gaa gtt ttt gat tct gtg aag cca gga ctt tct gct ttt gta gat caa | 288 |
| Glu Val Phe Asp Ser Val Lys Pro Gly Leu Ser Ala Phe Val Asp Gln | |
|                 85                  90                  95 | |
| cct aag cag ggt gct gag acc gtt caa ggg ctc tta gag gtg gcc aaa | 336 |
| Pro Lys Gln Gly Ala Glu Thr Val Gln Gly Leu Leu Glu Val Ala Lys | |
|             100                 105                 110 | |
| gac tca atc ccc cga agt cac tgg aaa aag acc cca gtg gtc cta aag | 384 |
| Asp Ser Ile Pro Arg Ser His Trp Lys Lys Thr Pro Val Val Leu Lys | |
|             115                 120                 125 | |
| gca aca gca gga cta cgc tta ctg cca gaa cac aaa gcc aag gct ctg | 432 |
| Ala Thr Ala Gly Leu Arg Leu Leu Pro Glu His Lys Ala Lys Ala Leu | |
|         130                 135                 140 | |
| ctc ttt gag gta aag gag atc ttc agg aag tca cct ttc ctg gta cca | 480 |
| Leu Phe Glu Val Lys Glu Ile Phe Arg Lys Ser Pro Phe Leu Val Pro | |
| 145                 150                 155                 160 | |
| aag ggc agt gtt agc atc atg gat gga tcc gac gaa ggc ata tta gct | 528 |
| Lys Gly Ser Val Ser Ile Met Asp Gly Ser Asp Glu Gly Ile Leu Ala | |
|                 165                 170                 175 | |
| tgg gtt act gtg aat ttt ctg aca ggt cag ctg cat ggc cac aga cag | 576 |
| Trp Val Thr Val Asn Phe Leu Thr Gly Gln Leu His Gly His Arg Gln | |
|             180                 185                 190 | |
| gag act gtg ggg acc ttg gac cta ggg gga gcc tcc acc caa atc acg | 624 |
| Glu Thr Val Gly Thr Leu Asp Leu Gly Gly Ala Ser Thr Gln Ile Thr | |
|             195                 200                 205 | |
| ttc ctg ccc cag ttt gag aaa act ctg gaa caa act cct agg ggc tac | 672 |
| Phe Leu Pro Gln Phe Glu Lys Thr Leu Glu Gln Thr Pro Arg Gly Tyr | |
|         210                 215                 220 | |
| ctc act tcc ttt gag atg ttt aac agc act tat aag ctc tat aca cat | 720 |
| Leu Thr Ser Phe Glu Met Phe Asn Ser Thr Tyr Lys Leu Tyr Thr His | |
| 225                 230                 235                 240 | |
| agt tac ctg gga ttt gga ttg aaa gct gca aga cta gca acc ctg gga | 768 |
| Ser Tyr Leu Gly Phe Gly Leu Lys Ala Ala Arg Leu Ala Thr Leu Gly | |
|                 245                 250                 255 | |
| gcc ctg gag aca gaa ggg act gat ggg cac act ttc cgg agt gcc tgt | 816 |
| Ala Leu Glu Thr Glu Gly Thr Asp Gly His Thr Phe Arg Ser Ala Cys | |
|             260                 265                 270 | |
| tta ccg aga tgg ttg gaa gca gag tgg atc ttt ggg ggt gtg aaa tac | 864 |
| Leu Pro Arg Trp Leu Glu Ala Glu Trp Ile Phe Gly Gly Val Lys Tyr | |
|             275                 280                 285 | |
| cag tat ggt ggc aac caa gaa ggg gag gtg ggc ttt gag ccc tgc tat | 912 |
| Gln Tyr Gly Gly Asn Gln Glu Gly Glu Val Gly Phe Glu Pro Cys Tyr | |
|         290                 295                 300 | |
| gcc gaa gtg ctg agg gtg gta cga gga aaa ctt cac cag cca gag gag | 960 |
| Ala Glu Val Leu Arg Val Val Arg Gly Lys Leu His Gln Pro Glu Glu | |
| 305                 310                 315                 320 | |
| gtc cag aga ggt tcc ttc tat gct ttc tct tac tat tat gac cga gct | 1008 |
| Val Gln Arg Gly Ser Phe Tyr Ala Phe Ser Tyr Tyr Tyr Asp Arg Ala | |
|                 325                 330                 335 | |
| gtt gac aca gac atg att gat tat gaa aag ggg ggt att tta aaa gtt | 1056 |
| Val Asp Thr Asp Met Ile Asp Tyr Glu Lys Gly Gly Ile Leu Lys Val | |
|             340                 345                 350 | |
| gaa gat ttt gaa aga aaa gcc agg gaa gtg tgt gat aac ttg gaa aac | 1104 |
| Glu Asp Phe Glu Arg Lys Ala Arg Glu Val Cys Asp Asn Leu Glu Asn | |
|             355                 360                 365 | |
| ttc acc tca ggc agt cct ttc ctg tgc atg gat ctc agc tac atc aca | 1152 |
| Phe Thr Ser Gly Ser Pro Phe Leu Cys Met Asp Leu Ser Tyr Ile Thr | |

```
                    370                 375                 380
gcc ctg tta aag gat ggc ttt ggc ttt gca gac agc aca gtc tta cag      1200
Ala Leu Leu Lys Asp Gly Phe Gly Phe Ala Asp Ser Thr Val Leu Gln
385                 390                 395                 400 ctc aca aag aaa gtg aac aac ata gag acg ggc tgg gcc ttg ggg gcc      1248
Leu Thr Lys Lys Val Asn Asn Ile Glu Thr Gly Trp Ala Leu Gly Ala
                405                 410                 415 acc ttt cac ctg ttg cag tct ctg ggc atc tcc cat tga                  1287
Thr Phe His Leu Leu Gln Ser Leu Gly Ile Ser His
                420                 425
```

<210> SEQ ID NO 5
<211> LENGTH: 428
<212> TYPE: PRT
<213> ORGANISM: Homo sapiens

<400> SEQUENCE: 5

```
Met Ala Thr Ser Trp Gly Thr Val Phe Phe Met Leu Val Val Ser Cys
  1               5                  10                  15

Val Cys Ser Ala Val Ser His Arg Asn Gln Gln Thr Trp Phe Glu Gly
                 20                  25                  30

Ile Phe Leu Ser Ser Met Cys Pro Ile Asn Val Ser Ala Ser Thr Leu
             35                  40                  45

Tyr Gly Ile Met Phe Asp Ala Gly Ser Thr Gly Thr Arg Ile His Val
         50                  55                  60

Tyr Thr Phe Val Gln Lys Met Pro Gly Gln Leu Pro Ile Leu Glu Gly
 65                  70                  75                  80

Glu Val Phe Asp Ser Val Lys Pro Gly Leu Ser Ala Phe Val Asp Gln
                 85                  90                  95

Pro Lys Gln Gly Ala Glu Thr Val Gln Gly Leu Leu Glu Val Ala Lys
                100                 105                 110

Asp Ser Ile Pro Arg Ser His Trp Lys Lys Thr Pro Val Val Leu Lys
            115                 120                 125

Ala Thr Ala Gly Leu Arg Leu Leu Pro Glu His Lys Ala Lys Ala Leu
        130                 135                 140

Leu Phe Glu Val Lys Glu Ile Phe Arg Lys Ser Pro Phe Leu Val Pro
145                 150                 155                 160

Lys Gly Ser Val Ser Ile Met Asp Gly Ser Asp Glu Gly Ile Leu Ala
                165                 170                 175

Trp Val Thr Val Asn Phe Leu Thr Gly Gln Leu His Gly His Arg Gln
            180                 185                 190

Glu Thr Val Gly Thr Leu Asp Leu Gly Gly Ala Ser Thr Gln Ile Thr
        195                 200                 205

Phe Leu Pro Gln Phe Glu Lys Thr Leu Glu Gln Thr Pro Arg Gly Tyr
    210                 215                 220

Leu Thr Ser Phe Glu Met Phe Asn Ser Thr Tyr Lys Leu Tyr Thr His
225                 230                 235                 240

Ser Tyr Leu Gly Phe Gly Leu Lys Ala Ala Arg Leu Ala Thr Leu Gly
                245                 250                 255

Ala Leu Glu Thr Glu Gly Thr Asp Gly His Thr Phe Arg Ser Ala Cys
            260                 265                 270

Leu Pro Arg Trp Leu Glu Ala Glu Trp Ile Phe Gly Gly Val Lys Tyr
        275                 280                 285

Gln Tyr Gly Gly Asn Gln Glu Gly Glu Val Gly Phe Glu Pro Cys Tyr
    290                 295                 300
```

-continued

| | | | | | | | | | | | |
|---|---|---|---|---|---|---|---|---|---|---|---|
|Ala|Glu|Val|Leu|Arg|Val|Arg|Gly|Lys|Leu|His|Gln|Pro|Glu|Glu|
|305| | | | |310| | | | |315| | | |320|

Val Gln Arg Gly Ser Phe Tyr Ala Phe Ser Tyr Tyr Asp Arg Ala
                        325                      330                 335

Val Asp Thr Asp Met Ile Asp Tyr Glu Lys Gly Gly Ile Leu Lys Val
340                    345                  350

Glu Asp Phe Glu Arg Lys Ala Arg Glu Val Cys Asp Asn Leu Glu Asn
        355                      360                    365

Phe Thr Ser Gly Ser Pro Phe Leu Cys Met Asp Leu Ser Tyr Ile Thr
370                    375                  380

Ala Leu Leu Lys Asp Gly Phe Gly Phe Ala Asp Ser Thr Val Leu Gln
385                    390                  395                400

Leu Thr Lys Lys Val Asn Asn Ile Glu Thr Gly Trp Ala Leu Gly Ala
            405                    410                  415

Thr Phe His Leu Leu Gln Ser Leu Gly Ile Ser His
            420                    425

<210> SEQ ID NO 6
<211> LENGTH: 1287
<212> TYPE: DNA
<213> ORGANISM: Homo sapiens
<220> FEATURE:
<221> NAME/KEY: CDS
<222> LOCATION: (1)..(1284)

<400> SEQUENCE: 6

```
atg gcc act tct tgg ggc aca gtc ttt ttc atg ctg gtg gta tcc tgt      48
Met Ala Thr Ser Trp Gly Thr Val Phe Phe Met Leu Val Val Ser Cys
  1               5                  10                  15 gtt tgc agc gct gtc tcc cac agg aac cag cag act tgg ttt gag ggt      96
Val Cys Ser Ala Val Ser His Arg Asn Gln Gln Thr Trp Phe Glu Gly
             20                  25                  30 atc ttc ctg tct tcc atg tgc ccc atc aat gtc agc gcc agc acc ttg     144
Ile Phe Leu Ser Ser Met Cys Pro Ile Asn Val Ser Ala Ser Thr Leu
         35                  40                  45 tat gga att atg ttt gat gca ggg agc act gga act cga att cat gtt     192
Tyr Gly Ile Met Phe Asp Ala Gly Ser Thr Gly Thr Arg Ile His Val
     50                  55                  60 tac acc ttt gtg cag aaa atg cca gga cag ctt cca att cta gaa ggg     240
Tyr Thr Phe Val Gln Lys Met Pro Gly Gln Leu Pro Ile Leu Glu Gly
 65                  70                  75                  80 gaa gtt ttt gat tct gtg aag cca gga ctt tct gct ttt gta gat caa     288
Glu Val Phe Asp Ser Val Lys Pro Gly Leu Ser Ala Phe Val Asp Gln
                 85                  90                  95 cct aag cag ggt gct gag acc gtt caa ggg ctc tta gag gtg gcc aaa     336
Pro Lys Gln Gly Ala Glu Thr Val Gln Gly Leu Leu Glu Val Ala Lys
            100                 105                 110 gac tca atc ccc cga agt cac tgg aaa aag acc cca gtg gtc cta aag     384
Asp Ser Ile Pro Arg Ser His Trp Lys Lys Thr Pro Val Val Leu Lys
        115                 120                 125 gca aca gca gga cta cgc tta ctg cca gaa cac aaa gcc aag gct ctg     432
Ala Thr Ala Gly Leu Arg Leu Leu Pro Glu His Lys Ala Lys Ala Leu
    130                 135                 140 ctc ttt gag gta aag gag atc ttc agg aag tca cct ttc ctg gta cca     480
Leu Phe Glu Val Lys Glu Ile Phe Arg Lys Ser Pro Phe Leu Val Pro
145                 150                 155                 160 aag ggc agt gtt agc atc atg act gga caa gac gaa ggc ata ttc gct     528
Lys Gly Ser Val Ser Ile Met Thr Gly Gln Asp Glu Gly Ile Phe Ala
                165                 170                 175
```

-continued

| | | |
|---|---|---|
| tgg gtt act gtg aat ttt ctg aca ggt cag ctg cat ggc cac aga cag<br>Trp Val Thr Val Asn Phe Leu Thr Gly Gln Leu His Gly His Arg Gln<br>       180                        185                    190 | 576 |
| gag act gtg ggg acc ttg gac cta ggg gga gcc tcc acc caa atc acg<br>Glu Thr Val Gly Thr Leu Asp Leu Gly Gly Ala Ser Thr Gln Ile Thr<br>195                       200                       205 | 624 |
| ttc ctg ccc cag ttt gag aaa act ctg gaa caa act cct agg ggc tac<br>Phe Leu Pro Gln Phe Glu Lys Thr Leu Glu Gln Thr Pro Arg Gly Tyr<br>   210                      215                   220 | 672 |
| ctc act tcc ttt gag atg ttt aac agc act tat aag ctc tat aca cat<br>Leu Thr Ser Phe Glu Met Phe Asn Ser Thr Tyr Lys Leu Tyr Thr His<br>225                   230                 235               240 | 720 |
| agt tac ctg gga ttt gga ttg aaa gct gca aga cta gca acc ctg gga<br>Ser Tyr Leu Gly Phe Gly Leu Lys Ala Ala Arg Leu Ala Thr Leu Gly<br>                    245                   250               255 | 768 |
| gcc ctg gag aca gaa ggg act gat ggg cac act ttc cgg agt gcc tgt<br>Ala Leu Glu Thr Glu Gly Thr Asp Gly His Thr Phe Arg Ser Ala Cys<br>          260                     265                 270 | 816 |
| tta ccg aga tgg ttg gaa gca gag tgg atc ttt ggg ggt gtg aaa tac<br>Leu Pro Arg Trp Leu Glu Ala Glu Trp Ile Phe Gly Gly Val Lys Tyr<br>275                 280                 285 | 864 |
| cag tat ggt ggc aac caa gaa ggg gag gtg ggc ttt gag ccc tgc tat<br>Gln Tyr Gly Gly Asn Gln Glu Gly Glu Val Gly Phe Glu Pro Cys Tyr<br>   290                      295                   300 | 912 |
| gcc gaa gtg ctg agg gtg gta cga gga aaa ctt cac cag cca gag gag<br>Ala Glu Val Leu Arg Val Val Arg Gly Lys Leu His Gln Pro Glu Glu<br>305                 310                 315               320 | 960 |
| gtc cag aga ggt tcc ttc tat gct ttc tct tac tat tat gac cga gct<br>Val Gln Arg Gly Ser Phe Tyr Ala Phe Ser Tyr Tyr Tyr Asp Arg Ala<br>                    325                   330               335 | 1008 |
| gtt gac aca gac atg att gat tat gaa aag ggg ggt att tta aaa gtt<br>Val Asp Thr Asp Met Ile Asp Tyr Glu Lys Gly Gly Ile Leu Lys Val<br>          340                     345                 350 | 1056 |
| gaa gat ttt gaa aga aaa gcc agg gaa gtg tgt gat aac ttg gaa aac<br>Glu Asp Phe Glu Arg Lys Ala Arg Glu Val Cys Asp Asn Leu Glu Asn<br>355                 360                 365 | 1104 |
| ttc acc tca ggc agt cct ttc ctg tgc atg gat ctc agc tac atc aca<br>Phe Thr Ser Gly Ser Pro Phe Leu Cys Met Asp Leu Ser Tyr Ile Thr<br>   370                      375                   380 | 1152 |
| gcc ctg tta aag gat ggc ttt ggc ttt gca gac agc aca gtc tta cag<br>Ala Leu Leu Lys Asp Gly Phe Gly Phe Ala Asp Ser Thr Val Leu Gln<br>385                 390                 395               400 | 1200 |
| ctc aca aag aaa gtg aac aac ata gag acg ggc tgg gcc ttg ggg gcc<br>Leu Thr Lys Lys Val Asn Asn Ile Glu Thr Gly Trp Ala Leu Gly Ala<br>                    405                   410               415 | 1248 |
| acc ttt cac ctg ttg cag tct ctg ggc atc tcc cat tga<br>Thr Phe His Leu Leu Gln Ser Leu Gly Ile Ser His<br>          420                     425 | 1287 |

<210> SEQ ID NO 7
<211> LENGTH: 428
<212> TYPE: PRT
<213> ORGANISM: Homo sapiens

<400> SEQUENCE: 7

Met Ala Thr Ser Trp Gly Thr Val Phe Met Leu Val Val Ser Cys
1               5                   10                  15

Val Cys Ser Ala Val Ser His Arg Asn Gln Gln Thr Trp Phe Glu Gly
                20                  25                  30

Ile Phe Leu Ser Ser Met Cys Pro Ile Asn Val Ser Ala Ser Thr Leu

```
                35                  40                  45
Tyr Gly Ile Met Phe Asp Ala Gly Ser Thr Gly Thr Arg Ile His Val
 50                  55                  60
Tyr Thr Phe Val Gln Lys Met Pro Gly Gln Leu Pro Ile Leu Glu Gly
 65                  70                  75                  80
Glu Val Phe Asp Ser Val Lys Pro Gly Leu Ser Ala Phe Val Asp Gln
                 85                  90                  95
Pro Lys Gln Gly Ala Glu Thr Val Gln Gly Leu Leu Glu Val Ala Lys
                100                 105                 110
Asp Ser Ile Pro Arg Ser His Trp Lys Lys Thr Pro Val Val Leu Lys
                115                 120                 125
Ala Thr Ala Gly Leu Arg Leu Leu Pro Glu His Lys Ala Lys Ala Leu
130                 135                 140
Leu Phe Glu Val Lys Glu Ile Phe Arg Lys Ser Pro Phe Leu Val Pro
145                 150                 155                 160
Lys Gly Ser Val Ser Ile Met Thr Gly Gln Asp Glu Gly Ile Phe Ala
                165                 170                 175
Trp Val Thr Val Asn Phe Leu Thr Gly Gln Leu His Gly His Arg Gln
                180                 185                 190
Glu Thr Val Gly Thr Leu Asp Leu Gly Gly Ala Ser Thr Gln Ile Thr
                195                 200                 205
Phe Leu Pro Gln Phe Glu Lys Thr Leu Glu Gln Thr Pro Arg Gly Tyr
                210                 215                 220
Leu Thr Ser Phe Glu Met Phe Asn Ser Thr Tyr Lys Leu Tyr Thr His
225                 230                 235                 240
Ser Tyr Leu Gly Phe Gly Leu Lys Ala Ala Arg Leu Ala Thr Leu Gly
                245                 250                 255
Ala Leu Glu Thr Glu Gly Thr Asp Gly His Thr Phe Arg Ser Ala Cys
                260                 265                 270
Leu Pro Arg Trp Leu Glu Ala Glu Trp Ile Phe Gly Gly Val Lys Tyr
                275                 280                 285
Gln Tyr Gly Gly Asn Gln Glu Gly Glu Val Gly Phe Glu Pro Cys Tyr
                290                 295                 300
Ala Glu Val Leu Arg Val Val Arg Gly Lys Leu His Gln Pro Glu Glu
305                 310                 315                 320
Val Gln Arg Gly Ser Phe Tyr Ala Phe Ser Tyr Tyr Asp Arg Ala
                325                 330                 335
Val Asp Thr Asp Met Ile Asp Tyr Glu Lys Gly Gly Ile Leu Lys Val
                340                 345                 350
Glu Asp Phe Glu Arg Lys Ala Arg Glu Val Cys Asp Asn Leu Glu Asn
                355                 360                 365
Phe Thr Ser Gly Ser Pro Phe Leu Cys Met Asp Leu Ser Tyr Ile Thr
                370                 375                 380
Ala Leu Leu Lys Asp Gly Phe Gly Phe Ala Asp Ser Thr Val Leu Gln
385                 390                 395                 400
Leu Thr Lys Lys Val Asn Asn Ile Glu Thr Gly Trp Ala Leu Gly Ala
                405                 410                 415
Thr Phe His Leu Leu Gln Ser Leu Gly Ile Ser His
                420                 425

<210> SEQ ID NO 8
<211> LENGTH: 9365
<212> TYPE: DNA
<213> ORGANISM: Homo sapiens
```

```
<220> FEATURE:
<221> NAME/KEY: exon
<222> LOCATION: (1)..(288)
<221> NAME/KEY: exon
<222> LOCATION: (1281)..(1580)
<221> NAME/KEY: exon
<222> LOCATION: (1820)..(1855)
<221> NAME/KEY: exon
<222> LOCATION: (2467)..(2555)
<221> NAME/KEY: exon
<222> LOCATION: (2863)..(2942)
<221> NAME/KEY: exon
<222> LOCATION: (3889)..(3950)
<221> NAME/KEY: exon
<222> LOCATION: (4894)..(4995)
<221> NAME/KEY: exon
<222> LOCATION: (5847)..(5987)
<221> NAME/KEY: exon
<222> LOCATION: (6966)..(7138)
<221> NAME/KEY: exon
<222> LOCATION: (8556)..(9365)
<221> NAME/KEY: misc_feature
<222> LOCATION: (3409)
<223> OTHER INFORMATION: n= adenine or guanine or cytosine or thymine
<221> NAME/KEY: misc_feature
<222> LOCATION: (9214)
<223> OTHER INFORMATION: n= adenine or guanine or cytosine or thymine
<221> NAME/KEY: misc_feature
<222> LOCATION: (9303)
<223> OTHER INFORMATION: n= adenine or guanine or cytosine or thymine
<221> NAME/KEY: misc_feature
<222> LOCATION: (9311)
<223> OTHER INFORMATION: n= adenine or guanine or cytosine or thymine

<400> SEQUENCE: 8
```

| | |
|---|---|
| gcc tct gca ggt gtg cga gca gga ttg ctt ctg caa caa aag cct cca | 48 |
| ccc agc cac atc ttg gga aaa gaa tgg cca ctt ctt ggg gca cag tct | 96 |
| ttt tca tgc tgg tgg tat cct gtg ttt gca gcg ctg tct ccc aca gga | 144 |
| acc agc aga ctt ggt ttg agg gta tct tcc tgt ctt cca tgt gcc cca | 192 |
| tca atg tca gcg cca gca cct tgt atg gaa tta tgt ttg atg cag gga | 240 |
| gca ctg gaa ctc gaa ttc atg ttt aca cct ttg gca aga aaa tgc cag | 288 |
| gtaagtgcaa ctgggrccct tagtagagtc tgtaaatcca cactttagca tctcctccca | 348 |
| gaaacaaata tgctgagagt ttattatgtg aattacagaa tctcacacct agtggatgtc | 408 |
| tttcttcaga gaactttgga ctacaattga acatgtgggt tatttattta tttttattta | 468 |
| tttgttttgt ttttatttt taactttttt tttgagacaa ggtcttgctt tgttgcccgg | 528 |
| tctgtagtgc agtggcatga tgacacatca ctgcaacctt gacctcctgg gctcaagcag | 588 |
| tccttccacc tcagccccct gagttgttga gactacaggc ttgtgccacc atgcccagct | 648 |
| catttttaaa tttttttata gagacctgct cagactggcc tcaaactcct aggctcaatt | 708 |
| gatcctccca cctcagcctc ccaaagtact gggattatag gtgtaagtca ccatgcttgg | 768 |
| ccagaacaca tggcttaatt caatgtgaaa ttagaagaga gctgggctgt ctgtagtctg | 828 |
| aaacccatgt gttcaaaaag aatagttata atttgttctt cctctttaaa catgggatac | 888 |
| tccagggatc cataatattc agaatatggg gagtggtttt gggagaagga tcacatgaga | 948 |
| atttcactgc catccttgga catgaggcta ggaatccctg aagattaact ttttctgaat | 1008 |
| ttgtcagtgt ttttccttca ggtcacttat ggagcctggg gaaaggtgga ggagttaggt | 1068 |
| gtccaccaga gaaatggtag cagaaatgga ccctcagagg ttgctctagt ccttcttttcc | 1128 |
| agtactcctg caagacattc ctcacaacta ggatcattgg ggtaacttca gggaagtcat | 1188 |
| aggaaaactt acagagacag agcccagcat ctgaagcagc ctaacttttg gtaaccagct | 1248 |

```
ctctcttctg ttttgttcca tgracaaaat ag gac agc ttc caa ttc tag aag       1301
ggg aag ttt ttg att ctg tga agc cag gac ttt ctg ctt tg tag atc       1349
aac cta agc agg gtg ctg aga ccg ttc aag ggc tct tag agg tgg cca       1397
aag act caa tcc ccc gaa gtc act gga aaa aga ccc cag tgg tcc taa       1445
agg caa cag cag gac tac gct tac tgc cag aac aca aag cca agg ctc       1493
tgc tct ttg agg taa agg aga tct tca gga agt cac ctt tcc tgg tac       1541
caa agg gca gtg tta gca tca tgg atg gat ccg acg aag gtgggagagg        1590
tgttgatatg cgttccaggg ggagagggc aggatcagtg aaagatctaa ctaaaggaac      1650
tggggccagg aataaacaga aggaatgaga tagcaggaaa tagaagacag ggagaaggga     1710
acatgtgctc tagacatgga atttagagag gaaaaaaaaa aaacaaggtt ggggccagga    1770
aagagaaaaa atgctctggg atctaatcct tgtctttctt tcttttttag gca tat tag    1828
ctt ggg tta ctg tga att ttc tga cag gtaatacatc ctcaagttta             1875
tctttagagc ttaactagct tttacatgca tagtcagagg agtaaaagcc tcttctttca     1935
ttctgtattg tttcttcttc tttaaaaaag gaaaagaggc tgggtgtggc agttcatgcc     1995
tgttaattcc agcgctttgg gaggctgagt tgggcagatc acttgaggcc aggagttcaa     2055
gaccagcctg gccaacatgg cgaaactccg tctctaccaa aaatacaaaa atagctgggc     2115
atggtggtgt gtacctgtag tcccagctac tcaggaggct ggagaatcac ttgaacccag     2175
gaggcagagg ttgcagtgag ctgagagccg agattgcgcc actgcactcc aggctggatg     2235
atagagcaag actctgtctc caaaaaggcc ttccaaaaaa aaaaaaaaca cctgccttga     2295
aggcctctgc tgcaacaaga gtccttccga gttgacattc acctgcagcc ttggggctgg     2355
ggagcagtgg agtatatatg gaataccttc agtgtatgat aagagcaaga gagacaagtg     2415
ttgggctgcc caggatgtcg aggctattta gagctggctc tcatttgaca g gtc agc     2472
tgc atg gcc aca gac agg aga ctg tgg gga cct tgg acc tag ggg gag       2520
cct cca ccc aaa tca cgt tcc tgc ccc agt ttg ag g tgagtcattt           2566
aatgaagatc tggttagaag tgcacttggc aggcgtatca tggtgccaag aaagaggcgc     2626
cccattttca gccagcagct ctaccacgct taggcagagt caagtcaatt aataactagg     2686
tgaatgttcc cttgccatct cactgttcag aatcccttcg tttcctcaag cctagtgaga     2746
ttagccccct aatctgtctt catctctgat tttttgctgg gagggacggg tggtggtgtg     2806
aacatcttca ggtaattaca gatcctgaat agcttttttgc tttttctgat ttgcag aaa   2865
act ctg gaa caa amt cya trg ggc tac ctc act tcc ttt gag atg ttt       2913
aac agc act tat aag ctc tat aca cat ag g tgaggacggg gacagggaag        2963
aagaatattt mwtkttgtat gatkstyyta mctktssmaa gcwtkctcaa atctstkayt     3023
kyatctgatt mgcaaaaaca aagdctgtgc caattcccta aggcctatca actgaaaccc     3083
ggwccactta caaagccgga ggagcctaag aggcttctcc attcttggcc tcaaaagcat     3143
taatatatga cttaagagtc aaaagttttg gstggggcag tggcttcatg cctgtaatcc     3203
ctgcactttg ggaggccgag gtgggtgggc cacctgaggt caggcgtttr agaccagcct     3263
ggcaaacatg gtgaaacccc gtctytacta aaatacaaaa attagctgga tatgacagcg    3323
cacacctgta atcctagcta ttcaggaggc tgaggcagga gaatcatttg aaccctggag     3383
gcggagattg cagtgagccg agatcncacc mctgcacttc agccggagcg acagagcaag     3443
```

```
actcagtctc aaaaaaaaaa aaaaaaagaa tcaaaagctt tctgtaggga gaggacactt    3503
caagaaggct caggcaaagc tccttgccag ctcctttgag ctggccttca gaggttcaga    3563
atccagcctg gaatgtgatc ccagttgggg ctaggagcta agctaaagag agcttttctg    3623
ggaatggttc ctagwgtggg accctaggaa ttgtcactgt ctctggcctt tgaatgataa    3683
ctgtggggaa ttcttactgc atagccttga tccaaactgt gcagaaatta cccttgttg     3743
accacaggag atgaatatgt cacagacaga acaaggtttt catctttcca gagggacaca    3803
ggaacaatgt tacttttgaa agaggtagct ttaggctaga gaacttcagg accagcatga    3863
aattagtcaa tcctgtattt tacag tta cct ggg att tgg att gaa agc tgc     3915
aag act agc aac cct ggg agc cct gga gac aga ag g tttgtctggg         3961
tacctgtgct ggggggggat ggtgagggtg acacagatac tccgcttgct tcttcccttc    4021
cttgatagcc attctatgga ggaaaagatt atgttgaatt gggaggcaaa tgttgtataa    4081
tggacctaat aatggcaaac tccttttcta gtttataagt tcagaagttt tgatgtatat    4141
tattagccat ttttagaatg aggtctactt gttcaggggt aacagcctat gtctaggcag    4201
ctgaagtgtc tgcagaaatc ccaggcttta cgaatacatt cagcaggagc ttgctcaagc    4261
cctgagcttt acattggagg cacaggaagc agagtctgtt ctacatgcag gtggaacaac    4321
agagtaactc cattgatctc ttcacaggtc aggcagaact gggttcagtc ccagtgttgt    4381
gatatgaggc ragtaaccta tctgtgcccc tttcctcaca ttaaatgaga atttgcattt    4441
aaggcacttt gtacagtaat ctgttattgg gatgacatct attttgcatt tcagagtata    4501
caaaacatct tcaagtatat ttaattgaag cctctcagca accagtgagg aaggtagcat    4561
agcatttctt tcctgttttt ataaagggga aagttgctgt akgaaggtty krgatctctt    4621
wragatgtga traaagccat ggaccctct gacaaaagca catatgcatg aaaatttgct    4681
tctggtttca ggggttcac caaccccaca aagcctatct ttgaaccctg agttaaggat    4741
tcctgtcaca ggatgttgtc atggaattaa tttcatagga ttttaaggcc cagcccccat    4801
ggtgaytctt ttccacctca ctggcttctt gcttgcctcc ctccctctct ctcacttact    4861
tacctcttac cttgtgccct ggattctttc ag gga ctg atg ggc aca ctt tcc    4914
gga gtg cct gtt tac cga gat ggt tgg aag cag agt gga tct ttg ggg    4962
gtg tga aat acc agt atg gtg gca acc aag aag gcaagtgatg ttttttcact    5015
ggttaaagtt acgtttacaa tggaagctct ggaaaagtcc catgggaaac ttttccaga    5075
actcaagaga agcttatctt gttgcaggga sttattccaa agatcttggc atgcctccaa    5135
ggactaatgt gaagtgacag tgaacaaagc agctgtcatt ctgcatcagc caagtgtcat    5195
ggacccatta gatacctgcc cttagccaag tgctgtggtg cacatctatt gtcctagcta    5255
ctccaaaggt tgaggcaaga ggatcacttg agcccatgag ttcaaggcta tagtgcgcaa    5315
tgccactgca ctccagcctg gcaacaggg agacctacc tcttacaaat taattaagaa      5375
gcatattcta agcctaggtc taatgcagca gtgtgaaagc ctgtttagtt aatggttagc    5435
tatttaaatt atagtaaaac ttaaaaccaa gacaagaatg attcatcttc ttataaaagg    5495
tatatacctg aatatcaagg aatgaacctg aattcccagt gaaggaagca ggcgagccct    5555
ttagctactt gcttacaaat gctatggaat gtaatgctag gcagcagcac aaggttggcc    5615
atgatctggt gaatacagat taggcaggag agcggccatg gagaaacaga ctggtgaggc    5675
tgcagacgtt tgctcatctt tgttttgacg cctcttgtcc caagcctcag ccttctcctg    5735
cttctttgac cttcctgctg ttccctcatt gtctccagca gcctgcctca gagagtgtcc    5795
```

| | |
|---|---|
| ccttccccca gcgtcgttct caccttaccc ctgtgcacct ttgcctggca g ggg agg | 5852 |
| tgg gct ttg agc cct gct atg ccg aag tgc tga ggg tgg tac gag gaa | 5900 |
| aac ttc acc agc cag agg agg tcc aga gag gtt cct tct atg ctt tct | 5948 |
| ctt act att atg acc gag ctg ttg aca cag aca tga ttg gtgagttcac | 5997 |
| cccaggtgtc agtccagaga ggaaggtgga tagggctgtg gtggggaagg tcaaggagaa | 6057 |
| agagcacttg aggtgctttg tcggggtgat tacccacctc ttttctagtc actcgaacaa | 6117 |
| aagggtggaa atgacttaga gtcttttgga ggtgagagat gaccaaaaca actatatgag | 6177 |
| gtcttttttt ttttaacatg tttattgagg tataattggc atacaataag tgccacattt | 6237 |
| aaagtataca atttaagttt tgtcatgtat acacccatga atccatccag cacattgaag | 6297 |
| ataataaaca tatttcacca caaaaagttt cctcctgtct ctttataact tttcttctta | 6357 |
| tcacaaaagc agtgttttg cctaactgtg aaagtatatg tacctgatct gtcatggcct | 6417 |
| gagagagatg aattaatttc ctattattgt gggggttttg ttgttgttgt tgttttggtt | 6477 |
| ttttgtttgt ttgtttgttt tttgagacag agtctcactc tgttacccag gctggagtgc | 6537 |
| aatggcatga tctaggctca ctgcaacctc tgcctcccgg gttcaaccga ttctcctgcc | 6597 |
| ccagtctcct gagtagctgg gattacaggt gcctgccacc acaccgggct aattttttt | 6657 |
| ttaatagaga cgaggtttca ccatgttggt caggctggtc ttgaactcct gacctcgtta | 6717 |
| tctgccttcc tcggcctccc aaagtgctgg gattacaggc atgagccacc acacccggcc | 6777 |
| tattgtgttt tatgggtctg tttttttccat tgtggttaaa tatacataac atggaataga | 6837 |
| ttgtaaataa gtaaattagg ttgcatagat tacattatgt acatgtgtat ataatgaatg | 6897 |
| aatgaatgaa tttccttatg cttccttgaa ggcgttttga tatcagataa tcttctgttt | 6957 |
| tatttcag att atg aaa agg ggg gta ttt taa aag ttg aag att ttg aaa | 7007 |
| gaa aag cca ggg aag tgt gtg ata act tgg aaa act tca cct cag gca | 7055 |
| gtc ctt tcc tgt gca tgg atc tca gct aca tca cag ccc tgt taa agg | 7103 |
| atg gct ttg gct ttg cag aca gca cag tct tac ag g taagagacag | 7149 |
| gacaccagag tctcataaca gccctctttt gtggggttg agaaggagta agagcttgtt | 7209 |
| cagtaatcag agtagctaga agtgaaatta tgaggtattt ttgtttgggc tatggacaag | 7269 |
| gtactgtgct gggcaccatg aatgtgggaa attatctcaa tgcaatggta gcctccgagt | 7329 |
| gtattaccag gcaagctatc gcacaggtca cagaacagaa agactagcag cccaaattaa | 7389 |
| gatgccaagt cacatggttt atttatttat ttatttattt attattattt ttttgagacg | 7449 |
| gagtctygct cttgttkccy rggctggagt gcartggcry gatcwcrgct cactgcarcc | 7509 |
| tycrcctcct gggttcaagc gattctyctg cctcagcctc ccragtagct gggattacag | 7569 |
| gcrygcgcca ccacgccygg ctaatttttt tgtattttta gtagagacgg ggtttcacca | 7629 |
| tgttggccag gctrktctyr aactyctgay ctcaggtgat ccaccrcct crgcctccca | 7689 |
| aagtgctrgr attayaggyr tgagccacca ckccyrgcct ttttggktcg kttctttttt | 7749 |
| tttchttttt tttttttttt tgagacaggg tcttgctctg tcacccatgc tggagtgcag | 7809 |
| tggcatgatc tcagttcact gcaacctctg cctcccgggt tcaagtgacc ctcccacctc | 7869 |
| agccctctga gtagctggga ttacaggtgt gtgccaccac tcttgtctaa tttttttgta | 7929 |
| gagacgggt tttgccatgt tgcccaggct ggtcttgaac tcctggcctc aagcaatcca | 7989 |
| cctgccttgg cctcccaaag tgccaggagt acaggcatga gccactgcgc ctggcccat | 8049 |

```
gtttggttat tattagtgct taggaagagg cacttgctta catagtagga gttgagaagc      8109
ttggtttgtt ctttcctacc cctagatcta ttctcacctc ctgaccatgc tctttctgcc      8169
acatctatta tcattacaag ttgccttatc tgaaattagt gaatcagaaa ataaagcagg      8229
ggatactttg tgtagtttca acgttaggga aagttcagaa tactgtctgt ctaaactatc      8289
tctctagaag gcctgatggg ccacaacctg ggccagaagc attcagttca gatatgagaa      8349
tggtgggtgt aggggcaatg ccaatgggc catggccgga aggaaattgt tacagagtag       8409
tgggaagcct gcaaagactg gcttctgtcc gttttgcctt ggtttgccca tgtggatatt      8469 cttttgccaat attttctgcc caagagctgt gcttgctaga gttggaaact ggatgaaaag     8529
gtgaagactt tttttcttct caacag ctc aca aag aaa gtg aac aac ata gag       8582 acg ggc tgg gcc ttg ggg gcc acc ttt cac ctg ttg cag tct ctg ggc        8630 atc tcc cat tga ggc cac gta ctt cct tgg aga cct gca ttt gcc aac        8678 acc ttt tta agg gga gga gag agc act tag ttt ctg aac tag tct ggg        8726 gac atc ctg gac ttg agc cta gag att tag gtt taa tta att tta cac        8774 atc taa tag tga act gct gcc taa cca ctc aag agt aca cag ctg gca        8822 cca gag cat cac aga gag ccc tgt gag cca aaa agt ata gtt ttg aa         8870 ctt aac ctt gga gtg aga gcc cag gga cag gtc cct gga aac caa aga        8918 aaa atc gca ttt caa ccc ttt gag tgc ctc att cca ctg aat att taa        8966 att ttc ctc tta aat ggg aaa ctg act tat tgc aat ccc aag acc cat        9014 caa tat cag tat ttt ttt cct ccc tat aca ggg ccc tgc cca ccc tta        9062 tct gca ccc acc tcc cct gaa aaa gag aga aaa aaa aaa amc cbg gtt        9110 ttg ctt tcc wtg twt aat yca mcg acm caa aak ggg acc atg tca aaa        9158 tct gtw tga tcc tat tyt ggg tta scy cca atc agc cag ctg ara gcc        9206 ttc cta ant ttt awt agg atg ara gag tac cyc cta act gtg cat aaa        9254 ttc agc ctt aaa aaa aaa ggc acc cgg gct ttg ggg aca tgt ttg gga        9302 ngg ggg ggn tgc ctc ata tac cca cct ttg gtt taa taa cat ttt atc        9350 agc act ttg gga taa                                                    9365
```

<210> SEQ ID NO 9
<211> LENGTH: 20
<212> TYPE: DNA
<213> ORGANISM: Artificial Sequence
<220> FEATURE:
<223> OTHER INFORMATION: Description of Artificial Sequence: primer

<400> SEQUENCE: 9
gctacctcac ttcctttgag                                                  20

<210> SEQ ID NO 10
<211> LENGTH: 21
<212> TYPE: DNA
<213> ORGANISM: Artificial Sequence
<220> FEATURE:
<223> OTHER INFORMATION: Description of Artificial Sequence: primer

<400> SEQUENCE: 10
ctggctggtg aagttttcct c                                                21

<210> SEQ ID NO 11
<211> LENGTH: 21

```
<212> TYPE: DNA
<213> ORGANISM: Artificial Sequence
<220> FEATURE:
<223> OTHER INFORMATION: Description of Artificial Sequence: primer

<400> SEQUENCE: 11
gcaggtctcc aaggaagtac g                                          21

<210> SEQ ID NO 12
<211> LENGTH: 30
<212> TYPE: DNA
<213> ORGANISM: Artificial Sequence
<220> FEATURE:
<223> OTHER INFORMATION: Description of Artificial Sequence: primer

<400> SEQUENCE: 12
gtgagtgctc cctgcatcta acataattcc                                 30

<210> SEQ ID NO 13
<211> LENGTH: 45
<212> TYPE: DNA
<213> ORGANISM: Artificial Sequence
<220> FEATURE:
<223> OTHER INFORMATION: Description of Artificial Sequence: primer

<400> SEQUENCE: 13
gatgcaggga gcactcacac tagtattcat gtttacacct ttgtg                45

<210> SEQ ID NO 14
<211> LENGTH: 44
<212> TYPE: DNA
<213> ORGANISM: Artificial Sequence
<220> FEATURE:
<223> OTHER INFORMATION: Description of Artificial Sequence: primer

<400> SEQUENCE: 14
gcgtagtcct gctgttgccc ctaggtacac tggggtcttt ttcc                 44

<210> SEQ ID NO 15
<211> LENGTH: 31
<212> TYPE: DNA
<213> ORGANISM: Artificial Sequence
<220> FEATURE:
<223> OTHER INFORMATION: Description of Artificial Sequence: primer

<400> SEQUENCE: 15
gcaacagcag gactacgctt actgccagaa c                               31

<210> SEQ ID NO 16
<211> LENGTH: 48
<212> TYPE: DNA
<213> ORGANISM: Artificial Sequence
<220> FEATURE:
<223> OTHER INFORMATION: Description of Artificial Sequence: primer

<400> SEQUENCE: 16
cccaagcgaa tatgccttcg tcttgtccag tcatgatgct aacactgc             48

<210> SEQ ID NO 17
<211> LENGTH: 28
<212> TYPE: DNA
<213> ORGANISM: Artificial Sequence
<220> FEATURE:
<223> OTHER INFORMATION: Description of Artificial Sequence: primer

<400> SEQUENCE: 17
```

-continued cgaaggcata ttcgcttggg ttactgtg                                              28

<210> SEQ ID NO 18
<211> LENGTH: 22
<212> TYPE: DNA
<213> ORGANISM: Artificial Sequence
<220> FEATURE:
<223> OTHER INFORMATION: Description of Artificial Sequence: primer

<400> SEQUENCE: 18
cttccttcac tgggaattca gg                                                    22

<210> SEQ ID NO 19
<211> LENGTH: 24
<212> TYPE: DNA
<213> ORGANISM: Artificial Sequence
<220> FEATURE:
<223> OTHER INFORMATION: Description of Artificial Sequence: primer

<400> SEQUENCE: 19
ctgtttaccg agatggttgg aagc                                                  24

<210> SEQ ID NO 20
<211> LENGTH: 29
<212> TYPE: DNA
<213> ORGANISM: Artificial Sequence
<220> FEATURE:
<223> OTHER INFORMATION: Description of Artificial Sequence: primer

<400> SEQUENCE: 20
ttaaagcttg ggaaaagaat ggccacttc                                             29

<210> SEQ ID NO 21
<211> LENGTH: 29
<212> TYPE: DNA
<213> ORGANISM: Artificial Sequence
<220> FEATURE:
<223> OTHER INFORMATION: Description of Artificial Sequence: primer

<400> SEQUENCE: 21
agactcgagg tggctcaatg ggagatgcc                                             29

<210> SEQ ID NO 22
<211> LENGTH: 58
<212> TYPE: DNA
<213> ORGANISM: Artificial Sequence
<220> FEATURE:
<223> OTHER INFORMATION: Description of Artificial Sequence: primer

<400> SEQUENCE: 22
gcgctgtctc ccacagagga tcgcatcacc atcaccatca caaccagcag acttggtt            58

<210> SEQ ID NO 23
<211> LENGTH: 58
<212> TYPE: DNA
<213> ORGANISM: Artificial Sequence
<220> FEATURE:
<223> OTHER INFORMATION: Description of Artificial Sequence: primer

<400> SEQUENCE: 23
aaccaagtct gctggttgtg atggtgatgg tgatgcgatc ctctgtggga gacagcgc            58

METHODS AND MATERIALS RELATING TO NOVEL CD39-LIKE POLYPEPTIDES

1. RELATED APPLICATIONS

This patent application is a continuation of U.S. patent application Ser. No. 09/350,836 (issued as U.S. Pat. No. 6,387,645) filed Jul. 9, 1999, which is a continuation-in-part of U.S. patent application Ser. No. 09/273,447 (now abandoned) filed Mar. 19, 1999 which is a continuation-in-part of U.S. patent application Ser. No. 09/122,449 (now abandoned) filed Jul. 24, 1998 and also a continuation-in-part of U.S. patent application Ser. No. 09/244,444 (now abandoned) filed Feb. 4, 1999, which in turn is a continuation-in-part of U.S. patent application Ser. No. 09/118,205 (now abandoned) filed Jul. 16, 1998, the disclosures of all of which are incorporated by reference herein in their entirety.

2. FIELD OF THE INVENTION

This invention relates in general to novel polynucleotides isolated from cDNA libraries of human fetal liver-spleen and macrophages and to polypeptides encoded by these polynucleotides. In particular, the invention relates to a human CD39-like protein with homologies to ATP diphosphohydrolases and variants thereof.

3. BACKGROUND

CD39 (cluster of differentiation 39) is a cell-surface molecule recognized by a "cluster" of monoclonal antibodies that can be used to identify the lineage or stage of differentiation of lymphocytes and thus to distinguish one class of lymphocytes from another. This CD39 molecule was originally defined as a B lymphocyte marker (Rowe, M., et al. Int. J. Cancer 29:373 (1982)). Subsequent studies have shown CD39 to be a marker for a distinct subset of activated lymphocytes within the allosensitized CD8-positive cytotoxic cells (Gouttefangeas C., et al., Eur. J. Immunol. 22:2681 (1992)). Outside of lymphoid tissue, CD39 can be found in quiescent vascular endothelial cells (Kansas, G. S., et al., J. Immunol. 146:2235 (1991)) and throughout rat brain in the neurons of the cerebral cortex, hippocampus, and cerebellum, as well as in glial cells (Wang, T-F. and Guidotti, G., Brain Res. 790:318 (1998)).

CD39 is a 510-amino acid protein with a predicted molecular mass of 57 kDa. However, because of heavy glycosylation at asparagine residues (six potential N-glycosylation sites) the molecule displays a mobility closer to 100 kDa (Maliszewski, C. R., et al., J. Immunol. 153:3574 (1994)). CD39 contains two hydrophobic regions, one near the amino terminus and the other near the carboxyl terminus which are believed to be transmembrane regions.

Reports that several ATP Diphosphohydrolases (ATPDases) share amino acid sequence homology with CD39 have been substantiated by showing that CD39 is itself an ATPDase (Wang, T-F., et al., J. Biol. Chem. 271:9898 (1996); Kaczmarek, E., et al., J. Biol. Chem. 271:33116 (1996)). Since CD39 is a plasma membrane-bound enzyme, CD39 has been termed an "ecto-ATPase," but CD39 is more often referred to as an "ecto-apyrase" because of the reduced rate of hydrolysis of ADP when compared with ecto-ATPases.

This activity has shown to modulate platelet reactivity and aggregation in response to vascular injury. During vascular injury, activated platelets aggregate forming an occlusive thrombus. Excessive platelet accumulation at sites of vascular injury can contribute to vessel occlusion. Endothelial cells respond to the potentially occlusive effects of platelet aggregation by several mechanisms. One of these mechanisms results ecto-apyrase-mediated removal of ADP, which in turn eliminates platelet reactivity and recruitment. It is now known that the endothelial ecto-apyrase responsible for this ADP removal is CD39 (Marcus, A. J., et al., J. Clin. Invest. 99:1351 (1997)).

Recently, CD39 was engineered to produce a soluble form of the molecule. This soluble CD39 was shown to display the same nucleotidase activity as the membrane-bound molecule (Gayle, R. B., et al., J. Clin. Invest. 101:1851 (1998)). Intravenously administered soluble CD39 also remained active in mice for an extensive period of time, indicating that soluble CD39 could be useful as a inhibitor of platelet aggregation in the prophylaxis or treatment of platelet-mediated thrombotic conditions.

Platelet aggregation inhibitors (antithrombotic agents) decrease the formation or the action of chemical signals that promote platelet aggregation. Currently available antithrombotic agents include aspirin, ticlopidine, and dipyridamole. These agents have proven beneficial in the prevention and treatment of occlusive cardiovascular diseases, including myocardial infarction, cerebral ischemia, angina. Antithrombotic therapy has also been used in the maintenance of vascular grafts.

Myocardial infarction is the development of necrosis of the myocardium (the middle muscular layer of the heart wall) due to a critical imbalance between oxygen and myocardial demand. The most common cause of acute myocardium infarction is narrowing of the epicardial blood vessels due to atheromatous plaques. Plaque rupture with subsequent exposure of basement membrane results in platelet aggregation and thrombus formation, which can result in partial or complete occlusion of the vessel and subsequent myocardial ischemia.

In cerebral ischemia, inadequate blood flow results from an occlusion in a blood vessel or hemorrhaging. In the latter case, excessive bleeding in one area of the brain deprives another area of blood. If the damage occurs in a singular small area, "transient" or "focused" cerebral ischemia results. When a major artery is blocked (carotid artery) global or diffused ischemia results. The primary medical strategy for secondary prevention of stroke is antiplatelet therapy. Aspirin is currently employed for reducing the risk of recurrent transient ischemic attacks or stroke in men who have transient ischemia of the brain due to fibrin emboli.

Each year, thousands of patients suffer a decline in blood flow to one or more limbs. Without sufficient blood flow, and, unless blood flow can be restored in time, the limb must be amputated. In some cases, grafts from the patient's veins can be used to form new arteries. However, in cases where the quality of the veins is poor, polymeric vascular grafts are typically used. The polymeric grafts are inherently thrombogenic as the blood constituents passing through the grafts become activated and tend to form clots. Efforts to line the grafts with endothelial cells can reduce blood clotting, but better results are obtained when antithrombotic therapy is employed.

Angina pectoris is a characteristic chest pain caused by inadequate blood flow through the blood vessels of the myocardium. The imbalance between oxygen delivery and utilization may result from a spasm of the vascular smooth muscle or from obstruction of blood vessels caused by atherosclerotic lesions. Three classes of drugs have been shown to be effective in treating angina: nitrates, betablockers and calcium channel blockers. Currently, the antithrombotics dipyridamole and aspirin are employed to prophylactically treat angina pectoris.

Ecto-apyrases, such as CD39, offer a number of advantages over several of the standard antithrombotics. For example, aspirin treatment controls the prothrombotic action of thromboxane; however, aspirin also prevents formation of antithrombotic prostacyclin, which limits aspirin's efficacy. Another antithrombotic, endothelium-derived relaxing factor (nitric oxide; "EDRF/NO"), is inhibited in vitro and in vivo by hemoglobin after its rapid diffusion into erythrocytes. In contrast, CD39 is aspirin-insensitive and completely inhibits platelet reactivity even when eicosanoid and EDRF/NO production are blocked.

CD39's ATPDase activity also implicates CD39 in the modulation of neurotransmission. ATP is a major purinergic neurotransmitter that is often co-released into the synaptic cleft with several neurotransmitters. Responses to ATP are mediated by specific plasma membrane receptors, called P2 purinergic receptors (Dubyak, G. R. and El-Motassim, C. Am J. Physiol. 34:C577–C606 (1993)). The distribution of CD39 in the rat brain indicates that CD39 plays a role in terminating P2 purinergic neurotransmission (Wang, T. F. and Guidotti, G., Brain Res. 790:318 (1998)). Furthermore, a decrease in ecto-apyrase activity is believed to lead to an accumulation of the excitatory neurotransmitter, extracellular ATP, as well as a deficiency of the endogenous anticonvulsant extracellular adenosine.

The chomosomal localization of CD39 provides additional support for a role in modulation of neurotransmission. More specifically, CD39 has been mapped to chromosome 10q 23.1-24.1 (Maliszewski, C. R., et al., J. Immunol. 153:3574 (1994)), and this site overlaps with the susceptibility locus for human partial epilepsy with audigenic symptoms (Ottman, R. et al., Nature Genet. 10:56 (1995)). This co-localization of the CD39 gene and the susceptibility locus has led to the hypothesis that decrease in ecto-apyrase activity in the brain is the primary cause of partial epilepsy (Wang T-F., et al., Mol. Brain Res. 47:295 (1997)).

A screen for human cDNAs that hybridize to cosmids from the human chromosome 9q34 region lead to the identification of a transcript with high homology to a chicken muscle ecto-ATPase (60% identity) and the ecto-apyrase CD39 (41% amino acid identity) (Chadwick, B. P., Mamm. Genome 8:668 (1997)). This gene, designated "CD39-like-1 gene" (CD39L1), has a higher degree of homology to CD39 than does chicken muscle ecto-ATPase. The biological activity of this protein has not been tested but on the basis of the high amino acid homology, CD39L1 is believed to be a new member of the ecto-ATPase family. Recently, a mouse gene with homology to NTPases was cloned and sequenced (Acc. No. AF006482) by Chadwick et al. (Mamm. Gen. 9:162–164 (1998).)

4. SUMMARY OF THE INVENTION

The invention is based on polynucleotides isolated from cDNA libraries prepared from human fetal liver-spleen and macrophages. The compositions of the present invention include novel isolated polypeptides with apyrase and/or NDPase activity, in particular, novel human CD39-like polypeptides, and active variants thereof, isolated polynucleotides encoding such polypeptides, including recombinant DNA molecules, cloned genes or degenerative variants thereof, especially naturally occurring variants such as allelic variants, antisense polynucleotide molecules, and antibodies that specifically recognize one or more epitopes present on such polypeptides, as well as hybridomas producing such antibodies.

The compositions of the invention additionally include vectors, including expression vectors, containing the polynucleotides of the invention, cells genetically engineered to contain such polynucleotides and cells genetically engineered to express such polynucleotides.

The polynucleotides of the invention include naturally occurring or wholly or partially synthetic DNA, e.g., cDNA and genomic DNA, and RNA, e.g., mRNA. The isolated polynucleotides of the invention include a polynucleotide encoding a polypeptide comprising the amino acid sequence of SEQ ID NO. 3. The isolated polynucleotides of the invention further include a polynucleotide comprising the nucleotide sequence of SEQ ID NO. 2. The polynucleotides of the invention also include polynucleotides that encode polypeptides with a biological activity of the polypeptide of SEQ ID NO. 3 (including apyrase or NTPase activity) and that hybridize under stringent hybridization conditions to the complement of (a) the nucleotide sequence of SEQ ID NO. 2, or (b) a nucleotide sequence encoding the amino acid sequence of SEQ ID NO. 3; a polynucleotide which is an allelic variant of any polynucleotide recited above; a polypeptide which has at least 80% sequence identity to a polynucleotide of SEQ ID NO. 2; or a polynucleotide that encodes a polypeptide comprising at least one CD39-like domain, e.g. catalytic domain.

The polynucleotides of the invention additionally include the complement of any of the polynucleotides recited above.

One polynucleotide according to the invention encodes a novel CD39-like protein having the amino acid sequence shown in FIG. 2 (SEQ ID NO. 3), which has been designated CD39-L66 and is an isoform of the CD39-L4. The invention also provides a polynucleotide including a nucleotide sequence that is substantially equivalent to this polynucleotide. Polynucleotides according to the invention can have at least about 80%, more typically at least about 90%, and even more typically at least about 95%, sequence identity to a polynucleotide encoding a polypeptide including SEQ ID NO. 3.

A further aspect of the invention is the development of novel CD39-L4 variants which have improved ADPase activity compared to wild type CD39-L4 (SEQ ID NO: 5). A preferred variant, designated ACRIII herein, has the amino acid sequence set forth in SEQ ID NO: 7. The invention further provides polypeptides comprising at least one amino acid substitution selected from the group consisting of: D168→T, S170→Q and L175→F, wherein said substitution(s) result in increased ADPase activity of the polypeptide. One preferred embodiment is the polypeptide having the sequence set forth in SEQ ID NO: 7, which is a variant CD39-L4 containing all three substitutions that has been designated ACRIII. Alternatively, instead of making the specific D168→T, S170→Q and/or L175→F substitution(s), substitution of amino acids with similar properties is contemplated. Additional conservative substitutions at amino acid positions other than D168, S170 and/or L175 are further contemplated. For example, all of the corresponding amino acids from CD39 could be substituted for amino acids 167–181 of CD39-L66 or CD39-L4.

Polynucleotides encoding these variants, vectors and host cells comprising such polynucleotides, methods of using such host cells to produce polypeptides, and other therapeutic products comprising the polypeptides (including fusion proteins in which the ACRIII is fused to a heterologous peptide or polypeptide, such as an immunoglobulin constant region, or derivatives in which ACRIII is modified by water soluble polymers to increase its half-life) are also comprehended by the invention, as are methods of treating a subject suffering from a disorder relating to thrombosis, coagulation or platelet aggregation by administering such therapeutic products.

Gene therapy techniques are also provided to modulate disease states associated with CD39-L4 expression and/or biological activity. Delivery of a functional CD39-L4 gene to appropriate cells is effected ex vivo, in situ, or in vivo by use of vectors, and more particularly viral vectors (e.g., adenovirus, adeno-associated virus, or a retrovirus), or ex vivo by use of physical DNA transfer methods (e.g., liposomes or chemical treatments).

The invention also relates to methods for producing polypeptides of the invention comprising growing a culture of cells of the invention in a suitable culture medium under conditions permitting expression of the desired polypeptide, and purifying the protein from the cells or the culture medium. Preferred embodiments include those in which the protein produced by such process is a mature form of the protein.

Protein compositions of the present invention, including therapeutic compositions, comprise polypeptides of the invention and optionally an acceptable carrier, such as a hydrophilic (e.g., pharmaceutically acceptable) carrier.

Polynucleotides according to the invention have numerous applications in a variety of techniques known to those skilled in the art of molecular biology. These techniques include use as hybridization probes, use as oligomers for PCR, use for chromosome and gene mapping, use in the recombinant production of protein, and use in generation of anti-sense DNA or RNA, their chemical analogs and the like. For example, because the expression of CD39-like mRNA is largely restricted to macrophages, polynucleotides of the invention can be used as hybridization probes to detect the presence of macrophage mRNA in a sample using, e.g., in situ hybridization.

In other exemplary embodiments, the polynucleotides are used in diagnostics as expressed sequence tags for identifying expressed genes or, as well known in the art and exemplified by Vollrath et al., Science 258:52–59 (1992), as expressed sequence tags for physical mapping of the human genome.

A polynucleotide according to the invention can be joined to any of a variety of other nucleotide sequences by well-established recombinant DNA techniques (see Sambrook J et al. (1989) Molecular Cloning: A Laboratory Manual, Cold Spring Harbor Laboratory, NY). Useful nucleotide sequences for joining to polypeptides include an assortment of vectors, e.g., plasmids, cosmids, lambda phage derivatives, phagemids, and the like, that are well known in the art. Accordingly, the invention also provides a vector including a polynucleotide of the invention and a host cell containing the polynucleotide. In general, the vector contains an origin of replication functional in at least one organism, convenient restriction endonuclease sites, and a selectable marker for the host cell. Vectors according to the invention include expression vectors, replication vectors, probe generation vectors, and sequencing vectors. A host cell according to the invention can be a prokaryotic or eukaryotic cell and can be a unicellular organism or part of a multicellular organism.

The polypeptides according to the invention can be used in a variety of conventional procedures and methods that are currently applied to other proteins. For example, a polypeptide of the invention can be used to generate an antibody which specifically binds the polypeptide. The polypeptides of the invention having ATPDase activity are also useful for inhibiting platelet aggregation and can therefore be employed in the prophylaxis or treatment of pathological conditions caused by the inflammatory response. The polypeptides of the invention can also be used as molecular weight markers, and as a food supplement.

Another aspect of the invention is an antibody that specifically binds the polypeptide of the invention. Such antibodies can be either monoclonal or polyclonal antibodies, as well fragments thereof and humanized forms or fully human forms, such as those produced in transgenic animals. The invention further provides a hybridoma that produces an antibody according to the invention.

Antibodies of the invention are useful for detection and/or purification of the polypeptides of the invention.

Methods are also provided for preventing, treating or ameliorating a medical condition, including thrombotic diseases, which comprises administering to a mammalian subject, including but not limited to humans, a therapeutically effective amount of a composition comprising a polypeptide of the invention or a therapeutically effective amount of a composition comprising a binding partner of (e.g., antibody specifically reactive for) CD39-like polypeptides of the invention. The mechanics of the particular condition or pathology will dictate whether the polypeptides of the invention or binding partners (or inhibitors) of these would be beneficial to the individual in need of treatment.

The invention also provides a method of inhibiting platelet function comprising administering a CD39-L4 polypeptide of the invention to a medium comprising platelets. According to this method, polypeptides of the invention can be administered to produce an in vitro or in vivo inhibition of platelet function. A polypeptide of the invention can be administered in vivo as antithrombotic agent alone or as an adjunct to other therapies.

The invention also provides methods for detecting or quantitating the presence of the polynucleotides or polypeptides of the invention in a tissue or fluid sample, and corresponding kits that comprise suitable polynucleotide probes or antibodies, together with an optional quantitative standard. Such methods and kits can be utilized as part of prognostic and diagnostic evaluation of patients and for the identification of subjects exhibiting a predisposition to platelet mediated conditions.

The invention also provides methods for the identification of compounds that modulate (i.e. increase or decrease) the expression or activity of the polynucleotides and/or polypeptides of the invention. Such methods can be utilized, for example, for the identification of compounds and other substances that interact with (e.g., bind to) the polypeptides of the invention, and assays for identifying compounds and other substances that enhance or inhibit the activity of the polypeptides of the invention, such assays comprising the step of measuring activity of such polypeptides in the presence and absence of the test compound.

5. BRIEF DESCRIPTION OF THE DRAWINGS

FIG. 1 shows polynucleotide sequences according to the invention. SEQ ID NO:1 was obtained from the b2HFLS20W cDNA library using standard pcr, sequencing by hybridization signature analysis, and single pass gel sequencing technology. A-adenosine; C-cytosine; G-guanosine; T-thymine. Ambiguous positions are designated as follows: R indicates A or G; M indicates A or C; W indicates A or T; Y indicates C or T; S indicates C or G; K indicates G or T; V indicates A or C or G; H indicates A or C or T; D indicates A or G or T; B indicates C or G or T; and N indicates any of the four bases.

SEQ ID NO:2 is an extended version of SEQ ID NO:1 which was obtained as described in Example 34.

FIG. 2 shows an amino acid sequence corresponding to the polynucleotide sequence of SEQ ID NO:2. This sequence is designated as SEQ ID NO:3. The open reading frame encoding SEQ ID NO:3 begins at nucleotide 246 (numbered from the 5' end) of SEQ ID NO:2. A-Alanine; R-Arginine; N-Asparagine; D-Aspartic Acid; C-Cysteine; E-Glutamic Acid; Q-Glutamine; G-Glycine; H-Histidine; I-Isoleucine; L-Leucine; K-Lysine; M-Methionine; F-Phenylalanine; P-Proline; S-Serine; T-Threonine; W-Tryptophan; Y-Tyrosine; V-Valine; X- any of the twenty amino acids.

FIG. 3 shows the amino acid sequence alignment of SEQ ID NO:3 (identified as "246 prot") and human CD39 ("CD39Human.seq"). The amino acid residues are designated as for FIG. 2. The alignment was generated using the J. Hein method with the PAM250 residue weight table. Gaps are indicated by dashes; residues that are identical between the two sequences (within 1 distance unit) are boxed.

FIG. 4 shows the amino acid sequence alignment of SEQ ID NO:3 (identified as "264 prot") and murine NTPase ("mur ntpase"). The amino acid residues are designated as for FIG. 2. The alignment was generated as discussed for FIG. 3. Gaps are indicated by dashes; residues that are identical between the two sequences (within 1 distance unit) are boxed.

FIG. 5 shows the apyrase conserved regions (ACR) in CD39-L4 in bold. ACR I starts at Phe 53, ACR II starts at Pro 124 and ACR III starts at Met 167. The boxed sections highlight the amino acid substitutions that were made in the wild type CD39-L4 amino acid sequence to form mutants designated ACRI, ACRII and ACRIII.

FIG. 6 (SEQ ID NOS: 6 and 7) shows the nucleotide and corresponding amino acid sequences of a preferred ACRIII mutant containing the following substitutions in the wild type CD39-L4 amino acid sequence: D168→T, S170→Q and L175→F.

6. DETAILED DESCRIPTION

6.1 Definitions

Figure 5:
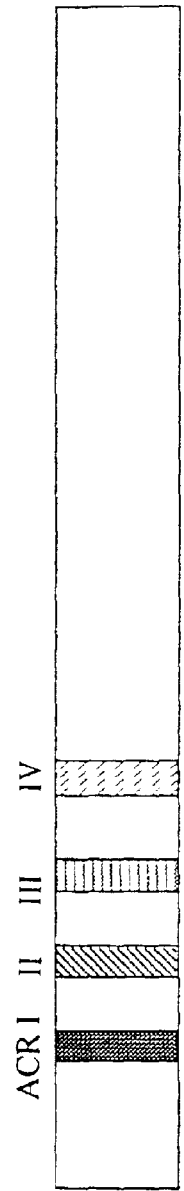

The term "nucleotide sequence" refers to a heteropolymer of nucleotides or the sequence of these nucleotides. The terms "nucleic acid" and "polynucleotide" are also used interchangeably herein to refer to a heteropolymer of nucleotides. Generally, nucleic acid segments provided by this invention may be assembled from fragments of the genome and short oligonucleotide linkers, or from a series of oligonucleotides, to provide a synthetic nucleic acid which is capable of being expressed in a recombinant transcriptional unit comprising regulatory elements derived from a microbial or viral operon.

An "oligonucleotide fragment" or a "polynucleotide fragment", "portion," or "segment" is a stretch of polypeptide nucleotide residues which is long enough to use in polymerase chain reaction (PCR) or various hybridization procedures to identify or amplify identical or related parts of mRNA or DNA molecules.

"Oligonucleotides" or "nucleic acid probes" are prepared based on the cDNA sequence provided in the present invention. Oligonucleotides comprise portions of the DNA sequence having at least about 15 nucleotides and usually at least about 20 nucleotides. Nucleic acid probes comprise portions of the sequence having fewer nucleotides than about 6 kb, usually fewer than about 1 kb. After appropriate testing to eliminate false positives, these probes may be used to determine whether mRNAs are present in a cell or tissue or to isolate similar nucleic acid sequences from chromosomal DNA as described by Walsh P S et al (1992 PCR Methods Appl 1:241–250).

The term "probes" includes naturally occurring or recombinant single- or double-stranded nucleic acids or chemically synthesized nucleic acids. They may be labeled by nick translation, Klenow fill-in reaction, PCR or other methods well known in the art. Probes of the present invention, their preparation and/or labeling are elaborated in Sambrook J et al (1989) Molecular Cloning: A Laboratory Manual, Cold Spring Harbor Laboratory, NY; or Ausubel F M et al (1989) Current Protocols in Molecular Biology, John Wiley & Sons, New York N.Y., both incorporated herein by reference.

The term "stringent" is used to refer to conditions that are commonly understood in the art as stringent. An exemplary set of conditions include a temperature of 60–70° C., (preferably about 65° C.) and a salt concentration of 0.70 M to 0.80 M (preferably about 0.75M). Further exemplary conditions include, hybridizing conditions that (1) employ low ionic strength and high temperature for washing, for example, 0.015 M NaCl/0.0015 M sodium citrate/0.1% SDS at 50(C.; (2) employ during hybridization a denaturing agent such as formamide, for example, 50% (vol/vol) formamide with 0.1% bovine serum albumin/0.1% Ficoll/0.1% polyvinylpyrrolidone/50 mM sodium phosphate buffer at pH 6.5 with 750 mM NaCl, 75 mM sodium citrate at 42(C; or (3) employ 50% formamide, 5× SSC (0.75 M NaCl, 0.075 M Sodium pyrophosphate, 5×Denhardt's solution, sonicated salmon sperm DNA (50 g/ml), 0.1% SDS, and 10% dextran sulfate at 42(C, with washes at 42(C in 0.2×SSC and 0.1% SDS.

The term "recombinant," as used herein, means that a polypeptide or protein is derived from recombinant (e.g., microbial or mammalian) expression systems. "Microbial" refers to recombinant polypeptides or proteins made in bacterial or fungal (e.g., yeast) expression systems. As a product, "recombinant microbial" defines a polypeptide or protein essentially free of native endogenous substances and unaccompanied by associated native glycosylation. Polypeptides or proteins expressed in most bacterial cultures, e.g., E. coli, will be free of glycosylation modifications; polypeptides or proteins expressed in yeast will have a glycosylation pattern different from that expressed in mammalian cells.

The term "recombinant expression vehicle or vector" refers to a plasmid or phage or virus or vector, for expressing a polypeptide from a DNA (RNA) sequence. The expression vehicle can comprise a transcriptional unit comprising an assembly of (1) a genetic element or elements having a regulatory role in gene expression, for example, promoters or enhancers, (2) a structural or coding sequence which is transcribed into mRNA and translated into protein, and (3) appropriate transcription initiation and termination sequences. Structural units intended for use in yeast or eukaryotic expression systems preferably include a leader sequence enabling extracellular secretion of translated protein by a host cell. Alternatively, where recombinant protein is expressed without a leader or transport sequence, it may include an N-terminal methionine residue. This residue may or may not be subsequently cleaved from the expressed recombinant protein to provide a final product.

"Recombinant expression system" means host cells which have stably integrated a recombinant transcriptional unit into chromosomal DNA or carry the recombinant transcriptional unit extrachromosomally. The cells can be prokaryotic or eukaryotic. Recombinant expression systems as defined herein will express heterologous polypeptides or proteins upon induction of the regulatory elements linked to the DNA segment or synthetic gene to be expressed.

The term "open reading frame," ORF, means a series of triplets coding for amino acids without any termination codons and is a sequence translatable into protein.

The term "expression modulating fragment," EMF, means a series of nucleotide molecules which modulates the expression of an operably linked ORF or EMF.

As used herein, a sequence is said to "modulate the expression of an operably linked sequence" when the expression of the sequence is altered by the presence of the EMF. EMFs include, but are not limited to, promoters, and promoter modulating sequences (inducible elements). One class of EMFs are fragments which induce the expression or an operably linked ORF in response to a specific regulatory factor or physiological event.

As used herein, an "uptake modulating fragment," UMF, means a series of nucleotide molecules which mediate the uptake of a linked DNA fragment into a cell. UMFs can be readily identified using known UMFs as a target sequence or target motif with the computer-based systems described above.

The presence and activity of a UMF can be confirmed by attaching the suspected UMF to a marker sequence. The resulting nucleic acid molecule is then incubated with an appropriate host under appropriate conditions and the uptake of the marker sequence is determined. As described above, a UMF will increase the frequency of uptake of a linked marker sequence.

"Active" refers to those forms of the polypeptide which retain the biologic and/or immunologic activities of any naturally occurring polypeptide.

"Naturally occurring polypeptide" refers to polypeptides produced by cells that have not been genetically engineered and specifically contemplates various polypeptides arising from post-translational modifications of the polypeptide including, but not limited to, acetylation, carboxylation, glycosylation, phosphorylation, lipidation and acylation.

"Derivative" refers to polypeptides chemically modified by such techniques as ubiquitination, labeling (e.g., with radionuclides or various enzymes), pegylation (derivatization with polyethylene glycol) and insertion or substitution by chemical synthesis of amino acids such as ornithine, which do not normally occur in human proteins.

"Recombinant variant" refers to any polypeptide differing from naturally occurring polypeptides by amino acid insertions, deletions, and substitutions, created using recombinant DNA techniques. Guidance in determining which amino acid residues may be replaced, added or deleted without abolishing activities of interest, such as cellular trafficking, may be found by comparing the sequence of the particular polypeptide with that of homologous peptides and minimizing the number of amino acid sequence changes made in regions of high homology.

Preferably, amino acid "substitutions" are the result of replacing one amino acid with another amino acid having similar structural and/or chemical properties, such as the replacement of a leucine with an isoleucine or valine, an aspartate with a glutamate, or a threonine with a serine, i.e., conservative amino acid replacements. "Insertions" or "deletions" are typically in the range of about 1 to 5 amino acids. The variation allowed may be experimentally determined by systematically making insertions, deletions, or substitutions of amino acids in a polypeptide molecule using recombinant DNA techniques and assaying the resulting recombinant variants for activity.

As used herein, "substantially equivalent" can refer both to nucleotide and amino acid sequences, for example a mutant sequence, that varies from a reference sequence by one or more substitutions, deletions, or additions, the net effect of which does not result in an adverse functional dissimilarity between the reference and subject sequences. Typically, such a mutant sequence varies from one of those listed herein by no more than about 20% (i.e., the number of substitutions, additions, and/or deletions in a mutant sequence, as compared to the corresponding listed sequence, divided by the total number of residues in the mutant sequence is about 0.2 or less). Such a mutant sequence is said to have 80% sequence identity to the listed sequence. In one embodiment, a mutant sequence of the invention varies from a listed sequence by no more than 10% (90% sequence identity), in a variation of this embodiment, by no more than 5% (95% sequence identity), and in a further variation of this embodiment, by no more than 2% (98% sequence identity). Mutant amino acid sequences according to the invention generally have at least 95% sequence identity with a listed amino acid sequence, whereas mutant nucleotide sequence of the invention can have lower percent sequence identities. For the purposes of the present invention, sequences having substantially equivalent biological activity and substantially equivalent expression characteristics are considered substantially equivalent. For the purposes of determining equivalence, truncation of the mature sequence should be disregarded.

Where desired, an expression vector may be designed to contain a "signal or leader sequence" which will direct the polypeptide through the membrane of a cell. Such a sequence may be naturally present on the polypeptides of the present invention or provided from heterologous protein sources by recombinant DNA techniques.

A polypeptide "fragment," "portion," or "segment" is a stretch of amino acid residues of at least about 5 amino acids, often at least about 7 amino acids, typically at least about 9 to 13 amino acids, and, in various embodiments, at least about 17 or more amino acids. To be active, any polypeptide must have sufficient length to display biologic and/or immunologic activity.

Alternatively, recombinant variants encoding these same or similar polypeptides may be synthesized or selected by making use of the "redundancy" in the genetic code. Various codon substitutions, such as the silent changes which produce various restriction sites, may be introduced to optimize cloning into a plasmid or viral vector or expression in a particular prokaryotic or eukaryotic system. Mutations in the polypeptide sequence may be reflected in the polypeptide or domains of other peptides added to the polypeptide to modify the properties of any part of the polypeptide, to change characteristics such as ligand-binding affinities, interchain affinities, or degradation/turnover rate.

"Activated" cells as used in this application are those which are engaged in extracellular or intracellular membrane trafficking, including the export of neurosecretory or enzymatic molecules as part of a normal or disease process.

The term "purified" as used herein denotes that the indicated nucleic acid or polypeptide is present in the substantial absence of other biological macromolecules, e.g., polynucleotides, proteins, and the like. In one embodiment, the polynucleotide or polypeptide is purified such that it constitutes at least 95% by weight, more preferably at least 99.8% by weight, of the indicated biological macromolecules present (but water, buffers, and other small molecules, especially molecules having a molecular weight of less than 1000 daltons, can be present).

The term "isolated" as used herein refers to a nucleic acid or polypeptide separated from at least one other component (e.g., nucleic acid or polypeptide) present with the nucleic acid or polypeptide in its natural source. In one embodiment, the nucleic acid or polypeptide is found in the presence of (if anything) only a solvent, buffer, ion, or other component normally present in a solution of the same. The terms "isolated" and "purified" do not encompass nucleic acids or polypeptides present in their natural source.

The term "infection" refers to the introduction of nucleic acids into a suitable host cell by use of a virus or viral vector.

The term "transformation" means introducing DNA into a suitable host cell so that the DNA is replicable, either as an extrachromosomal element, or by chromosomal integration.

The term "transfection" refers to the taking up of an expression vector by a suitable host cell, whether or not any coding sequences are in fact expressed.

The term "intermediate fragment" means a nucleic acid between 5 and 1000 bases in length, and preferably between 10 and 40 bp in length.

Each of the above terms is meant to encompasses all that is described for each, unless the context dictates otherwise.

6.4 Hybridization Conditions

Suitable hybridization conditions may be routinely determined by optimization procedures or pilot studies. Such procedures and studies are routinely conducted by those skilled in the art to establish protocols for use in a laboratory. See e.g., Ausubel et al., Current Protocols in Molecular Biology, Vol. 1–2, John Wiley & Sons (1989); Sambrook et al., Molecular Cloning A Laboratory Manual, 2nd Ed., Vols. 1–3, Cold Springs Harbor Press (1989); and Maniatis et al., Molecular Cloning: A Laboratory Manual, Cold Spring Harbor Laboratory Cold Spring Harbor, N.Y. (1982), all of which are incorporated by reference herein. For example, conditions such as temperature, concentration of components, hybridization and washing times, buffer components, and their pH and ionic strength may be varied.

6.7 Nucleic Acids of the Invention

The sequences falling within the scope of the present invention are not limited to the specific sequences herein described, but also include allelic variations thereof. Allelic variations can be routinely determined by comparing the sequence provided in SEQ ID NOs:1–2, a representative fragment thereof, or a nucleotide sequence at least 99.9% identical to SEQ ID NO:1–2 with a sequence from another isolate of the same species. Furthermore, to accommodate codon variability, the invention includes nucleic acid molecules coding for the same amino acid sequences as do the specific ORFs disclosed herein. In other words, in the coding region of an ORF, substitution of one codon for another which encodes the same amino acid is expressly contemplated.

Any specific sequence disclosed herein can be readily screened for errors by resequencing a particular fragment, such as an ORF, in both directions (i.e., sequence both strands).

The present invention further provides recombinant constructs comprising a nucleic acid having the sequence of any one of SEQ ID NOs:1–2 or a fragment thereof. The recombinant constructs of the present invention comprise a vector, such as a plasmid or viral vector, into which a nucleic acid having the sequence of any one of SEQ ID NOs 1–2 or a fragment thereof is inserted, in a forward or reverse orientation. In the case of a vector comprising one of the ORFs of the present invention, the vector may further comprise regulatory sequences, including for example, a promoter, operably linked to the ORF. For vectors comprising the EMFs and UMFs of the present invention, the vector may further comprise a marker sequence or heterologous ORF operably linked to the EMF or UMF. Large numbers of suitable vectors and promoters are known to those of skill in the art and are commercially available for generating the recombinant constructs of the present invention. The following vectors are provided by way of example. Bacterial: pBs, phagescript, PsiX174, pBluescript SK, pBs KS, pNH8a, pNH16a, pNH18a, pNH46a (Stratagene); pTrc99A, pKK223-3, pKK233-3, pDR540, pRIT5 (Pharmacia). Eukaryotic: pWLneo, pSV2cat, pOG44, PXTI, pSG (Stratagene) pSVK3, pBPV, pMSG, pSVL (Pharmacia).

Promoter regions can be selected from any desired gene using CAT (chloramphenicol transferase) vectors or other vectors with selectable markers. Two appropriate vectors are pKK232-8 and pCM7. Particular named bacterial promoters include lacI, lacZ, T3, T7, gpt, lambda PR, and trc. Eukaryotic promoters include CMV immediate early, HSV thymidine kinase, early and late SV40, LTRs from retrovirus, and mouse metallothionein-I. Selection of the appropriate vector and promoter is well within the level of ordinary skill in the art.

Generally, recombinant expression vectors will include origins of replication and selectable markers permitting transformation of the host cell, e.g., the ampicillin resistance gene of E. coli and S. cerevisiae TRP1 gene, and a promoter derived from a highly-expressed gene to direct transcription of a downstream structural sequence. Such promoters can be derived from operons encoding glycolytic enzymes such as 3-phosphoglycerate kinase (PGK), a-factor, acid phosphatase, or heat shock proteins, among others. The heterologous structural sequence is assembled in appropriate phase with translation initiation and termination sequences, and preferably, a leader sequence capable of directing secretion of translated protein into the periplasmic space or extracellular medium. Optionally, the heterologous sequence can encode a fusion protein including an N-terminal identification peptide imparting desired characteristics, e.g., stabilization or simplified purification of expressed recombinant product.

Useful expression vectors for bacterial use are constructed by inserting a structural DNA sequence encoding a desired protein together with suitable translation initiation and termination signals in operable reading phase with a functional promoter. The vector will comprise one or more phenotypic selectable markers and an origin of replication to ensure maintenance of the vector and to, if desirable, provide amplification within the host. Suitable prokaryotic hosts for transformation include *E. coli, Bacillus subtilis, Salmonella typhimurium* and various species within the genera *Pseudomonas, Streptomyces*, and *Staphylococcus*, although others may also be employed as a matter of choice.

As a representative but nonlimiting example, useful expression vectors for bacterial use can comprise a selectable marker and bacterial origin of replication derived from commercially available plasmids comprising genetic elements of the well known cloning vector pBR322 (ATCC 37017). Such commercial vectors include, for example, pKK223-3 (Pharmacia Fine Chemicals, Uppsala, Sweden) and GEM 1 (Promega Biotec, Madison, Wis., USA). These pBR322 "backbone" sections are combined with an appropriate promoter and the structural sequence to be expressed.

Following transformation of a suitable host strain and growth of the host strain to an appropriate cell density, the selected promoter is induced or derepressed by appropriate means (e.g., temperature shift or chemical induction) and cells are cultured for an additional period. Cells are typically harvested by centrifugation, disrupted by physical or chemical means, and the resulting crude extract retained for further purification.

Included within the scope of the nucleic acid sequences of the invention are nucleic acid sequences that hybridize under stringent conditions to a fragment of the DNA sequences in FIG. 1, which fragment is greater than about 10 bp, preferably 20–50 bp, and even greater than 100 bp.

In accordance with the invention, polynucleotide sequences which encode the novel nucleic acids, or functional equivalents thereof, may be used to generate recombinant DNA molecules that direct the expression of that nucleic acid, or a functional equivalent thereof, in appropriate host cells.

The nucleic acid sequences of the invention are further directed to sequences which encode variants of the described nucleic acids. These amino acid sequence variants may be prepared by methods known in the art by introducing appropriate nucleotide changes into a native or variant polynucleotide. There are two variables in the construction of amino acid sequence variants: the location of the mutation and the nature of the mutation. The amino acid sequence variants of the nucleic acids are preferably constructed by mutating the polynucleotide to give an amino acid sequence that does not occur in nature. These amino acid alterations can be made at sites that differ in the nucleic acids from different species (variable positions) or in highly conserved regions (constant regions). Sites at such locations will typically be modified in series, e.g., by substituting first with conservative choices (e.g., hydrophobic amino acid to a different hydrophobic amino acid) and then with more distant choices (e.g., hydrophobic amino acid to a charged amino acid), and then deletions or insertions may be made at the target site.

Amino acid sequence deletions generally range from about 1 to 30 residues, preferably about 1 to 10 residues, and are typically contiguous. Amino acid insertions include amino- and/or carboxyl-terminal fusions ranging in length from one to one hundred or more residues, as well as intrasequence insertions of single or multiple amino acid residues. Intrasequence insertions may range generally from about 1 to 10 amino residues, preferably from 1 to 5 residues. Examples of terminal insertions include the heterologous signal sequences necessary for secretion or for intracellular targeting in different host cells.

In a preferred method, polynucleotides encoding the novel nucleic acids are changed via site-directed mutagenesis. This method uses oligonucleotide sequences that encode the polynucleotide sequence of the desired amino acid variant, as well as a sufficient adjacent nucleotide on both sides of the changed amino acid to form a stable duplex on either side of the site of being changed. In general, the techniques of site-directed mutagenesis are well known to those of skill in the art and this technique is exemplified by publications such as, Edelman et al., DNA 2:183 (1983). A versatile and efficient method for producing site-specific changes in a polynucleotide sequence was published by Zoller and Smith, Nucleic Acids Res. 10:6487–6500 (1982).

PCR may also be used to create amino acid sequence variants of the novel nucleic acids. When small amounts of template DNA are used as starting material, primer(s) that differs slightly in sequence from the corresponding region in the template DNA can generate the desired amino acid variant. PCR amplification results in a population of product DNA fragments that differ from the polynucleotide template encoding the polypeptide at the position specified by the primer. The product DNA fragments replace the corresponding region in the plasmid and this gives the desired amino acid variant.

A further technique for generating amino acid variants is the cassette mutagenesis technique described in Wells et al., Gene 34:315 (1985); and other mutagenesis techniques well known in the art, such as, for example, the techniques in Sambrook et al., supra, and Current Protocols in Molecular Biology, Ausubel et al.

Due to the inherent degeneracy of the genetic code, other DNA sequences which encode substantially the same or a functionally equivalent amino acid sequence may be used in the practice of the invention for the cloning and expression of these novel nucleic acids. Such DNA sequences include those which are capable of hybridizing to the appropriate novel nucleic acid sequence under stringent conditions.

Furthermore, knowledge of the DNA sequence provided by the present invention allows for the modification of cells to permit, or increase, expression of endogenous CD39-like polypeptides. Cells can be modified (e.g., by homologous recombination) to provide increased CD39-like expression by replacing, in whole or in part, the naturally occurring CD39-like promoter with all or part of a heterologous promoter so that the cells express CD39-like polypeptides at a higher level. The heterologous promoter is inserted in such a manner that it is operatively linked to CD39-like encoding sequences. See, for example, PCT International Publication No. WO94/12650, PCT International Publication No. WO92/20808, and PCT International Publication No. WO91/09955. It is also contemplated that, in addition to heterologous promoter DNA, amplifiable marker DNA (e.g., ada, dhfr, and the multifunctional CAD gene which encodes carbamyl phosphate synthase, aspartate transcarbamylase, and dihydroorotase) and/or intron DNA may be inserted along with the heterologous promoter DNA. If linked to the CD39-like coding sequence, amplification of the marker DNA by standard selection methods results in co-amplification of the CD39-like coding sequences in the cells.

The polynucleotides of the present invention also make possible the development, through, e.g., homologous recombinantion or knock out strategies, of animals that fail to express functional CD39-L4 or that express a variant of CD39-L4. Such animals are useful as models for studying the in vivo activities of CD39-L4 as well as for studying modulators of CD39-L4.

6.8 Identification of Polymorphisms

Polymorphisms can be identified in a variety of ways known in the art which all generally involve obtaining a sample from a patient, analyzing DNA from the sample, optionally involving isolation or amplification of the DNA, and identifying the presence of the polymorphism in the DNA. For example, PCR may be used to amplify an appropriate fragment of genomic DNA which may then be sequenced. Alternatively, the DNA may be subjected to allele-specific oligonucleotide hybridization (in which appropriate oligonucleotides are hybridized to the DNA under conditions permitting detection of a single base mismatch) or to a single nucleotide extension assay (in which an oligonucleotide that hybridizes immediately adjacent to the position of the polymorphism is extended with one or more labelled nucleotides). In addition, traditional restriction fragment length polymorphism analysis (using restriction enzymes that provide differential digestion of the genomic DNA depending on the presence or absence of the polymorphism) may be performed.

Alternatively, a polymorphism resulting in a change in the amino acid sequence could also be detected by detecting a corresponding change in amino acid sequence of the protein, e.g., by an antibody specific to the variant sequence.

6.9 Hosts

The present invention further provides host cells containing SEQ ID NOs:1–2 of the present invention, wherein the nucleic acid has been introduced into the host cell using known transformation, transfection or infection methods. The host cell can be a higher eukaryotic host cell, such as a mammalian cell, a lower eukaryotic host cell, such as a yeast cell, or the host cell can be a prokaryotic cell, such as a bacterial cell. Introduction of the recombinant construct into the host cell can be effected by calcium phosphate transfection, DEAE, dextran mediated transfection, or electroporation (Davis, L. et al., Basic Methods in Molecular Biology (1986)).

The host cells containing one of SEQ ID NOs:1–2 of the present invention, can be used in conventional manners to produce the gene product encoded by the isolated fragment (in the case of an ORF) or can be used to produce a heterologous protein under the control of the EMF.

Any host/vector system can be used to express one or more of the ORFs of the present invention. These include, but are not limited to, eukaryotic hosts such as HeLa cells, Cv-1 cell, COS cells, and Sf9 cells, as well as prokaryotic host such as E. coli and B. subtilis. The most preferred cells are those which do not normally express the particular polypeptide or protein or which expresses the polypeptide or protein at low natural level.

Mature proteins can be expressed in mammalian cells, yeast, bacteria, or other cells under the control of appropriate promoters. Cell-free translation systems can also be employed to produce such proteins using RNAs derived from the DNA constructs of the present invention. Appropriate cloning and expression vectors for use with prokaryotic and eukaryotic hosts are described by Sambrook, et al., in Molecular Cloning: A Laboratory Manual, Second Edition, Cold Spring Harbor, N.Y. (1989), the disclosure of which is hereby incorporated by reference.

Various mammalian cell culture systems can also be employed to express recombinant protein. Examples of mammalian expression systems include the COS-7 lines of monkey kidney fibroblasts, described by Gluzman, Cell 23:175 (1981), and other cell lines capable of expressing a compatible vector, for example, the C127, 3T3, CHO, HeLa and BHK cell tines. Mammalian expression vectors will comprise an origin of replication, a suitable promoter and also any necessary ribosome binding sites, polyadenylation site, splice donor and acceptor sites, transcriptional termination sequences, and 5' flanking nontranscribed sequences. DNA sequences derived from the SV40 viral genome, for example, SV40 origin, early promoter, enhancer, splice, and polyadenylation sites may be used to provide the required nontranscribed genetic elements.

Recombinant polypeptides and proteins produced in bacterial culture are usually isolated by initial extraction from cell pellets, followed by one or more salting-out, aqueous ion exchange or size exclusion chromatography steps. Protein refolding steps can be used, as necessary, in completing configuration of the mature protein. Finally, high performance liquid chromatography (HPLC) can be employed for final purification steps. Microbial cells employed in expression of proteins can be disrupted by any convenient method, including freeze-thaw cycling, sonication, mechanical disruption, or use of cell lysing agents.

6.10 Peptides

The present invention further provides isolated polypeptides encoded by the nucleic acid fragments of the present invention or by degenerate variants of the nucleic acid fragments of the present invention. By "degenerate variant" is intended nucleotide fragments which differ from a nucleic acid fragment of the present invention (e.g., an ORF) by nucleotide sequence but, due to the degeneracy of the Genetic Code, encode an identical polypeptide sequence. Preferred nucleic acid fragments of the present invention are the ORFs which encode proteins.

A variety of methodologies known in the art can be utilized to obtain any one of the isolated polypeptides or proteins of the present invention. At the simplest level, the amino acid sequence can be synthesized using commercially available peptide synthesizers. This is particularly useful in producing small peptides and fragments of larger polypeptides. Fragments are useful, for example, in generating antibodies against the native polypeptide. In an alternative method, the polypeptide or protein is purified from bacterial cells which naturally produce the polypeptide or protein. One skilled in the art can readily follow known methods for isolating polypeptides and proteins in order to obtain one of the isolated polypeptides or proteins of the present invention. These include, but are not limited to, immunochromatography, HPLC, size-exclusion chromatography, ion-exchange chromatography, and immuno-affinity chromatography. See, e.g., Scopes, Protein Purification: Principles and Practice, Springer-Verlag (1994); Sambrook, et al., in Molecular Cloning: A Laboratory Manual; Ausubel et al., Current Protocols in Molecular Biology.

The polypeptides and proteins of the present invention can alternatively be purified from cells which have been altered to express the desired polypeptide or protein. As used herein, a cell is said to be altered to express a desired polypeptide or protein when the cell, through genetic manipulation, is made to produce a polypeptide or protein which it normally does not produce or which the cell normally produces at a lower level. One skilled in the art can readily adapt procedures for introducing and expressing either recombinant or synthetic sequences into eukaryotic or prokaryotic cells in order to generate a cell which produces one of the polypeptides or proteins of the present invention.

The purified polypeptides are used in in vitro binding assays which are well known in the art to identify molecules which bind to the polypeptides. These molecules include but are not limited to, for e.g., small molecules, molecules from combinatorial libraries, antibodies or other proteins. The molecules identified in the binding assay are then tested for antagonist or agonist activity in in vivo tissue culture or animal models that are well known in the art. In brief, the molecules are titrated into a plurality of cell cultures or animals and then tested for either cell/animal death or prolonged survival of the animal/cells.

In addition, the binding molecules may be complexed with toxins, e.g., ricin or cholera, or with other compounds that are toxic to cells. The toxin-binding molecule complex is then targeted to the tumor or other cell by the specificity of the binding molecule for SEQ ID NOs:3–4.

6.11 Gene Therapy

Mutations in the CD39-like gene that result in loss of normal function of the CD39-like gene product underlie CD39-related human disease states. The invention comprehends gene therapy to restore CD39-like activity that would thus be indicated in treating those disease states. Delivery of a functional CD39-like gene to appropriate cells is effected ex vivo, in situ, or in vivo by use of vectors, and more particularly viral vectors (e.g., adenovirus, adeno-associated virus, or a retrovirus), or ex vivo by use of physical DNA transfer methods (e.g., liposomes or chemical treatments). See, for example, Anderson, Nature, supplement to vol. 392, no 6679, pp. 25–30 (1998). For additional reviews of gene therapy technology, see Friedmann, Science, 244: 1275–1281 (1989); Verma, Scientific American: 68–84 (1990); and Miller, Nature, 357: 455460 (1992). Alternatively, it is contemplated that in other human disease states, preventing the expression of or inhibiting the activity of CD39-like polypeptides will be useful in treating the disease states. It is contemplated that antisense therapy or gene therapy could be applied to negatively regulate the expression of CD39-like polypeptides.

6.12 Antibodies

In general, techniques for preparing polyclonal and monoclonal antibodies as well as hybridomas capable of producing the desired antibody are well known in the art (Campbell, A. M., Monoclonal Antibodies Technology: Laboratory Techniques in Biochemistry and Molecular Biology, Elsevier Science Publishers, Amsterdam, The Netherlands (1984); St. Groth et al., J. Immunol. 35:1–21 (1990); Kohler and Milstein, Nature 256:495–497 (1975)), the trioma technique, the human B-cell hybridoma technique (Kozbor et al., Immunology Today 4:72 (1983); Cole et al., in Monoclonal Antibodies and Cancer Therapy, Alan R. Liss, Inc. (1985), pp. 77–96).

Any animal (mouse, rabbit, etc.) which is known to produce antibodies can be immunized with a peptide or polypeptide of the invention. Methods for immunization are well known in the art. Such methods include subcutaneous or intraperitoneal injection of the polypeptide. One skilled in the art will recognize that the amount of the protein encoded by the ORF of the present invention used for immunization will vary based on the animal which is immunized, the antigenicity of the peptide and the site of injection.

The protein which is used as an immunogen may be modified or administered in an adjuvant in order to increase the protein's antigenicity. Methods of increasing the antigenicity of a protein are well known in the art and include, but are not limited to, coupling the antigen with a heterologous protein (such as globulin or -galactosidase) or through the inclusion of an adjuvant during immunization.

For monoclonal antibodies, spleen cells from the immunized animals are removed, fused with myeloma cells, such as SP2/0-Ag14 myeloma cells, and allowed to become monoclonal antibody producing hybridoma cells.

Any one of a number of methods well known in the art can be used to identify the hybridoma cell which produces an antibody with the desired characteristics. These include screening the hybridomas with an ELISA assay, western blot analysis, or radioimmunoassay (Lutz et al., Exp. Cell Research. 175:109–124 (1988)).

Hybridomas secreting the desired antibodies are cloned and the class and subclass is determined using procedures known in the art (Campbell, A. M., Monoclonal Antibody Technology: Laboratory Techniques in Biochemistry and Molecular Biology, Elsevier Science Publishers, Amsterdam, The Netherlands (1984)).

Techniques described for the production of single chain antibodies (U.S. Pat. No. 4,946,778) can be adapted to produce single chain antibodies to proteins of the present invention.

For polyclonal antibodies, antibody containing antiserum is isolated from the immunized animal and is screened for the presence of antibodies with the desired specificity using one of the above-described procedures.

The present invention further provides the above-described antibodies in delectably labeled form. Antibodies can be delectably labeled through the use of radioisotopes, affinity labels (such as biotin, avidin, etc.), enzymatic labels (such as horseradish peroxidase, alkaline phosphatase, etc.) fluorescent labels (such as FITC or rhodamine, etc.), paramagnetic atoms, etc. Procedures for accomplishing such labeling are well-known in the art, for example, see (Stemberger, L. A. et al., J. Histochem. Cytochem. 18:315 (1970); Bayer, E. A. et al., Meth. Enzym. 62:308 (1979); Engval, E. et al., Immunol. 109:129 (1972); Goding, J. W. J. Immunol. Meth. 13:215 (1976)).

The labeled antibodies of the present invention can be used for in vitro, in vivo, and in situ assays to identify cells or tissues in which a fragment of the polypeptide of interest is expressed. The antibodies may also be used directly in therapies or other diagnostics.

The present invention further provides the above-described antibodies immobilized on a solid support. Examples of such solid supports include plastics such as polycarbonate, complex carbohydrates such as agarose and sepharose, acrylic resins and such as polyacrylamide and latex beads. Techniques for coupling antibodies to such solid supports are well known in the art (Weir, D. M. et al., "Handbook of Experimental Immunology" 4th Ed., Blackwell Scientific Publications, Oxford, England, Chapter 10 (1986); Jacoby, W. D. et al., Meth. Enzym. 34 Academic Press, N.Y. (1974)). The immobilized antibodies of the present invention can be used for in vitro, in vivo, and in situ assays as well as for immuno-affinity purification of the proteins of the present invention.

6.13 Computer Readable Sequences

In one application of this embodiment, a nucleotide sequence of the present invention can be recorded on computer readable media. As used herein, "computer readable media" refers to any medium which can be read and accessed directly by a computer. Such media include, but are not limited to: magnetic storage media, such as floppy discs, hard disc storage medium, and magnetic tape; optical storage media such as CD-ROM; electrical storage media such as RAM and ROM; and hybrids of these categories such as magnetic/optical storage media. A skilled artisan can readily appreciate how any of the presently known computer readable mediums can be used to create a manufacture comprising computer readable medium having recorded thereon a nucleotide sequence of the present invention.

As used herein, "recorded" refers to a process for storing information on computer readable medium. A skilled artisan can readily adopt any of the presently known methods for recording information on computer readable medium to generate manufactures comprising the nucleotide sequence information of the present invention.

A variety of data storage structures are available to a skilled artisan for creating a computer readable medium having recorded thereon a nucleotide sequence of the present invention. The choice of the data storage structure will generally be based on the means chosen to access the stored information. In addition, a variety of data processor programs and formats can be used to store the nucleotide sequence information of the present invention on computer readable medium. The sequence information can be represented in a word processing text file, formatted in commercially-available software such as WordPerfect and Microsoft Word, or represented in the form of an ASCII file, stored in a database application, such as DB2, Sybase, Oracle, or the like. A skilled artisan can readily adapt any number of dataprocessor structuring formats (e.g. text file or database) in order to obtain computer readable medium having recorded thereon the nucleotide sequence information of the present invention.

By providing the nucleotide sequence of SEQ ID NOs:1–2, a representative fragment thereof, or a nucleotide sequence at least 99.9% identical to SEQ ID NOs:1–2 in computer readable form, a skilled artisan can routinely access the sequence information for a variety of purposes. Computer software is publicly available which allows a skilled artisan to access sequence information provided in a computer readable medium. The examples which follow demonstrate how software which implements the BLAST (Altschul et al., J. Mol. Biol. 215:403–410 (1990)) and BLAZE (Brutlag et al., Comp. Chem. 17:203–207 (1993)) search algorithms on a Sybase system is used to identify open reading frames (ORFs) within a nucleic acid sequence. Such ORFs may be protein encoding fragments and may be useful in producing commercially important proteins such as enzymes used in fermentation reactions and in the production of commercially useful metabolites.

As used herein, "a computer-based system" refers to the hardware means, software means, and data storage means used to analyze the nucleotide sequence information of the present invention. The minimum hardware means of the computer-based systems of the present invention comprises a central processing unit (CPU), input means, output means, and data storage means. A skilled artisan can readily appreciate that any one of the currently available computer-based systems are suitable for use in the present invention.

As stated above, the computer-based systems of the present invention comprise a data storage means having stored therein a nucleotide sequence of the present invention and the necessary hardware means and software means for supporting and implementing a search means. As used herein, "data storage means" refers to memory which can store nucleotide sequence information of the present invention, or a memory access means which can access manufactures having recorded thereon the nucleotide sequence information of the present invention.

As used herein, "search means" refers to one or more programs which are implemented on the computer-based system to compare a target sequence or target structural motif with the sequence information stored within the data storage means. Search means are used to identify fragments or regions of a known sequence which match a particular target sequence or target motif. A variety of known algorithms are disclosed publicly and a variety of commercially available software for conducting search means are and can be used in the computer-based systems of the present invention. Examples of such software includes, but is not limited to, MacPattern (EMBL), BLASTN and BLASTA (NPOLYPEPTIDEIA). A skilled artisan can readily recognize that any one of the available algorithms or implementing software packages for conducting homology searches can be adapted for use in the present computer-based systems.

As used herein, a "target sequence" can be any nucleic acid or amino acid sequence of six or more nucleotides or two or more amino acids. A skilled artisan can readily recognize that the longer a target sequence is, the less likely a target sequence will be present as a random occurrence in the database. The most preferred sequence length of a target sequence is from about 10 to 100 amino acids or from about 30 to 300 nucleotide residues. However, it is well recognized that searches for commercially important fragments, such as sequence fragments involved in gene expression and protein processing, may be of shorter length.

As used herein, "a target structural motif," or "target motif," refers to any rationally selected sequence or combination of sequences in which the sequence(s) are chosen based on a three-dimensional configuration which is formed upon the folding of the target motif. There are a variety of target motifs known in the art. Protein target motifs include, but are not limited to, enzyme active sites and signal sequences. Nucleic acid target motifs include, but are not limited to, promoter sequences, hairpin structures and inducible expression elements (protein binding sequences).

6.14 Expression Modulating Sequences

EMF sequences can be identified within a genome by their proximity to the ORFs. An intergenic segment, or a fragment of the intergenic segment, from about 10 to 200 nucleotides in length, taken 5' from any ORF will modulate the expression of an operably linked 3' ORF in a fashion similar to that found with the naturally linked ORF sequence. As used herein, an "intergenic segment" refers to the fragments of a genome which are between two ORF(S) herein described. Alternatively, EMFs can be identified using known EMFs as a target sequence or target motif in the computer-based systems of the present invention.

The presence and activity of an EMF can be confirmed using an EMF trap vector. An EMF trap vector contains a cloning site 5' to a marker sequence. A marker sequence encodes an identifiable phenotype, such as antibiotic resistance or a complementing nutrition auxotrophic factor, which can be identified or assayed when the EMF trap vector is placed within an appropriate host under appropriate conditions. As described above, an EMF will modulate the expression of an operably linked marker sequence. A more detailed discussion of various marker sequences is provided below.

A sequence which is suspected as being an EMF is cloned in all three reading frames in one or more restriction sites upstream from the marker sequence in the EMF trap vector. The vector is then transformed into an appropriate host using known procedures and the phenotype of the transformed host is examined under appropriate conditions. As described above, an EMF will modulate the expression of an operably linked marker sequence.

6.15 Triplex Helix Formation

In addition, the fragments of the present invention, as broadly described, can be used to control gene expression through triple helix formation or antisense DNA or RNA, both of which methods are based on the binding of a polynucleotide sequence to DNA or RNA. Polynucleotides suitable for use in these methods are usually 20 to 40 bases in length and are designed to be complementary to a region of the gene involved in transcription (triple helix—see Lee et al., Nucl. Acids Res. 6:3073 (1979); Cooney et al., Science 15241:456 (1988); and Dervan et al., Science 251:1360 (1991)) or to the mRNA itself (antisense—Olmno, J. Neurochem. 56:560 (1991); Oligodeoxynucleotides as Antisense Inhibitors of Gene Expression, CRC Press, Boca Raton, Fla. (1988)).

Triple helix—formation optimally results in a shut-off of RNA transcription from DNA, while antisense RNA hybridization blocks translation of an mRNA molecule into polypeptide. Both techniques have been demonstrated to be effective in model systems. Information contained in the sequences of the present invention is necessary for the design of an antisense or triple helix oligonucleotide.

6.16 Diagnostic Assays and Kits

The present invention further provides methods to identify the expression of one of the ORFs of the present invention, or homolog thereof, in a test sample, using a nucleic acid probe or antibodies of the present invention.

In detail, such methods comprise incubating a test sample with one or more of the antibodies or one or more of nucleic acid probes of the present invention and assaying for binding of the nucleic acid probes or antibodies to components within the test sample.

Conditions for incubating a nucleic acid probe or antibody with a test sample vary. Incubation conditions depend on the format employed in the assay, the detection methods employed, and the type and nature of the nucleic acid probe or antibody used in the assay. One skilled in the art will recognize that any one of the commonly available hybridization, amplification or immunological assay formats can readily be adapted to employ the nucleic acid probes or antibodies of the present invention. Examples of such assays can be found in Chard, T., An Introduction to Radioimmunoassay and Related Techniques, Elsevier Science Publishers, Amsterdam, The Netherlands (1986); Bullock, G. R. et al., Techniques in Immunocytochemistry, Academic Press, Orlando, Fla. Vol. 1 (1982), Vol. 2 (1983), Vol. 3 (1985); Tijssen, P., Practice and Theory of immunoassays: Laboratory Techniques in Biochemistry and Molecular Biology, Elsevier Science Publishers, Amsterdam, The Netherlands (1985).

The test samples of the present invention include cells, protein or membrane extracts of cells, or biological fluids such as sputum, blood, serum, plasma, or urine. The test sample used in the above-described method will vary based on the assay format, nature of the detection method and the tissues, cells or extracts used as the sample to be assayed. Methods for preparing protein extracts or membrane extracts of cells are well known in the art and can be readily be adapted in order to obtain a sample which is compatible with the system utilized.

In another embodiment of the present invention, kits are provided which contain the necessary reagents to carry out the assays of the present invention.

Specifically, the invention provides a compartment kit to receive, in close confinement, one or more containers which comprises: (a) a first container comprising one of the probes or antibodies of the present invention; and (b) one or more other containers comprising one or more of the following: wash reagents, reagents capable of detecting presence of a bound probe or antibody.

In detail, a compartment kit includes any kit in which reagents are contained in separate containers. Such containers include small glass containers, plastic containers or strips of plastic or paper. Such containers allows one to efficiently transfer reagents from one compartment to another compartment such that the samples and reagents are not cross-contaminated, and the agents or solutions of each container can be added in a quantitative fashion from one compartment to another. Such containers will include a container which will accept the test sample, a container which contains the antibodies used in the assay, containers which contain wash reagents (such as phosphate buffered saline, Tris-buffers, etc.), and containers which contain the reagents used to detect the bound antibody or probe.

Types of detection reagents include labeled nucleic acid probes, labeled secondary antibodies, or in the alternative, if the primary antibody is labeled, the enzymatic, or antibody binding reagents which are capable of reacting with the labeled antibody. One skilled in the art will readily recognize that the disclosed probes and antibodies of the present invention can be readily incorporated into one of the established kit formats which are well known in the art.

6.17 Screening Assays

Using the isolated proteins of the present invention, the present invention further provides methods of obtaining and identifying agents which bind to a protein encoded by one of the ORFs from a nucleic acid with a sequence of one of SEQ ID NOs:1–2, or to a nucleic acid with a sequence of one of SEQ ID NOs:1–2.

In detail, said method comprises the steps of: (a) contacting an agent with an isolated protein encoded by one of the ORFs of the present invention, or nucleic acid of the invention; and (b) determining whether the agent binds to said protein or said nucleic acid.

The agents screened in the above assay can be, but are not limited to, peptides, carbohydrates, vitamin derivatives, or other pharmaceutical agents. The agents can be selected and screened at random or rationally selected or designed using protein modeling techniques.

For random screening, agents such as peptides, carbohydrates, pharmaceutical agents and the like are selected at random and are assayed for their ability to bind to the protein encoded by the ORF of the present invention.

Alternatively, agents may be rationally selected or designed. As used herein, an agent is said to be "rationally selected or designed" when the agent is chosen based on the configuration of the particular protein. For example, one skilled in the art can readily adapt currently available procedures to generate peptides, pharmaceutical agents and the like capable of binding to a specific peptide sequence in order to generate rationally designed antipeptide peptides, for example see Hurby et al., Application of Synthetic Peptides: Antisense Peptides," In Synthetic Peptides, A User's Guide, W. H. Freeman, New York (1992), pp. 289–307, and Kaspczak et al., Biochemistry 28:9230–8 (1989), or pharmaceutical agents, or the like.

In addition to the foregoing, one class of agents of the present invention, as broadly described, can be used to control gene expression through binding to one of the ORFs or EMFs of the present invention. As described above, such agents can be randomly screened or rationally designed/selected. Targeting the ORF or EMF allows a skilled artisan to design sequence specific or element specific agents, modulating the expression of either a single ORF or multiple ORFs which rely on the same EMF for expression control.

One class of DNA binding agents are agents which contain base residues which hybridize or form a triple helix formation by binding to DNA or RNA. Such agents can be based on the classic phosphodiester, ribonucleic acid backbone, or can be a variety of sulfhydryl or polymeric derivatives which have base attachment capacity.

Agents suitable for use in these methods usually contain 20 to 40 bases and are designed to be complementary to a region of the gene involved in transcription (triple helix—see Lee et al., Nucl. Acids Res. 6:3073 (1979); Cooney et al., Science 241:456 (1988); and Dervan et al., Science 251:1360 (1991)) or to the mRNA itself (antisense—Okano, J. Neurochem. 56:560 (1991); Oligodeoxynucleotides as Antisense Inhibitors of Gene Expression, CRC Press, Boca Raton, Fla. (1988)). Triple helix—formation optimally results in a shut-off of RNA transcription from DNA, while antisense RNA hybridization blocks translation of an mRNA molecule into polypeptide. Both techniques have been demonstrated to be effective in model systems. Information contained in the sequences of the present invention is necessary for the design of an antisense or triple helix oligonucleotide and other DNA binding agents.

Agents which bind to a protein encoded by one of the ORFs of the present invention can be used as a diagnostic agent, in the control of bacterial infection by modulating the activity of the protein encoded by the ORF. Agents which bind to a protein encoded by one of the ORFs of the present invention can be formulated using known techniques to generate a pharmaceutical composition.

6.18 Use of Nucleic Acids as Probes

Another aspect of the subject invention is to provide for polypeptide-specific nucleic acid hybridization probes capable of hybridizing with naturally occurring nucleotide sequences. The hybridization probes of the subject invention may be derived from the nucleotide sequence of the SEQ ID NOs:1–2. Because the corresponding gene is expressed in only one out of 18 tissues tested, namely macrophages, a hybridization probe derived from SEQ ID NOs:1–2 can be used as an indicator of the presence of macrophage RNA in a sample. Any suitable hybridization technique can be employed, such as, for example, in situ hybridization.

PCR as described U.S. Pat. Nos. 4,683,195 and 4,965,188 provides additional uses for oligonucleotides based upon the nucleotide sequences. Such probes used in PCR may be of recombinant origin, may be chemically synthesized, or a mixture of both. The probe will comprise a discrete nucleotide sequence for the detection of identical sequences or a degenerate pool of possible sequences for identification of closely related genomic sequences.

Other means for producing specific hybridization probes for nucleic acids include the cloning of nucleic acid sequences into vectors for the production of mRNA probes. Such vectors are known in the art and are commercially available and may be used to synthesize RNA probes in vitro by means of the addition of the appropriate RNA polymerase as T7 or SP6 RNA polymerase and the appropriate radioactively labeled nucleotides.

The nucleotide sequences may be used to construct hybridization probes for mapping their respective genomic sequences. The nucleotide sequence provided herein may be mapped to a chromosome or specific regions of a chromosome using well known genetic and/or chromosomal mapping techniques. These techniques include in situ hybridization, linkage analysis against known chromosomal markers, hybridization screening with libraries or flow-sorted chromosomal preparations specific to known chromosomes, and the like. The technique of fluorescent in situ hybridization of chromosome spreads has been described, among other places, in Verma et al (1988) Human Chromosomes: A Manual of Basic Techniques, Pergamon Press, New York N.Y. Fluorescent in situ hybridization of chromosomal preparations and other physical chromosome mapping techniques may be correlated with additional genetic map data. Examples of genetic map data can be found in the 1994 Genome Issue of Science (265:1981f). Correlation between the location of a nucleic acid on a physical chromosomal map and a specific disease (or predisposition to a specific disease) may help delimit the region of DNA associated with that genetic disease. The nucleotide sequences of the subject invention may be used to detect differences in gene sequences between normal, carrier or affected individuals.

The nucleotide sequence may be used to produce purified polypeptides using well known methods of recombinant DNA technology. Among the many publications that teach methods for the expression of genes after they have been isolated is Goeddel (1990) Gene Expression Technology, Methods and Enzymology, Vol 185, Academic Press, San Diego. Polypeptides may be expressed in a variety of host cells, either prokaryotic or eukaryotic. Host cells may be from the same species from which a particular polypeptide nucleotide sequence was isolated or from a different species. Advantages of producing polypeptides by recombinant DNA technology include obtaining adequate amounts of the protein for purification and the availability of simplified purification procedures.

Each sequence so obtained was compared to sequences in GenBank using a search algorithm developed by Applied Biosystems and incorporated into the INHERIT™ 670 Sequence Analysis System. In this algorithm, Pattern Specification Language (developed by TRW Inc., Los Angeles, Calif.) was used to determine regions of homology. The three parameters that determine how the sequence comparisons run were window size, window offset, and error tolerance. Using a combination of these three parameters, the DNA database was searched for sequences containing regions of homology to the query sequence, and the appropriate sequences were scored with an initial value. Subsequently, these homologous regions were examined using dot matrix homology plots to distinguish regions of homology from chance matches. Smith-Waterman alignments were used to display the results of the homology search.

Peptide and protein sequence homologies were ascertained using the INHERIT™ 670 Sequence Analysis System in a way similar to that used in DNA sequence homologies. Pattern Specification Language and parameter windows were used to search protein databases for sequences containing regions of homology which were scored with an initial value. Dot-matrix homology plots were examined to distinguish regions of significant homology from chance matches.

Alternatively, BLAST, which stands for Basic Local Alignment Search Tool, is used to search for local sequence alignments (Altschul S F (1993) J Mol Evol 36:290–300; Altschul, S F et al (1990) J Mol Biol 215:403–10). BLAST produces alignments of both nucleotide and amino acid sequences to determine sequence similarity. Because of the local nature of the alignments, BLAST is especially useful in determining exact matches or in identifying homologs. Whereas it is ideal for matches which do not contain gaps, it is inappropriate for performing motif-style searching. The fundamental unit of BLAST algorithm output is the High-scoring Segment Pair (HSP).

An HSP consists of two sequence fragments of arbitrary but equal lengths whose alignment is locally maximal and for which the alignment score meets or exceeds a threshold or cutoff score set by the user. The BLAST approach is to look for HSPs between a query sequence and a database sequence, to evaluate the statistical significance of any matches found, and to report only those matches which satisfy the user-selected threshold of significance. The parameter E establishes the statistically significant threshold for reporting database sequence matches. E is interpreted as the upper bound of the expected frequency of chance occurrence of an HSP (or set of HSPs) within the context of the entire database search. Any database sequence whose match satisfies E is reported in the program output.

In addition, BLAST analysis was used to search for related molecules within the libraries of the LIFESEQ™ database. This process, an "electronic northern" analysis is analogous to northern blot analysis in that it uses one cellubrevin sequence at a time to search for identical or homologous molecules at a set stringency. The stringency of the electronic northern is based on "product score". The product score is defined as (% nucleotide or amino acid [between the query and reference sequences] in Blast multiplied by the % maximum possible BLAST score [based on the lengths of query and reference sequences]) divided by 100. At a product score of 40, the match will be exact within a 1–2% error; and at 70, the match will be exact. Homologous or related molecules can be identified by selecting those which show product scores between approximately 15 and 30.

6.19 SEQ ID NOs:1–8

Referring to FIG. 1, SEQ ID NO:1 is the nucleotide sequence of an expressed sequence tag corresponding to a polynucleotide isolated from a cDNA library of human fetal liver-spleen. SEQ ID NO:2 is an extended version of SEQ ID NO:1 obtained as described in Example 34, and the encoded polypeptide in SEQ ID NO:3 is referred to herein as CD39-L66. SEQ ID NO:2 encodes a polypeptide having the amino acid sequence of SEQ ID NO:3 (shown in FIG. 2). The open reading frame corresponding to SEQ ID NO:3 starts at nucleotide 246, as numbered from the 5' end of SEQ ID NO:2. This open reading frame encodes a polypeptide 428 amino acids in length. The estimated molecular weight of the unglycosylated polypeptide is approximately 47.52 kDa.

Figure 3:
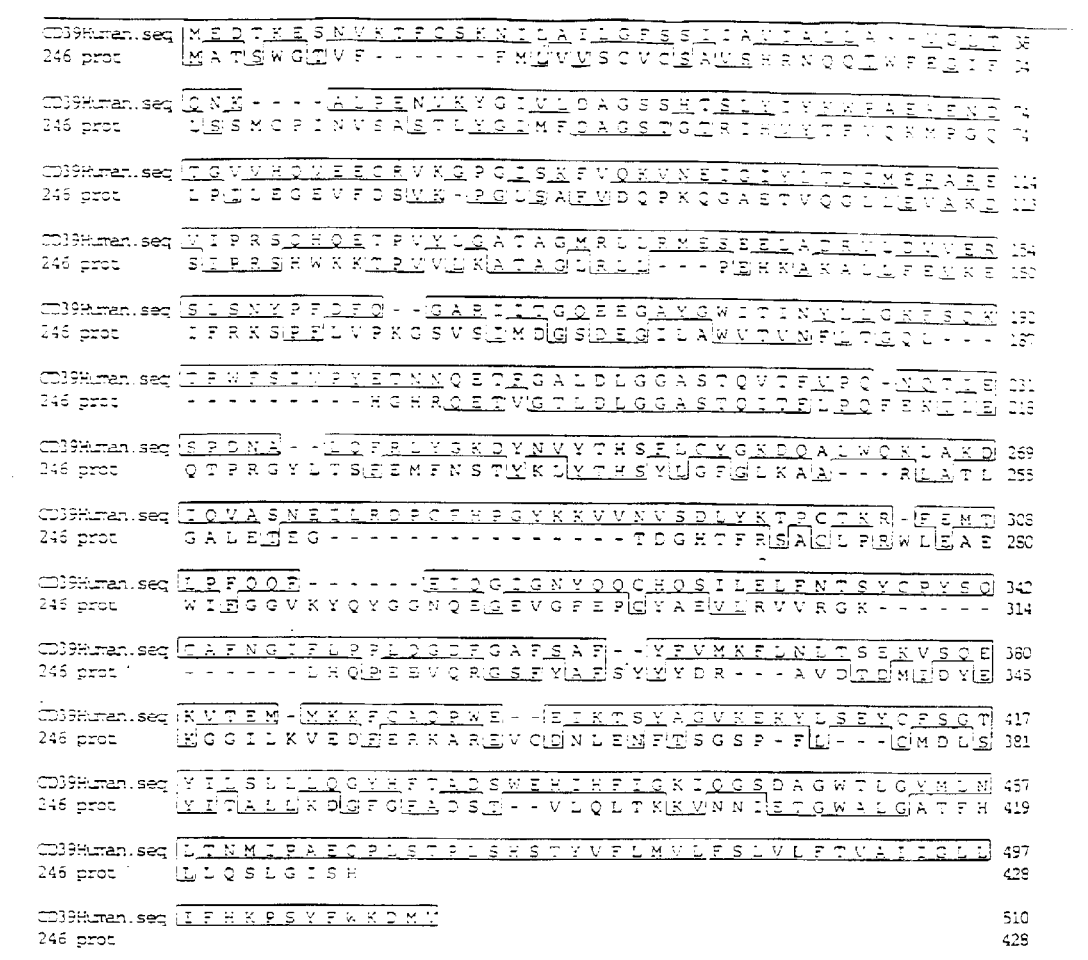

Protein database searches with the BLAST algorithm indicate that SEQ ID NO:3 is homologous to the CD39 family. FIG. 3 shows the amino acid sequence alignment between SEQ ID NO:3 (identified as "246 prot") and human CD39 ("CD39Human.seq"), indicating that the two sequences share 30% amino acid sequence identity. Moreover, a higher degree of homology between the apyrase conserved regions (Kaczmarek et al., J. Biol. Chem. 271:33116–33122 (1996) is observed. In particular, an almost perfect match to a putative ATP-binding region was found from amino acids 54–58, DAGST (DAGSS in CD39). In addition, the DLGGASTQ motif (DLGGASTQ in CD39), which is very well conserved among ATPDases, is found from amino acids 199–206 in SEQ ID NO:3. Other regions conserved in apyrases were found from amino acids 129–134, ATAGLR (ATAGMR in CD39) and from amino acids 169–173, GSDEG (GQEEG in CD39).

SEQ ID NO:3 differs from CD39 in that SEQ ID NO:3 contains a hydrophobic stretch of 22 amino acids at its amino terminus, which is indicative of a leader peptide. SEQ ID NO:3 also lacks the transmembrane domain found at the carboxyl terminus of CD39. These features indicate that SEQ ID NO:3 is a soluble ATPDase.

Figure 4:
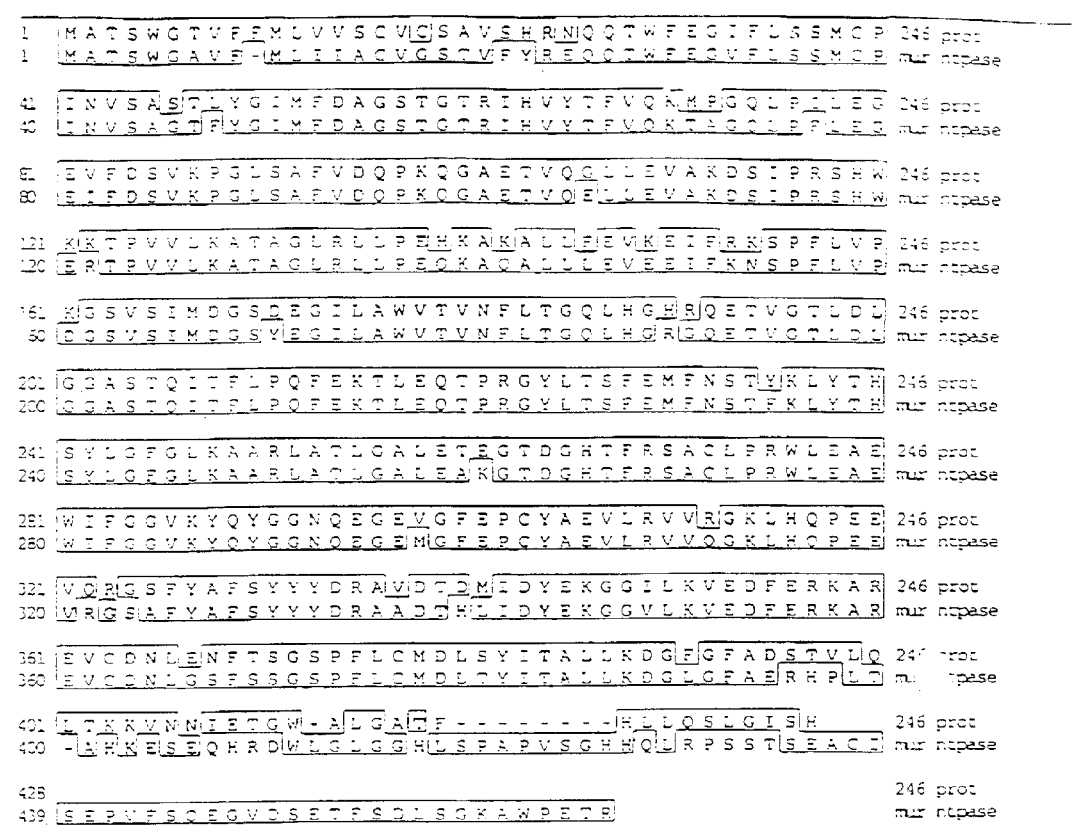

SEQ ID NO:3 shares an even higher degree of homology (83% identity) with a murine NTPase, as shown in the amino acid sequence alignment presented in FIG. 4 (SEQ ID NO:3 is identified as "246 prot," and mouse CD39 as "mur ntpase").

The message encoding SEQ ID NO:3 is tightly regulated in a tissue-specific manner. An expression study using a semiquantatative PCR/Southern blot approach revealed a significant level of expression in macrophage. In contrast, human CD39 is expressed in tissues such as placenta, lung, skeletal muscle, kidney, and heart.

SEQ ID NO: 4 is the polynucleotide sequence for CD39-L4, described in Chadwick et al., *Genomics*, 50(3):357–67 (1998); SEQ ID NO: 5 is the corresponding amino acid sequence.

SEQ ID NO: 6 is the polynucleotide sequence for a CD39-L4 variant designated ACRIII, wherein the following amino acid substitutions have been made: D168→T, S170→Q and L175→F; SEQ ID NO: 7 is the corresponding amino acid sequence.

SEQ ID NO:8 is the genomic sequence for the human CD39-L4 gene; exons appear at nucleotides 1–288 (exon 1), 1281–1580 (exon 2), 1820–1855 (exon 3) 2467–2555 (exon 4), 2863–2942 (exon 5), 3889–3950 (exon 6), 4894–4995 (exon 7), 5847–5987 (exon 8), 6966–7138 (exon 9) and 8556–9365 (exon 10).

6.20 Uses of Novel CD39-Like Polypeptides and Antibodies

Polypeptides of the invention having ATPDase activity are useful for inhibiting platelet function and can therefore be employed in the prophylaxis or treatment of pathological conditions caused by or involving thrombosis or excessive coagulation or excessive platelet aggregation, such as myocardial infarction, cerebral ischemia, angina, and the like. Polypeptides of the invention can also be used in the maintenance of vascular grafts. Platelet function can be measured by any of a number of standard assays, such as, for example, the platelet aggregation assay described in Example 5.

Such pathological conditions include conditions caused by or involving arterial thrombosis, such as coronary artery thrombosis and resulting myocardial infarction, cerebral artery thrombosis or intracardiac thrombosis (due to, e.g., atrial fibrillation) and resulting stroke, and other peripheral arterial thrombosis and occlusion; conditions associated with venous thrombosis, such as deep venous thrombosis and pulmonary embolism; conditions associated with exposure of the patient's blood to a foreign or injured tissue surface, including diseased heart valves, mechanical heart valves, vascular grafts, and other extracorporeal devices such as intravascular cannulas, vascular access shunts in hemodialysis patients, hemodialysis machines and cardiopulmonary bypass machines; and conditions associated with coagulapathies, such as hypercoagulability and disseminated intravascular coagulopathy. Co-administration of other agents suitable for treating the pathological condition, e.g., other anti-coagulation agents, is also contemplated.

In particular, variants like the ACRIII mutant described herein are expected to be superior therapeutics for treating such pathological conditions because (1) ACRIII exhibits six-fold greater activity compared to wild type CD39-L4, and (2) ACRIII, like CD39-L4, is uniquely specific for ADP and does not hydrolyze ATP. Thus, adverse side effects from hydrolysis of circulating ATP are avoided.

For instance, ATP is known to act as an extracellular signal in many tissues. In the heart, extracellular ATP modulates ionic processes and contractile function (for review see Burnstock, G., Neuropharmacology 36:1127). Recently, it has been shown that extracellular ATP markedly inhibits glucose transport in rat cardiomyocytes (Fisher Y. et al., J. Biol. Chem. 274:755–761. Another source of extracellular ATP is that released from parenchymal cells under hypoxic or ischemic conditions (Skobel, E., and Kammermeier, H. Biochim. Biophys. Acta 1362:128–134). ATP is also involved in the modulation of anti-IgE-induced release of histamine from human lung mast cells (Schulman E. S., et al., Am. J. Respir. Cell Mol. Biol. 20:520–537).

Furthermore, the ability of CD39-L4 to hydrolyze NDPs other than ADP has implications outside the circulatory system. For instance, it has been reported that UDP is the most potent agonist for the human P2Y$_6$ receptor. Communi, et al., Bioch Bioph Res Com 222:303–308 (1996). This receptor is expressed in several tissues including infiltrating T cells present in inflammatory bowel disease. Somers, et al., Lab Invest 78:1375–1383 (1998). In this microenvironment, a molecule with the enzymatic properties of CD39-L4 could influence T cell responses by modifying the extracellular half-life of UDP. Another role for CD39-L4 has been suggested by the report that mouse CD39-L4 maps closely to a locus associated with audigenic brain seizures in mice. See Chadwick, et al., Genomics 50:357–367 (1998); Seyfried, et al., Genetics 99:117–126 (1981). This locus, known as Asp-1, is thought to be linked or to correspond to a factor that influences $Ca^{2+}$-ATPase activity. Neumann, et al., Behav. Genetics 20:307–323 (1990).

Additionally, the polypeptides of the invention can be used as molecular weight markers, and as a food supplement. A polypeptide consisting of SEQ ID NO:3, for example, has a molecular mass of approximately 47.52 kD in its unglycosylated form. Protein food supplements are well known and the formulation of suitable food supplements including polypeptides of the invention is within the level of skill in the food preparation art.

The polypeptides of the invention are also useful for making antibody substances that are specifically immunoreactive with CD39-like proteins. Antibodies and portions thereof (e.g., Fab fragments) which bind to the polypeptides of the invention can be used to identify the presence of such polypeptides in a sample. For example, the level of the native protein corresponding to SEQ ID NO:3 in a blood sample can be determined as an indication of vascular condition. Such determinations are carried out using any suitable immunoassay format, and any polypeptide of the invention that is specifically bound by the antibody can be employed as a positive control.

The polypeptides of the invention are administered by any route that delivers an effective dosage to the desired site of action. The determination of a suitable route of administration and an effective dosage for a particular indication is within the level of skill in the art. For treatment of vascular disease, polypeptides according to the invention are generally administered intravenously. In vivo murine studies with soluble human CD39 have shown that mice injected intravenously with 50 mg recombinant soluble human CD39 in 100 ml sterile saline had biologically active CD39 in their sera for an extended period of time, with an elimination half-life of almost 2 days (Gayle, R. B., et al., J. Clinical Invest. 101:1851–1859 (1998)). Suitable dosage ranges for the polypeptides of the invention can be extrapolated from these dosages or from similar studies in appropriate animal models. Dosages can then be adjusted as necessary by the clinician to provide maximal therapeutic benefit.

The present invention is illustrated in the following examples. Upon consideration of the present disclosure, one of skill in the art will appreciate that many other embodiments and variations may be made in the scope of the present invention. Accordingly, it is intended that the broader aspects of the present invention not be limited to the disclosure of the following examples.

EXAMPLE 1

Isolation of SEQ ID NO:1 from a cDNA Library of Human Fetal Liver-Spleen

A plurality of novel nucleic acids were obtained from a b2HFLS20W cDNA library prepared from human fetal liver-spleen, as described in Bonaldo et al., Genome Res. 6:791–806 (1996), using standard PCR, SBH sequence signature analysis, and Sanger sequencing techniques. The inserts of the library were amplified with PCR using primers specific for vector sequences flanking the inserts. These samples were spotted onto nylon membranes and interrogated with oligonucleotide probes to give sequence signatures. The clones were clustered into groups of similar or identical sequences, and single representative clones were selected from each group for gel sequencing. The 5' sequence of the amplified inserts was then deduced using the reverse M13 sequencing primer in a typical Sanger sequencing protocol. PCR products were purified and subjected to fluorescent dye terminator cycle sequencing. Single-pass gel sequencing was done using a 377 Applied Biosystems (ABI) sequencer. One of these inserts was identified as a novel sequence not previously obtained from this library and not previously reported in public databases. This sequence is shown in FIG. 1 as SEQ ID NO:1.

EXAMPLE 2

Isolation of SEQ ID NO:2 and Determination of a Nucleotide Sequence Encoding a 428-Amino Acid Protein with Sequence Homology to CD39

The nucleotide sequence shown in FIG. 1, and labeled SEQ ID NO:2, encodes the translated amino acid sequence SEQ ID NO:3, which is shown in FIG. 2. The extended nucleotide sequence was obtained by isolating colonies generated from pools of clones from a human macrophage cDNA library (Invitrogen, Cat. #A550-25). Briefly, the macrophage cDNA library was plated on LB/Amp plates (containing 100 mg/ml ampicillin) at a density of about 40,000 colonies/plate. The colonies were lifted onto nitrocellulose filters and hybridized with a radiolabeled probe generated from the original clone (i.e., SEQ ID NO:1).

That the identified clones corresponded to SEQ ID NOs:1 and 2 was confirmed by using gene-specific primers (5'-GCTACCTCACTTCCTTTGAG-3' [SEQ ID NO: 9] and 5'-CTGGCTGGTGAAGTTTTCCTC-3' [SEQ ID NO: 10]) in a PCR-based assay. Then PCR using vector- and gene-specific primers was employed to amplify the 5' portion of the cDNA. Nested primers were used to generate sequence from the amplified product(s). Laser gene™ software was used to edit and "contig" the partial sequences into a full-length sequence. As discussed above, the amino acid sequence has striking homology to CD39, which is involved in modulating platelet reactivity during vascular inflammation. Based in part on the observed sequence similarity to CD39, the polypeptide encoded by SEQ ID NO: 2 was designated CD39-L66.

EXAMPLE 3

Expression Study Using SEQ ID NO:2

The expression of SEQ ID NO:2 in various tissues was analyzed using a semi-quantitative polymerase chain reaction-based technique. Human cDNA libraries were used as sources of expressed genes from tissues of interest (adult brain, adult heart, adult kidney, adult lymph node, adult liver, adult lung, adult ovary, adult placenta, adult spleen, adult testis, bone marrow, fetal kidney, fetal liver, fetal liver-spleen, fetal skin, fetal brain, fetal leukocyte and macrophage). Gene-specific primers (5'-GCTACCTCACTTCCTTTGAG-3' [SEQ ID NO: 9] and 5'-GCAGGTCTCCAAGGAAGTACG-3' [SEQ ID NO: 11]) were used to amplify portions of the SEQ ID NO:2 sequence from the samples. Amplified products were separated on an agarose gel, transferred and chemically linked to a nylon filter. The filter was then hybridized with a radioactively labeled ($\alpha^{33}$P-dCTP) double-stranded probe generated from the full-length SEQ ID NO:2 sequence using a Klenow polymerase, random-prime method. The filters were washed (high stringency) and used to expose a phosphorimaging screen for several hours. Bands indicated the presence of cDNA including SEQ ID NO:2 sequences in a specific library, and thus mRNA expression in the corresponding cell type or tissue.

Of the 18 human tissues tested, macrophage was the only sample that provided a signal, indicating that expression of SEQ ID NO:2 is tightly regulated. In contrast, the CD39 molecule has been found in tissues such as placenta, lung, skeletal muscle, kidney and heart.

EXAMPLE 4

Chromosomal Localization of the Gene Corresponding to SEQ ID NOs:1 and 2

Chromosome mapping technologies allow investigators to link genes to specific regions of chromosomes. Assignment to chromosome 14 was performed with the Coriell cell repository monochromosomal panel #2 (NIGMS cell repository). This human rodent somatic cell hybrid panel consists of DNA isolated from 24 hybrid cell cultures retaining 1 human chromosome each. The panel was screened with gene-specific primers (5'-GCTACCTCACTTCCTTTGAG-3' [SEQ ID NO: 9] and 5'-CTGGCTGGTGAAGTTTTCCTC-3' [SEQ ID NO: 10]) that generated a sequence tag site (STS). The Genebridge 4 radiation hybrid panel was also screened (Research Genetics), and the results of the PCR screening were submitted to the Whitehead/MIT Radiation Hybrid mapping email server at http://www-genome.wi.mit.edu.

EXAMPLE 5

Platelet Aggregation Assay

Blood is anticoagulated with 0.1 volume 3.2% sodium citrate. Platelet-rich plasma (PRP) is prepared with an initial whole blood centrifugation (200×g, 15 min., 25° C.) and a second centrifugation of the PRP (90×g, 10 min.) to eliminate residual erythrocytes and leukocytes. The stock suspension of PRP is maintained at room temperature under 5% $CO_2$-air. The platelet aggregation assay uses a two-sample, four-channel Whole Blood Lumi-Aggregometor, model 560 (Chronolog Corp., Havertown, Pa.). PRP containing 1.22× $10^8$ platelets is preincubated with the sample to be tested for inhibition of aggregation for 10 min. at 37° C. in a siliconized glass cuvette containing a stirring bar, followed by stimulation with either ADP (5 mm), collagen (5 mg/ml), or thrombin (0.1 unit/ml). Platelet aggregation is recorded for at least 10 min. Data are expressed as the percentage of light transmission with platelet-poor plasma equal to 100%.

EXAMPLE 6

CD39-L4 is a Soluble Apyrase

The mammalian ectoapyrase CD39 is an integral membrane protein with two transmembrane domains (one at each end of the protein) (Maliszewski, C. R. et al., J. Immunol. 153:3574–3583). The hydrophobicity profiles for the deduced amino acid sequence of other family members, such as CD39L1 and CD39L3, are very similar to CD39 (Chadwick B. P. and Frischauf A-M.; Genomics 50:357–367), suggesting that these proteins also have two membrane spanning domains. However, CD39-L4 does not appear to have a second transmembrane domain at its C-terminus, suggesting that the N-terminus hydrophobic region could code for a secretory signal. To test this hypothesis, CD39-L4 was subcloned into the mammalian expression vector pCDNA3.1 and a 6-Histidine tag was inserted into the coding sequence.

The CD39-L4 cDNA sequence was initially isolated from a macrophage cDNA library (Invitrogen). The sense primer (5'-TTAAAGCTTGGGAAAAGAATGAATGGCC-ACTTC-3', SEQ ID NO. 20) with a HindIII site and the antisense primer (5'-AGACTCGAGGT-GGCTCAATGGGAGATGCC-3', SEQ ID NO. 21) with a XhoI site were used to subclone the coding sequences into the mammalian expression vector pcDNA3.1 (Invitrogen). The nucleotide sequence of the insert is set forth in SEQ ID NO. 4. In order to immunologically detect the protein, the coding region was further modified so that it would include a Gly-Ser-6His epitope tag immediately following $Arg^{24}$. Briefly, two partially overlapping complementary oligonucleotides (5'-GCGCTGTCTCCCACAG- AGGATCG-CATC ACCATCACCATCACMCCAGCAGACTTGGTT-3' (SEQ ID. NO. 22) and 5'-AACCAAGTCTGCTGGTTGTG-ATGGTGATGGTGATGCGATCCTCTGTGGGAGACAG-CGC-3' (SEQ ID NO. 23)) were used on the CD39-L4 pcDNA3.1 template. The primers were extended in opposite directions around the plasmid using a 12 cycle PCR program (95° C., 1 minute; 60° C., 1 minute; 72° C., 15 minutes) (Stratagene). The reaction was treated with DpnI to digest the methylated parental DNA and then transformed into E. coli. Colonies were screened for the insert.

To ascertain whether CD39-L4-6His is secreted, the coding region of the CD39-L4-6His protein was inserted into the pcDNA3.1 expression vector and transiently transfected into COS-7 cells. Cos-7 cells obtained from the American Tissue Type Culture Collection were grown in DMEM supplemented with 10% FBS and 100 units/ml penicillin G and 100 μg/ml streptomycin sulfate at 37° C. in 10% $CO_2$. Transfections were performed at 75% confluency in 10 cm plates with Fugene-6 according to the manufacturers instructions. The cells in 7 mls of medium were incubated with 16

μl of Fugene-6 and 8 μg of DNA for 14–18 hours. At the end of the transfection the medium was replaced with DMEM medium containing low serum (1% FBS). The cells were then incubated for 24–48 hours prior to harvesting.

The CD39-L4-6His was concentrated by treating the cell lysates and medium with Nickel-NTA agarose (Qiagen) followed by SDS/PAGE and immunoblot analysis with an antibody against the Arg-Gly-Ser-6His epitope. Cells were washed twice with PBS containing 0.5 μg/ml leupeptin, 0.7 μg/ml pepstatin and 0.2 μg/ml aprotinin. After a brief sonication and centrifugation step to clear the lysate, the samples were then incubated with a Nickel-NTA resin at 4° C. for 2–3 hours. The histidine-tagged protein complexed to the resin was washed three times with PBS before loading onto a 10% SDS/PAGE gel for Western blot analysis. CD39-L4 was detected in both the cell lysate and the medium from cells transfected with the CD39-L4-6His expression vector, but not from control cells. While the predicted molecular weight of CD39-L4-6His is 46 kDa, the immunoreactive protein exhibited a mobility by SDS/PAGE corresponding to a molecular mass of approximately 51 kDa in the media and approximately 48 kDa in the cell lysate. The difference in apparent molecular weight may be due to posttranslational modications of three potential N-glycosylation sites in the CD39-L4 predicted amino acid sequence.

Secretion of CD39-L4 was also examined by treatment of the transfected cells with brefeldin A, an inhibitor of translocation of secretory proteins from the endoplasmic reticulum to the Golgi apparatus. Chadwick, et al., Genomics 50:357–367 (1998). Brefeldin A was dissolved in ethanol and added to the transfected cells 48 hours after transfection. Both control and brefeldin A treated cells were washed once with PBS and incubated for 8 hours in medium with none or varying dosages of brefeldin A. Increasing dosages of brefeldin A blocked secretion of CD39-L4-6His and led to massive intracellular accumulation.

EXAMPLE 7

Site-directed Mutagenesis of CD39L4

Site directed mutagenesis was employed to increase the enzymatic activity of CD39L4. Amino acid sequence comparisons between CD39 family members reveal four highly homologous regions in all five human members (Chadwick and Frischauf, Genomics 50:357–367, 1998). These regions, termed apyrase-conserved regions (ACRs), are present not only in the CD39 family members but other apyrases from species as distant as yeast and plants. Examination of similarities and differences in the CD39 ACRs led to the design of three CD39L4 mutants (see FIG. 5). In these mutants, codons encoding CD39 ACR specific residues were used to replace codons from the CD39L4 wild type ACR sequence. Only residues with significantly different structural or chemical properties were replaced. A PCR based approach was used to produce these mutations.

Briefly, the expression vector pCDNA3.1 (Invitrogen) containing the full coding sequence of the CD39L4 gene (with a 6 Histidine tag inserted after Arg 24 in the coding sequence to allow purification of the secreted mature form of the protein) was subjected to a PCR-based site-directed mutagenesis approach using overlapping oligonucleotides [CD39-L4 ACR I mutant (nt 177–148 and 160–204):5'-GTG AGT GCT CCC TGC ATC TAA CAT AAT TCC-3' (SEQ ID NO: 12) and 5'-GAT GCA GGG AGC ACT CAC ACT AGT ATT CAT GTT TAC ACC TTT GTG-3' (SEQ ID NO: 13); CD39-L4 ACRII mutant (nt 402–359 and 385–415): 5'-GCG TAG TCC TGC TGT TGC CCC TAG GTA CAC TGG GGT CTT TTT CC-3' (SEQ ID NO: 14) and 5'-GCA ACA GCA GGA CTA CGC TTA CTG CCA GAA C-3' (SEQ ID NO: 15); and CD39-L4 ACR III mutant (nt 532–485 and 513–540): 5'-CCC AAG CGA ATA TGC CTT CGT CTT GTC CAG TCA TGA TGC TAA CAC TGC-3' (SEQ ID NO: 16) and 5'-CGA AGG CAT ATT CGC TTG GGT TAC TGT G-3' (SEQ ID NO:17)]. After amplification of the whole plasmid with Pfu DNA polymerase (Stratagene) (95° C./1 min; 60° C./1 min; 72° C./15 min for 12 cycles), the methylated parental DNA was digested with the restriction enzyme DpnI, leaving only the unmethylated PCR amplified products. The resulting annealed double-stranded nicked products were then transformed into bacteria and the resulting colonies were screened for the desired mutations by sequencing. The subsequent constructs were fully sequenced to verify that the mutations were in fact introduced and that no extraneous mutations were generated.

EXAMPLE 8

ACR III Mutant Increases ADPase Activity

Plasmids containing the mutated and wild type forms of the CD39L4 gene were transfected into COS-7 cells. After two days, protein was purified from the culture medium using a Nickel-NTA resin approach to concentrate the tagged proteins. These proteins were then assayed for ATPase and ADPase activity by measuring the inorganic phosphate released (Wang T-F et al., J. Biol. Chem. 273:24814–24821, 1998). The proteins were incubated in apyrase buffer (15 mM Tris pH 7.4, 135 mM NaCl, 2mM EGTA and 10 mM glucose) for 1 hour at 37° C. with or without 2 mM $CaCl_2$ or 2 mM $MgCl_2$. Phosphatase reactions were initiated by the addition of ADP or ATP to a final concentration of 1 mM. The reaction of inorganic phosphorus with ammonium molybdate in the presence of sulfuric acid, produces an unreduced phosphomolybdate complex. The absorbance of this complex at 340 nm is directly proportional to the inorganic phosphorus concentration (Daly J. A., and Ertingshausen G. Clin. Chem. 18:263 (1972) (Sigma Diagnostics)).

Figure 7:
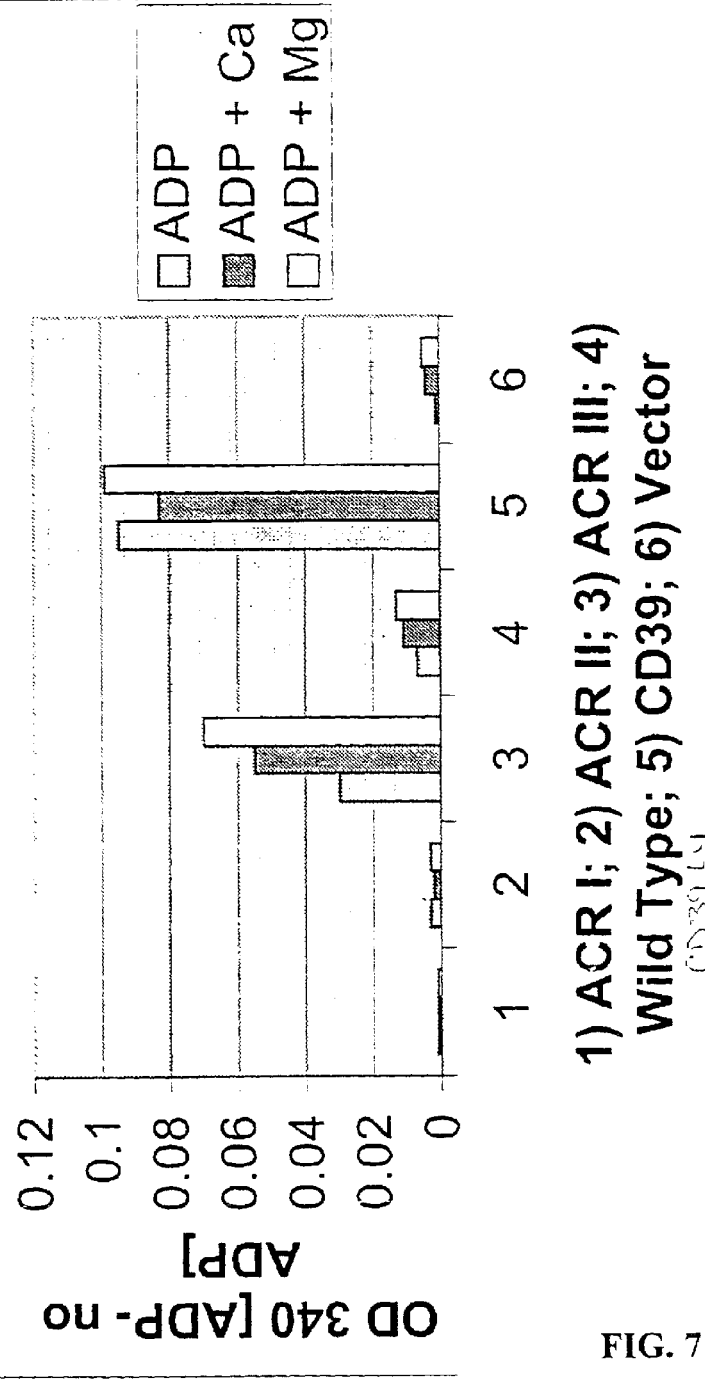
FIG. 7 shows the ADPase activity of CD39-L4 variants ACRI, ACRII and ACRIII in comparison to wild type CD39-L4: (1) CD39-L4 ACR I mutant; (2) CD39-L4 ACR II mutant; (3) CD39-L4 ACR III mutant; (4) CD39-L4 wild type; (5) sCD39; and (6) pSecTag2 vector (Invitrogen).

As seen in FIG. 7, mutations in ACR I and II eliminate activity, whereas the mutations in ACR III increase activity six-fold over wild type. This increased activity therefore offers a greater therapeutic potential, as less protein could be administered to offer the same pharmacological effect. The replacement of three amino acids in the III region (amino acids 167 to 181 in CD39-L4) and the resulting increase in ADPase activity predicts that replacement of additional amino acids within this region by amino acids from the equivalent region of CD39 may also enhance the activity of the protein over wild type CD39L4. The increase in ADPase activity over wild type may also be due to the replacement of only one or two of the three amino acids; this can be confirmed by replacing one or two amino acids at a time.

The polynucleotide and amino acid sequences of a CD39-L4 variant termed ACRIII and having the amino acid substitutions D168→T, S170→Q and L175→F compared to wild type CD39-L4 (SEQ ID NO: 5) are set forth in SEQ ID NOs: 6 and 7, respectively, and in FIG. 6.

EXAMPLE 9

ACR III Mutant and Wild Type Forms are Specific for ADP and not ATP

Both the CD39L4 wild type and the CD39L4 variant with mutations in the ACRIII region hydrolyze ADP. However, when ATP was tested as a substrate, neither the CD39L4 nor the CD39L4 variant catalyzed hydrolysis. In contrast, CD39 as a membrane bound molecule (Marcus et al., The Journal of Clinical Investigation, 99:1351–1360) or as a genetically engineered soluble form (Gayle et al., The Journal of Clinical Investigation, 101:1851–1858, 1998) is able to hydrolyze both ATP and ADP substrates efficiently. The specificity that both CD39L4 wild type and the CD39L4 variant with mutations in the ACRIII region have for ADP is an advantageous feature that makes these CD39L4-type molecules better antiplatelet therapeutic candidates than CD39, as ADP is the agonist that causes platelet aggregation. Therapeutics that have both ADPase and ATPase activities potentially could create adverse side effects by interfering with levels of ATP in the circulation.

EXAMPLE 10

Organization of the Human CD39-L4 Gene

A human CITB BAC genomic library (Research Genetics) was screened with gene specific primers [246-I6 (nt 5522–5543), 5'-CTTCCTTCACTGGGAATTCAGG-3' (SEQ ID NO: 18) and 246-K4 (nt 4922–4945), 5'-CTGTTTACCGAGATGGTTGGAAGC-3' (SEQ ID NO: 19)] using a PCR based assay.

Briefly, gene specific primers were used to screen pools of BAC DNAs. BAC pools that produced a amplified DNA fragment of the predicted size were pursued until an individual BAC was identified. BAC63-I18 was isolated and sequenced with gene specific primers for the CD39-L4 cDNA, as well as intron specific primers. The CD39-L4 coding sequence was found to be distributed over 10 exons spanning 9.3 kb of genomic DNA as set out in SEQ ID NO: 8.

EXAMPLE 11

CD39-L4 is Stimulated by Divalent Cations

The high degree of conservation in the apyrase conserved regions of CD39-L4 suggests similar function to other apyrases. To test this hypothesis, COS-7 cells were transfected with the CD39-L4-6His construct as described above. The medium from transfected cells was incubated with Nickel-NTA resin (Qiagen) in order to capture the 6His tagged protein, the resin was washed with assay buffer (buffer A, 15 mM Tris pH 7.5, 134 mM NaCl and 5 mM glucose) and the protein still tethered to the resin in a suspension was assayed for ADPase activity. Nucleotidase activity was determined by measuring the amount of inorganic phosphate released from nucleotide substrates using the technique of Dlay and Ertingshausen, Clin. Chem. 18:263–265 (1972). In this reaction the complex of inorganic phosphorus with phosphor reagent (ammonium molybdate in the presence of sulfuric acid) produces an unreduced phosphomolybdate compound. The absorbance of this complex at 340 nm is directly proportional in the inorganic phosphorus concentration. The protein still tethered to the resin as a 30% suspension in buffer A was assayed by the addition of the nucleotide to a final concentration of 1 mM and incubated at 37° C. for 30 minutes. The reaction was stopped by adding 100 volumes of phosphor reagent. The amount of phosphate released from the reaction was quantified using a calcium/phosphorus combined standard (Sigma). The amount of CD39-L4 protein used in the assays was estimated by comparing the intensity of the CD39-L4 band in Western blots with that of a series of standards of known quantity. CD39-L4 protein from transfected cells displayed a 2.3 fold increase in activity over the cells transfected with the vector alone. When $Ca^{2+}$ and $Mg^{2+}$ were added, the activity increased 3.6 fold and 6 fold, respectively.

EXAMPLE 12

Characterization of CD39-L4 Activity

CD39-L4 protein was assayed for ADPase activity in the presence of different kinds of inhibitors of ADPases. Control ecto-apyrase activity was determined with protein tethered to the Nickel-NTA resin. Both assays were performed as described above except the protein was in buffer A containing 2 mM $CaCl_2$ and 2 mM $MgCl_2$. As shown by Table 1 below, inhibitors of phosphatases ($F^-$) and adenylate kinase (Ap5A) did not inhibit activity. The inhibitors of vacuolar ATPases (NEM), mitochondrial ATPases ($N3^-$) and $Na^+$, $K^+$, ATPase (oubain) did not significantly inhibit the $Ca^{2+}$ and $Mg^{2+}$ stimulated activity. However, metal chelators (EDTA and EGTA) significantly inhibited activity. These results show that the overwhelming majority of the activity in the assays originates from a protein bound to the resin with characteristics of an E-type apyrase.

TABLE 1

| Inhibition of CD39-L4 activity | |
|---|---|
| INHIBITORS | % OF CONTROL |
| Control | 100 ± 7 |
| Ouabain (1 mM) | 96 ± 6 |
| NEM (10 mM) | 106 ± 5 |
| $N3^-$ (1 mM) | 100 ± 12 |
| $F^-$ (10 mM) | 113 ± 5 |
| Ap5A (10 µM) | 121 ± 9 |
| EGTA (2 mM) | 35 ± 3 |
| EDTA (2 mM) | 52 ± 3 |

As shown in Table 2 below, the nucleotide specificity of CD39-L4 was also assayed as described above. The CD39-L4 activity was determined with protein tethered to the Ni-NTA resin. The protein was in buffer A containing 1 mM EGTA, as well as 2 mM $CaCl_2$ and $MgCl_2$. The assay was started by adding the nucleotides to a final concentration of 1 mM. The values below are expressed relative to ADP. The relative activity of the nucleotide triphosphates varies almost seven-fold with ATP being the poorest substrate. No phosphate release was detected with AMP and ADP was hydrolyzed at a rate approximately twenty-fold higher than ATP. The other nucleotide diphosphates (GDP and UDP) were also very efficiently hydrolyzed by CD39-L4. These results indicate that CD39-L4 defines a new class of E-type apyrase in humans with a specificity for NDPs as enzymatic substrates.

TABLE 2

| Substrate specificity of CD39-L4 | |
|---|---|
| NUCLEOTIDE | % OF CONTROL |
| ADP | 100 ± 15 |
| ATP | 5 ± 1 |
| AMP | 0 |
| CTP | 26 ± 2 |
| GTP | 34 ± 1 |
| UTP | 12 ± 4 |
| CDP | 268 ± 11 |

TABLE 2-continued

Substrate specificity of CD39-L4

| NUCLEOTIDE | % OF CONTROL |
|---|---|
| GDP | 334 ± 38 |
| UDP | 408 ± 14 |

EXAMPLE 13

Glycosylation is not Essential for CD39-L4 Activity

Posttranslational modifications such as N-linked glycosylation are common in secreted and membrane-bound mammalian proteins. These modifications may be important for correct protein folding or enzymatic activity and are not easily reproduced when the proteins are expressed in other organisms such as bacteria. In order to test whether CD39-L4 is glycosylated, COS-7 cells, transfected as described in Example 43, were treated with tunicamycin (Sigma), which blocks the formation of N-glycosidic linkages.

COS-7 cells were grown to 75% confluency and transfected with the CD39-L4-6His construct. After 24 hours, a fraction of the COS-7 cells were treated with Tunicamycin at a concentration of 5 μg/ml. The media was replaced again after 24 hours with fresh tunicamycin and harvested after 48 hours. The CD39-L4-6His protein was concentrated by treating the media with Nickel-NTA agarose (Qiagen). The resin was washed with assay buffer and the protein still tethered to the resin in a suspension was assayed for a shift in electrophoretic mobility as well as its ADPase activity.

Western blot analysis using an antibody against the 6-His epitope revealed that the glycosylated CD39-L4 protein isolated from the control cells had an approximate size of 51 kDa. However, tunicamycin treated cells had a molecular weight of approximately 46 kDa indicating that the protein was deglycosylated.

ADPase activity of the tunicamycin treated cells was assayed as described in Example 13 above. The deglycosylated CD39-L4 protein had ADPase activity comparable to an equal amount of the glycosylated protein isolated from control cells. This demonstrates that glycosylation of the protein is not important for ADPase activity.

The present invention is not to be limited in scope by the exemplified embodiments which are intended as illustrations of single aspects of the invention, and compositions and methods which are functionally equivalent are within the scope of the invention. Indeed, numerous modifications and variations in the practice of the invention are expected to occur to those skilled in the art upon consideration of the present preferred embodiments. Consequently, the only limitations which should be placed upon the scope of the invention are those which appear in the appended claims.

All references cited within the body of the instant specification are hereby incorporated by reference in their entirety.

What is claimed is:

1. An isolated polypeptide comprising the amino acid sequence of SEQ ID NO: 3 wherein the polypeptide comprises at least one amino acid substitution selected from the group consisting of: D168→T, S170→Q and L175→F.

2. The polypeptide of claim 1 comprising a polypeptide having the amino acid sequence set forth in SEQ ID NO: 7.

3. A composition comprising the polypeptide of claim 1 and a pharmaceutically acceptable carrier.

* * * * *